United States Patent
Frendéus et al.

(10) Patent No.: US 11,447,549 B2
(45) Date of Patent: Sep. 20, 2022

(54) COMBINATION OF A TREG DEPLETING ANTI-4-1BB ANTIBODY AND ANTI-PD1 ANTIBODY

(71) Applicants: BIOINVENT INTERNATIONAL AB, Lund (SE); CANCER RESEARCH TECHNOLOGY LIMITED, London (GB)

(72) Inventors: Björn Frendéus, Lund (SE); Linda Mårtensson, Bjarred (SE); Monika Semmrich, Malmo (SE); Ingrid Teige, Lund (SE); Stephen Beers, Southampton (GB); Aymen Al-Shamkhani, Southampton (GB); Juliet Gray, Southampton (GB); Martin Glennie, Southampton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 135 days.

(21) Appl. No.: 16/633,740

(22) PCT Filed: Jul. 26, 2018

(86) PCT No.: PCT/EP2018/070359
§ 371 (c)(1),
(2) Date: Jan. 24, 2020

(87) PCT Pub. No.: WO2019/020774
PCT Pub. Date: Jan. 31, 2019

(65) Prior Publication Data
US 2020/0207855 A1    Jul. 2, 2020

(30) Foreign Application Priority Data
Jul. 26, 2017   (GB) ..................................... 1712032

(51) Int. Cl.
*A61K 39/395* (2006.01)
*C07K 16/28* (2006.01)
*A61K 39/00* (2006.01)

(52) U.S. Cl.
CPC ...... *C07K 16/2815* (2013.01); *C07K 16/2878* (2013.01); *A61K 2039/507* (2013.01); *C07K 16/2827* (2013.01); *C07K 2317/53* (2013.01); *C07K 2317/565* (2013.01); *C07K 2317/732* (2013.01); *C07K 2317/75* (2013.01); *C07K 2317/76* (2013.01)

(58) Field of Classification Search
None
See application file for complete search history.

(56) References Cited

U.S. PATENT DOCUMENTS

2016/0176963 A1   6/2016   Maurer et al.

FOREIGN PATENT DOCUMENTS

| WO | WO 2015/145360 A1 | 10/2015 |
|----|-------------------|---------|
| WO | WO 2016/029073 A2 | 2/2016 |
| WO | WO 2016/154177 A2 | 9/2016 |
| WO | WO 2016/200835 A1 | 12/2016 |
| WO | WO 2017/077085 A2 | 5/2017 |
| WO | WO 2017/174331 A1 | 10/2017 |
| WO | WO 2018/225035 A1 | 12/2018 |

OTHER PUBLICATIONS

Arce-Vargas et al., "Fc-optimized anti-CD25 depletes tumor-infiltrating regulatory T cells and synergizes with PD-1 blockade to eradicate established tumors," *Immunity* 46(4):577-586, 2017.
Beatty et al.,"CD40 agonists alter tumor stroma and show efficacy against pancreatic carcinoma in mice and humans". *Science*, 331:1612-1616, 2011.
Beers et al., "Type II (tositumomab) anti-CD20 monoclonal antibody out performs type I (rituximab-like) reagents in B-cell depletion regardless of complement activation," *Blood*, 112:4170-4177, 2008.
Beers et al., "Antigenic modulation limits the efficacy of anti-CD20 antibodies: implications for antibody selection". *Blood*, 115:5191-5201, 2010.
Brahmer et al., "Safety and activity of anti-PD-L1 antibody in patients with advanced cancer". *N Engl J Med*, 366:2455-2465, 2012.
Buchan and Al-Shamkhani, "Distinct motifs in the intracellular domain of human CD30 differentially activate canonical and alternative transcription factor NF-kappaB signalling". *PLoS One*, 7:e45244, 2012.
Bulliard et al., "Activating Fc gamma receptors contribute to the antitumor activities of immunoregulatory receptor-targeting antibodies". *J Exp Med*, 210:1685-1693, 2013.
Curti et al., "OX40 is a potent immune-stimulating target in late-stage cancer patients". *Cancer Res*, 73:7189-7198, 2013.
Curran and Allison, 2009 ("Tumor vaccines expressing flt3 ligand synergize with ctla-4 blockade to reject preimplanted tumors". *Cancer Res*, 69:7747-7755).
Curran et al., "Combination CTLA-4 blockade and 4-1BB activation enhances tumor rejection by increasing T-cell infiltration, proliferation, and cytokine production". *PLoS One* 6:e19499, 2011.
Dahan et al., "Therapeutic Activity of Agonistic, Human Anti-CD40 Monoclonal Antibodies Requires Selective FcγR Engagement," *Cancer Cell*, 2016 29(6):820-31, 2016.

(Continued)

*Primary Examiner* — Phillip Gambel
(74) *Attorney, Agent, or Firm* — ParkerHighlander, PLLC

(57) ABSTRACT

Described is the sequential administration of first a Treg depleting antibody molecule selected from antibody molecules, such as an antibody molecule binding specifically to target belonging to the tumour necrosis factor receptor superfamily (TNFRSF), such as a Treg depleting anti-4-1 BB antibody or a Treg depleting OX-40 antibody, and then an immunostimulatory antibody molecule, such as an immunostimulatory anti-4-1 BB anti-body or an immunostimulatory OX-40 antibody, for use in the treatment of cancer. Described are also novel anti-4-1 BB antibodies and novel OX-40 antibodies that may be used in such sequential administration.

14 Claims, 32 Drawing Sheets

Specification includes a Sequence Listing.

(56) References Cited

OTHER PUBLICATIONS

De Simone et al., "Transcriptional Landscape of Human Tissue Lymphocytes Unveils Uniqueness of Tumor-Infiltrating T Regulatory Cells," *Immunity*, 45:1135-1147.

Elpek et al., "Ex vivo expansion of CD4+CD25+FoxP3+ T regulatory cells based on synergy between IL-2 and 4-1BB signalling". *J Immunol*, 179:7295-7304, 2007.

French et al., "CD40 antibody evokes a cytotoxic T-cell response that eradicates lymphoma and bypasses T-cell help". *Nat Med*, 5:548-553, 1999.

Furness et al., "Impact of tumour microenvironment and Fc receptors on the activity of immunomodulatory antibodies". *Trends Immunol*, 35:290-298, 2014.

Gavin et al., "Homeostasis and anergy of CD4(+)CD25(+) suppressor T cells in vivo". *Nat Immunol*, 3:33-41, 2002.

Gros et al., "PD-1 identifies the patient-specific CD8(+) tumor-reactive repertoire infiltrating human tumors". *J Clin Invest*, 124:2246-2259, 2014.

Guo et al., "PD-1 blockade and OX40 triggering synergyistically protects against tumor growth in a murine model of ovarian cancer". *PLoS One*, 9(2):e89350, 2014.

Haynes et al., "CD11c+ dendritic cells and B cells contribute to the tumoricidal activity of anti-DR5 antibody therapy in established tumors". *J Immunol*, 185:532-541, 2010.

Hodi et al., "Improved survival with ipilimumab in patients with metastatic melanoma". *N Engl J Med*, 363:711-723, 2010.

Houot et al., "Therapeutic effect of CD137 immunomodulation in lymphoma and its enhancement by Treg depletion". *Blood*, 114(16):3431-3438, 2009.

Li and Ravetch, "Inhibitory Fcgamma receptor engagement drives adjuvant and anti-tumor activities of agonistic CD40 antibodies". *Science*, 333:1030-1034, 2011.

Li and Ravetch, "A general requirement for FcgammaRIIB co-engagement of agonistic anti-TNFR antibodies". *Cell Cycle*, 11:3343-3344, 2012.

Li and Ravetch, "Apoptotic and antitumor activity of death receptor antibodies require inhibitory Fcgamma receptor engagement". *Proc Natl Acad Sci U S A*, 109:10966-10971, 2012.

Li and Ravetch, "Antitumor activities of agonistic anti-TNFR antibodies require differential FcgammaRIIB coengagement in vivo". *Proc Natl Acad Sci U S A* 110:19501-19506, 2013.

Lim et al., "Fc gamma receptor IIb on target B cells promotes rituximab internalization and reduces clinical efficacy". *Blood*, 118:2530-2540, 2011.

Linch et al., "OX40 agonists and combination immunotherapy: putting the pedal to the metal". *Frontiers in Oncology*, 5:1-14, 2015.

Lode et al., "Targeted interleukin-2 therapy for spontaneous neuroblastoma metastases to bone marrow". *J Natl Cancer Inst*, 89:1586-1594, 1997.

Mahoney et al., "Combination cancer immunotherapy and new immunomodulatory targets". *Nature Reviews Drug Discovery*, 14(8):561-584, 2015.

Marabelle et al., "Depleting tumor-specific Tregs at a single site eradicates disseminated tumors". *J Clin Invest*, 123:2447-2463, 2013.

Marson et al., "Foxp3 occupancy and regulation of key target genes during T-cell stimulation". *Nature*, 445:931-935, 2007.

McHugh et al., "CD4(+)CD25(+) immunoregulatory T cells: gene expression analysis reveals a functional role for the glucocorticoid-induced TNF receptor". *Immunity*, 16:311-323, 2002.

Melero et al., "Agonist antibodies to TNFR molecules that costimulate T and NK cells". *Clin Cancer Res*, 19:1044-1053, 2013.

Messenhemier et al., "Timing of PD-1 blockade is critical to effective combination immunotherapy with anti-OX40". *Clin Cancer Res*, OF1-13, 2017.

Middendorp et al., "Mice deficient for CD137 ligand are predisposed to develop germinal center-derived B-cell lymphoma". *Blood*, 114:2280-2289, 2009.

Mimoto et al., "Engineered antibody Fc variant with selectively enhanced FcgammaRIIb binding over both FcgammaRIIa(R131) and FcgammaRIIa(H131)". *Protein Eng Des Sel*, 26:589-598, 2013.

Minard-Colin et al., "Lymphoma depletion during CD20 immunotherapy in mice is mediated by macrophage FcgammaRI, FcgammaRIII, and FcgammaRIV". *Blood*, 112:1205-1213, 2008.

Molckovsky and Siu, "First-in-class, first-in-human phase I results of targeted agents: highlights of the 2008 American society of clinical oncology meeting". *J Hematol Oncol*, 1:20, 2008.

Moore et al., "Introduction of soluble protein into the class I pathway of antigen processing and presentation". *Cell*, 54(6):777-85.

Nimmerjahn and Ravetch, "Divergent immunoglobulin g subclass activity through selective Fc receptor binding". *Science*, 310:1510-1512, 2005.

Offringa et al., "Development of next-generation immunomodulatory antibodies for cancer therapy through optimization of the IgG framework". *Cancer Cell*, 28(3):273-275, 2015.

Piconese et al., "OX40 triggering blocks suppression by regulatory T cells and facilitates tumor rejection". *The Journal of Experimental Medicine*, 205(4):825-839, 2008.

Plitas et al., "Regulatory T Cells Exhibit Distinct Features in Human Breast Cancer". *Immunity*, 45:1122-1134, 2016.

Römer et al., "Preculture of PBMCs at high cell density increases sensitivity of T-cell responses, revealing cytokine release by CD28 superagonist TGN1412". *Blood.*, (26):6772-82, 2011.

Segal et al., "A phase 1 study of PF-05082566 (anti-4-1BB) in patients with advanced cancer". *J Clin Oncol*, 32:suppl; abstr 3007, 2014.

Sharma et al., "Novel cancer immunotherapy agents with survival benefit: recent successes and next steps". *Nat Rev Cancer*, 11:805-812, 2011.

Shrimati et al., "Concurrent PD-1 blockade negates the effect of OX40 agonist antibody in combination immunotherapy through inducing T-cell apoptosis". Cancer Immunol Res, 5(9):755-766, 2017.

Simpson et al., "Fc-dependent depletion of tumor-infiltrating regulatory T cells co-defines the efficacy of anti-CTLA-4 therapy against melanoma". *J Exp Med*, 210:1695-1710, 2013.

Snell et al., "T-cell intrinsic effects of GITR and 4-1BB during viral infection and cancer immunotherapy". *Immunol Rev*, 244:197-217, 2011.

Taraban et al., "Expression and costimulatory effects of the TNF receptor superfamily members CD134 (OX40) and CD137 (4-1BB), and their role in the generation of anti-tumor immune responses". *Eur J Immunol*, 32:3617-3627, 2002.

Tipton et al., "Anti-mouse FcgammaRIV antibody 9E9 also blocks FcgammaRIII in vivo". *Blood*, 126:2643-2645, 2015.

Topalian et al., "Safety, activity, and immune correlates of anti-PD-1 antibody in cancer". *N Engl J Med*, 366:2443-2454, 2012.

White et al., "Interaction with FcγRIIB is critical for the agonistic activity of anti-CD40 monoclonal antibody". *J Immunol*, 187:1754-1763, 2011.

White et al., "FcgammaRIotaIotaB controls the potency of agonistic anti-TNFR mAbs". *Cancer Immunol Immunother*, 62:941-948, 2013.

White et al., "Fcgamma receptor dependency of agonistic CD40 antibody in lymphoma therapy can be overcome through antibody multimerization". *J Immunol*, 193:1828-1835, 2014.

White et al., "FcgammaRIIB as a key determinant of agonistic antibody efficacy". *Curr Top Microbiol Immunol*, 382:355-372, 2014.

White et al., "Conformation of the human immunoglobulin G2 hinge imparts superagonistic properties to immunostimulatory anti-cancer antibodies". *Cancer Cell* 27(1):138-148, 2015.

Wilson et al., "An Fcgamma receptor-dependent mechanism drives antibody-mediated target-receptor signaling in cancer cells". *Cancer Cell*, 19:101-113, 2011.

Yonezawa et al., "Boosting cancer immunotherapy with anti-CD137 antibody therapy". *Clinal Cancer Research*, 21(14):3113-3120, 2015.

Zheng et al., "The 4-1BB costimulation augments the proliferation of CD4+ CD25+ regulatory T cells," *The Journal of Immunology* 173.4 (2004): 2428-2434.

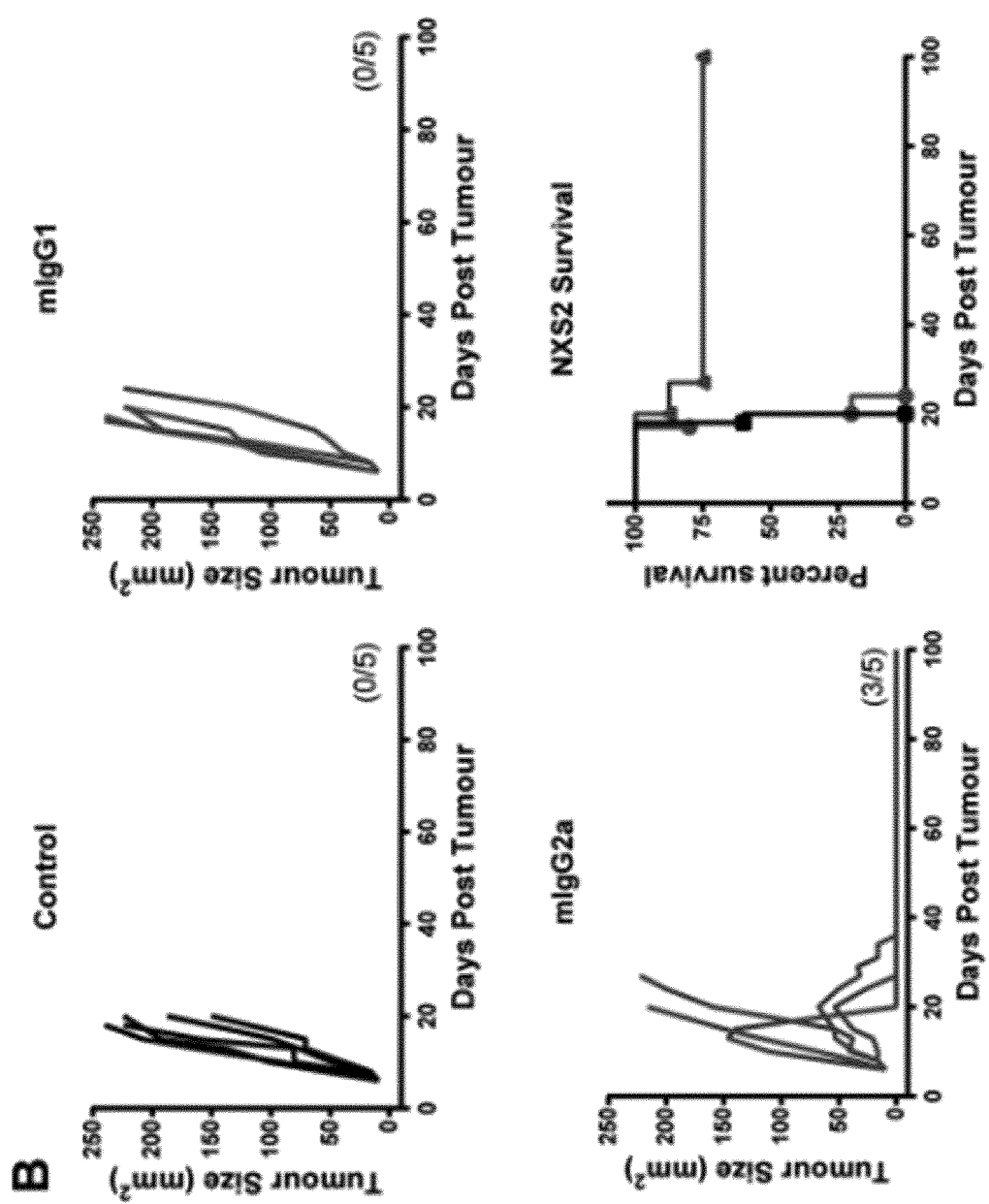
*Fig. 1, cont.*

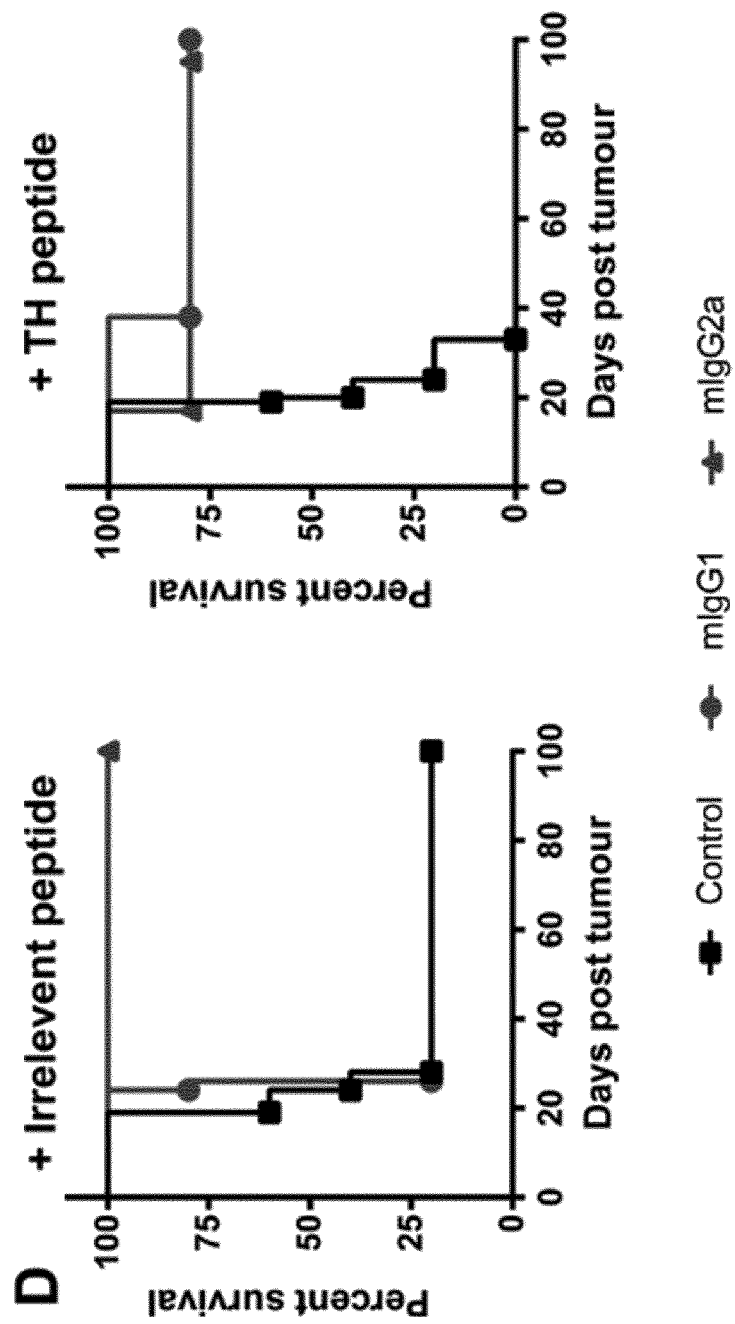
Fig. 2, cont.

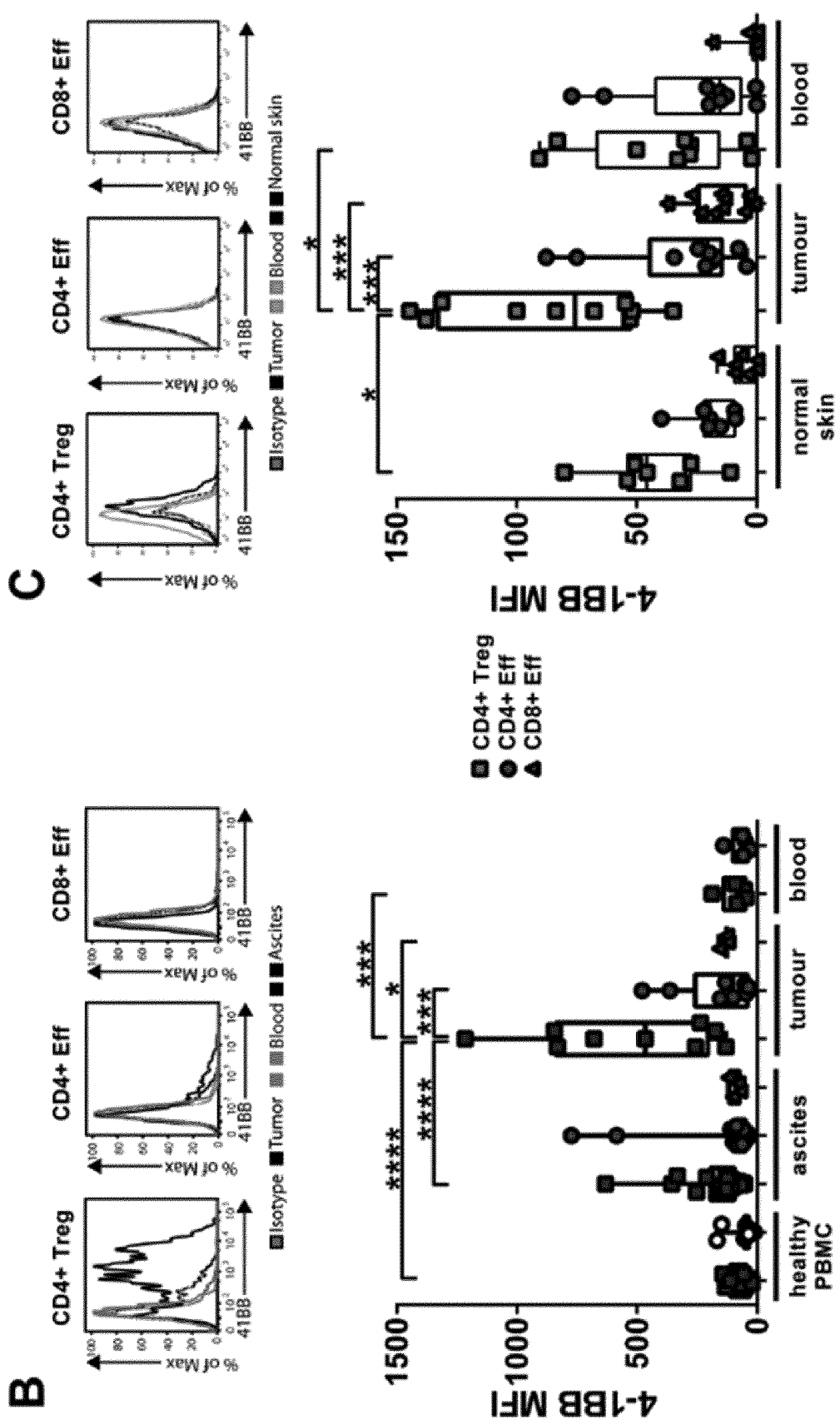
*Fig. 3, cont.*

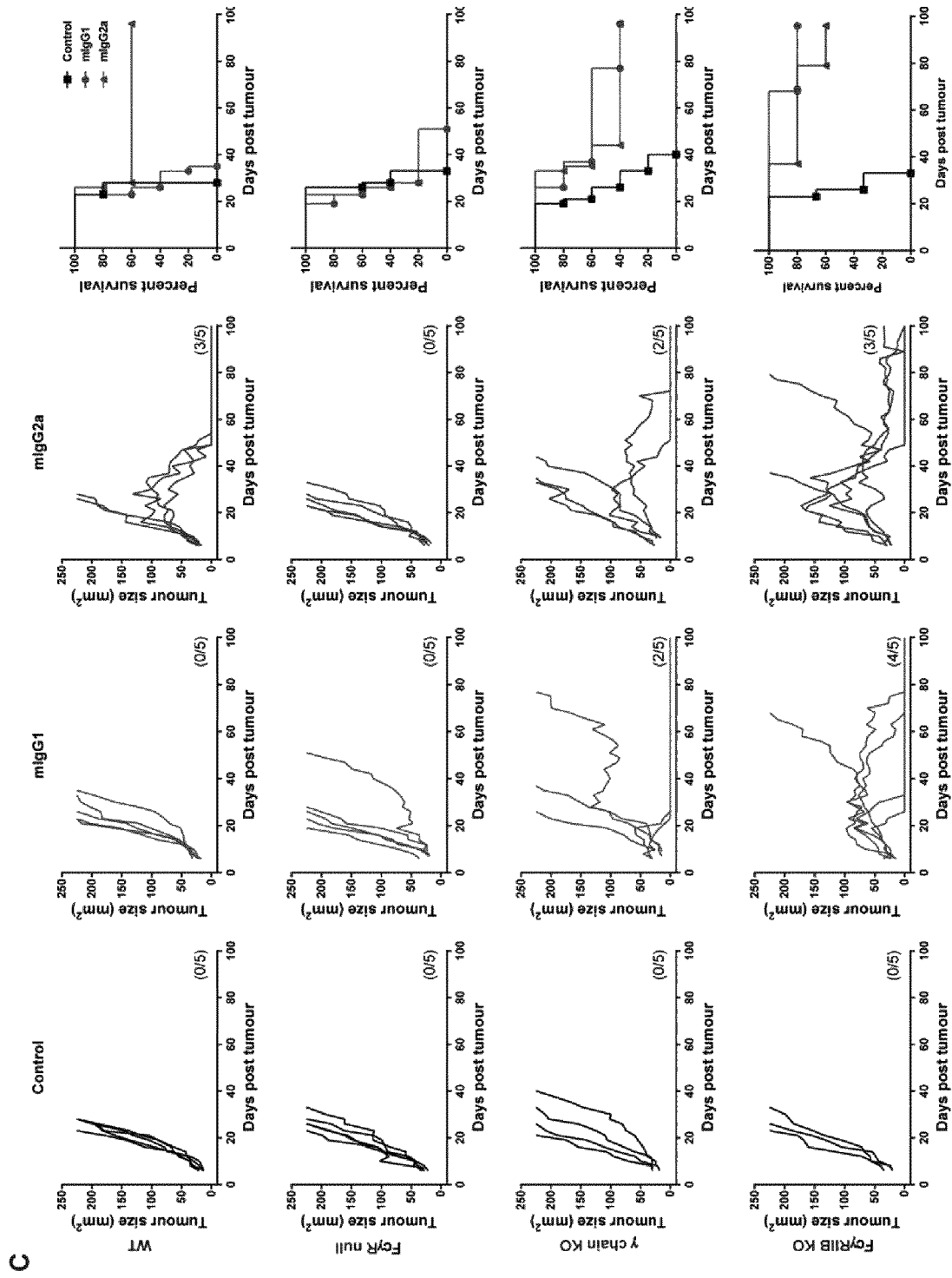
Fig. 4, cont.

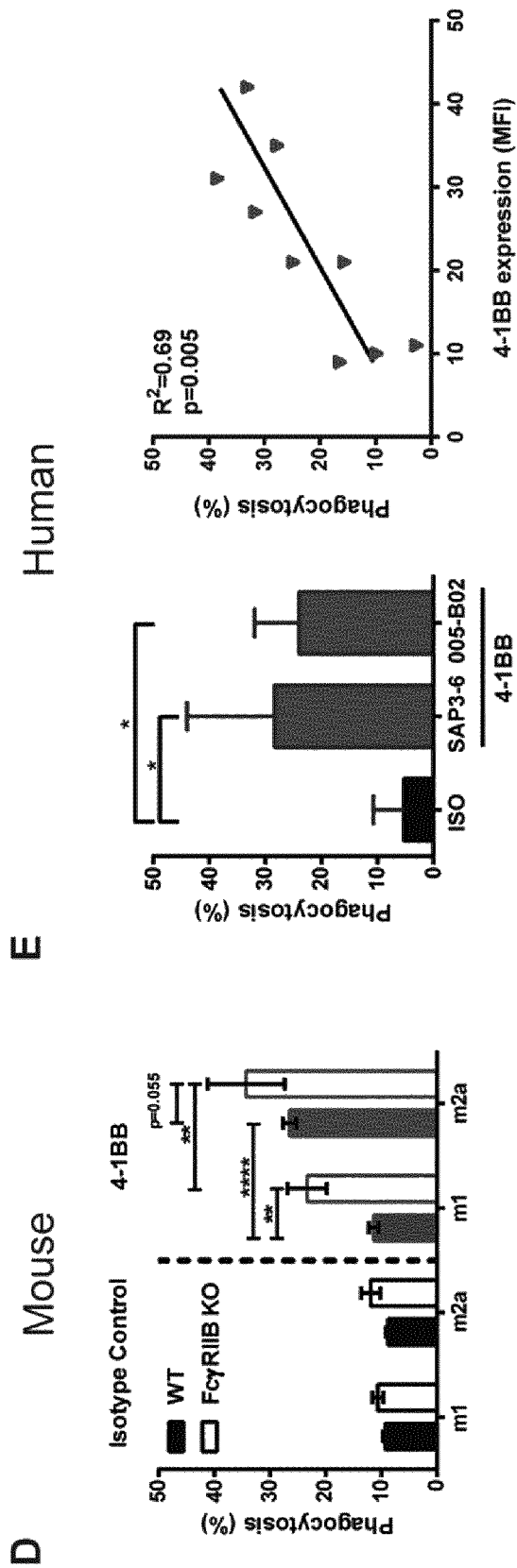
Fig. 4, cont.

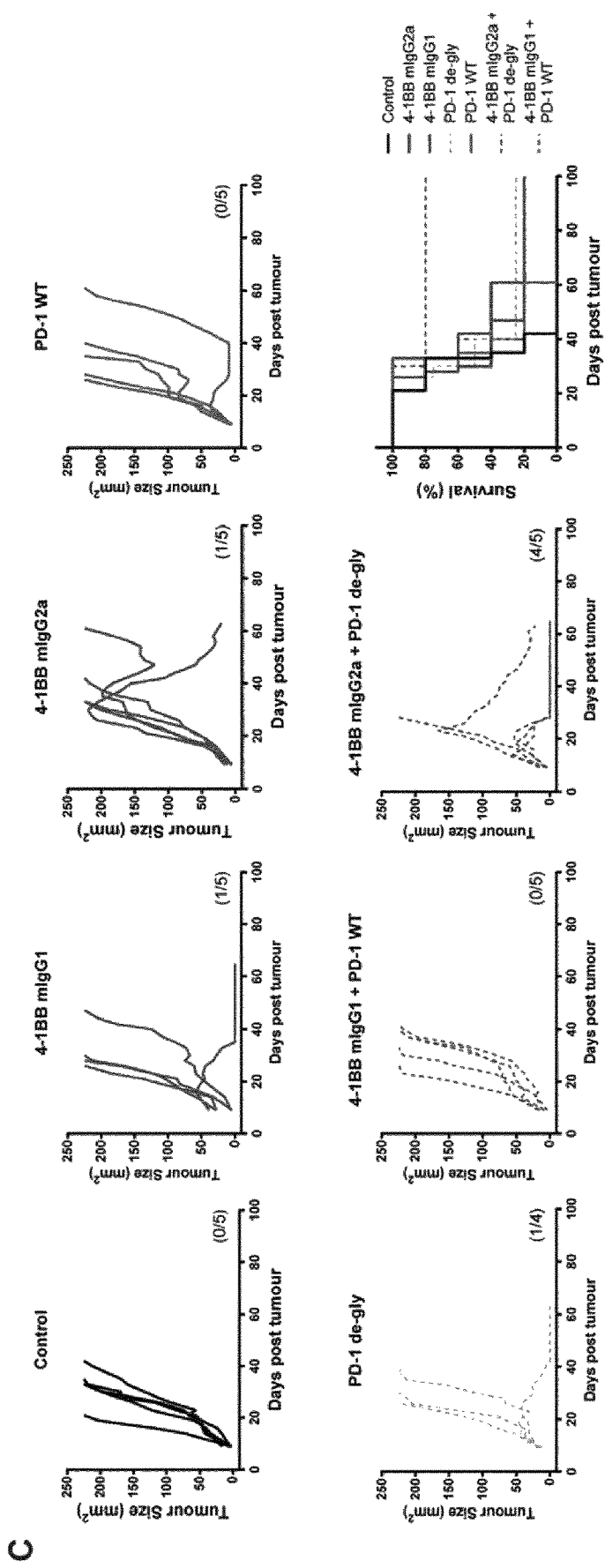
*Fig. 5, cont.*

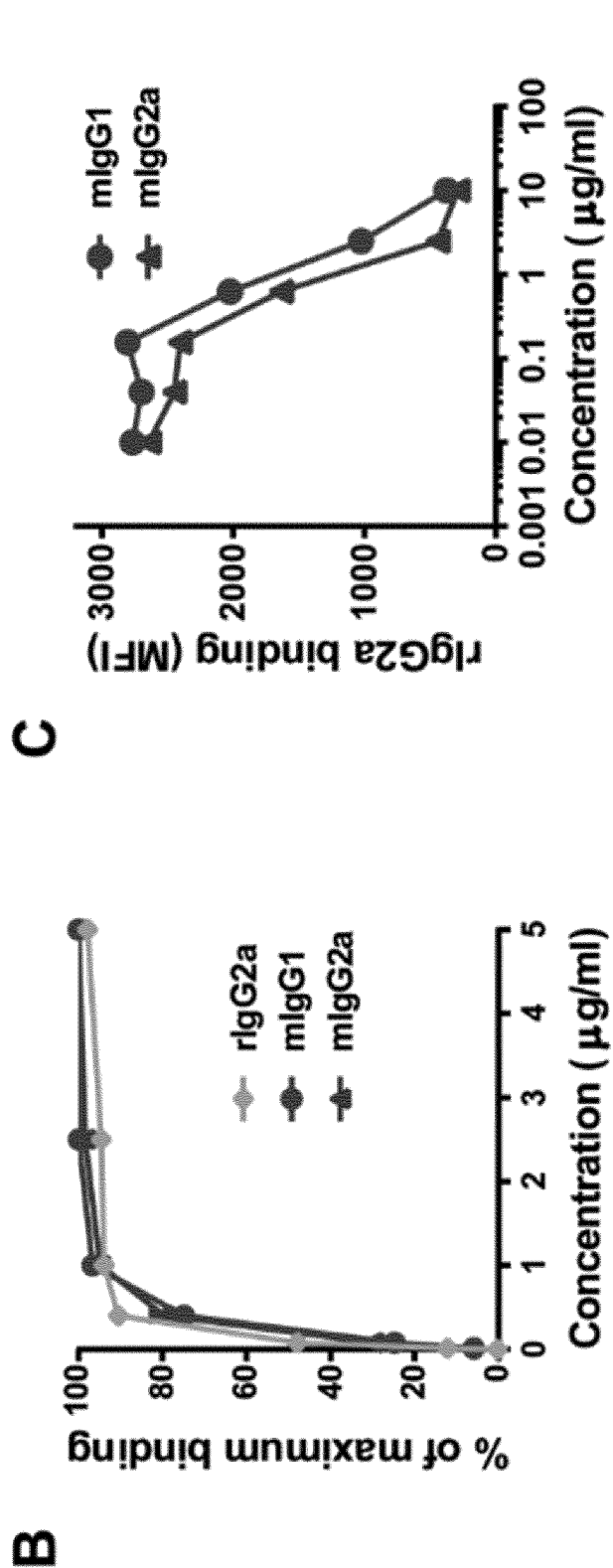
Fig. 7, cont.

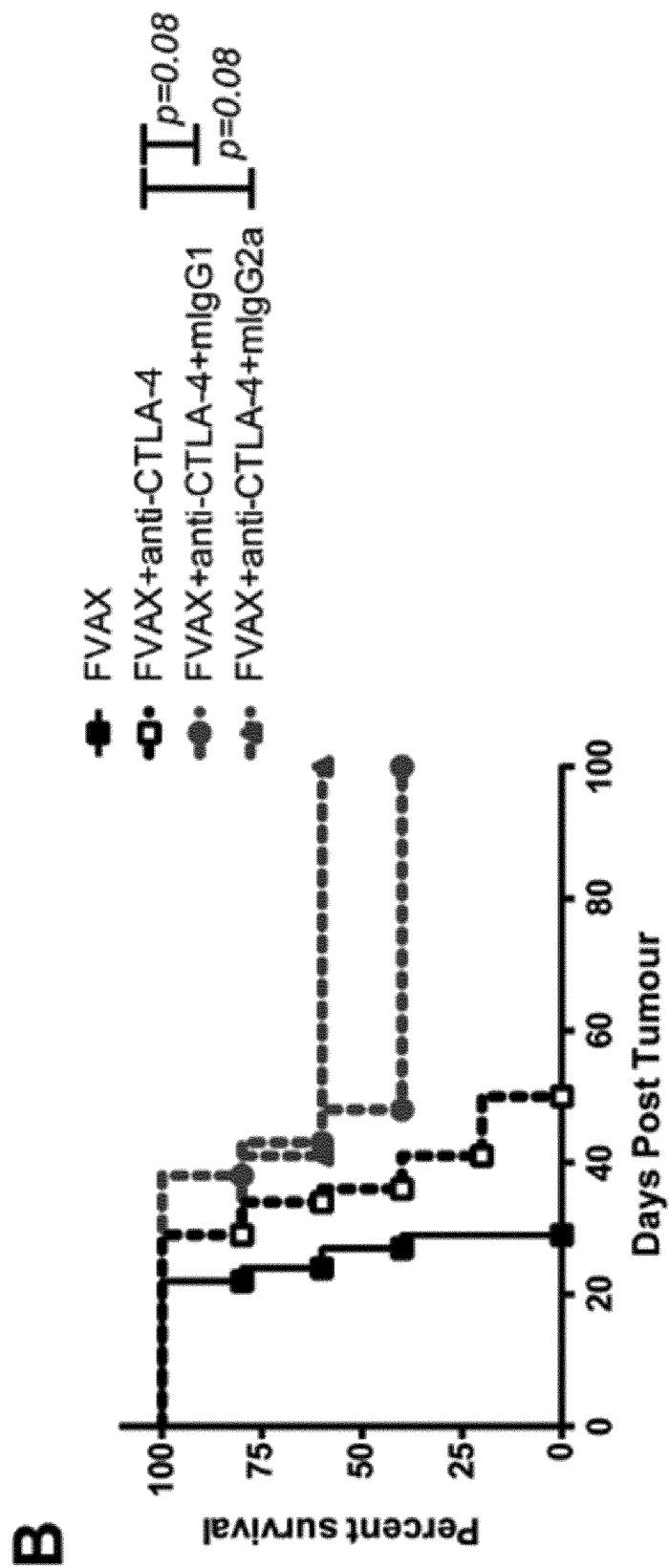
Fig. 9, cont.

Ligand Block
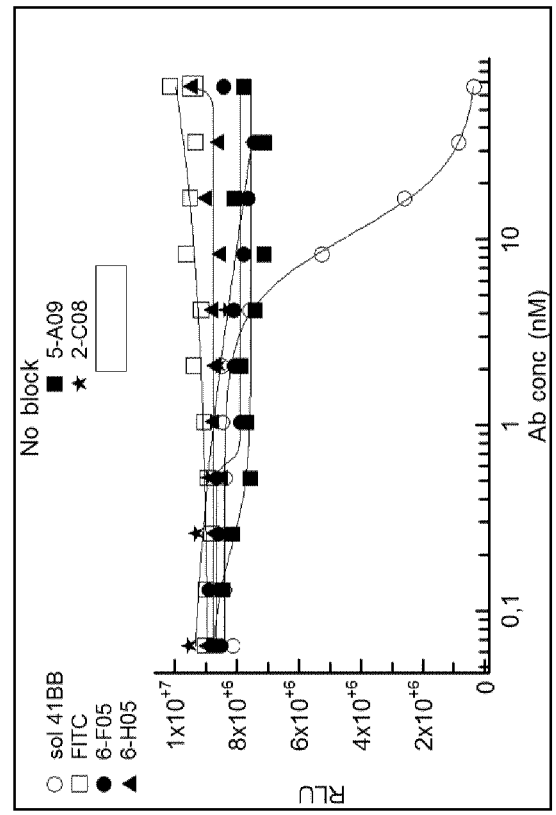
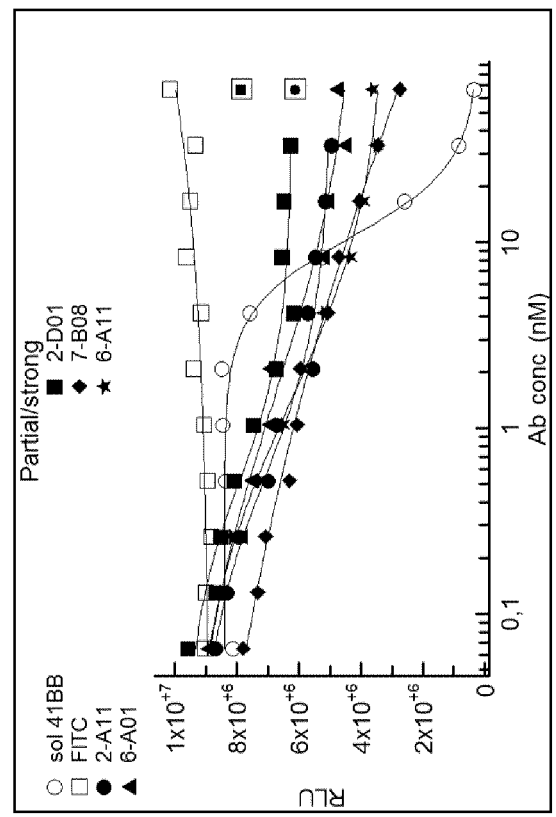
Fig. 13

Summary

| | Domain | EC50 | Off-rate | KD (M x 10⁻⁹) | ADCC | Agonistic in vitro (SOTON) | Ligand inhib of binding (ELISA) | Ligand inhib of binding (Biacore) | Agonistic activity in vivo |
|---|---|---|---|---|---|---|---|---|---|
| 001-D08 | 1 | 0.2 | Slow | 7.5 | 5th | ++ | Strong partial | Y | + |
| 001-G06 | 1 | 0.1 | Slow | 2.2 | 2nd | +++ | Weak partial | Y strong | +++ |
| 002-A02 | 3/4 | | Slow | 0.02 | | - | Complete | Partial | +++ |
| 002-D07 | 2 | 0.7 | Fast | 20 | 4th | ++ | No block | Partial | - |
| 002-F02 | 2 | | Fast | 2.2 | | - | Complete | Y | ++ |
| 002-F10 | 2 | 0.1 | Slow | 10 | 3rd | +++ | Complete | Y | ++ |
| 005-D11 | 3/4 | | Med | 2.8 | | | | N | +++ |
| 006-D12 | | 0.9 | | 15 | 4th | ++ | Weak/Low affinity | Y | + |
| 006-F03 | 3/4 | 0.9 | Med | 7.1 | 1st | ++ | Weak/Low affinity | N | ++ |
| 006-F04 | 3/4 | | Fast | 10 | | ++ | Weak/Low affinity | Y | ++ |
| 007-A07 | 1 | | Med | 4 | | | | Y | +++ |

SEQUENCE LISTING

```
<160> NUMBER OF SEQ ID NOS: 188

<210> SEQ ID NO 1
<211> LENGTH: 14
<212> TYPE: PRT
<213> ORGANISM: Homo sapiens

<400> SEQUENCE: 1

Phe Ser Ser Asn Glu Met Ser Trp Val Arg Gln Ala Pro Gly
1               5                   10

<210> SEQ ID NO 2
<211> LENGTH: 13
<212> TYPE: PRT
<213> ORGANISM: Homo sapiens

<400> SEQUENCE: 2

Ser Gly Ser Ile Gly Tyr Ala Asp Ser Val Lys Gly Arg
1               5                   10

<210> SEQ ID NO 3
<211> LENGTH: 15
<212> TYPE: PRT
<213> ORGANISM: Homo sapiens

<400> SEQUENCE: 3

Ala Arg Asp Arg Met Val Arg Gly Val Ser Asn Trp Phe Asp Pro
1               5                   10                  15

<210> SEQ ID NO 4
<211> LENGTH: 15
<212> TYPE: PRT
<213> ORGANISM: Homo sapiens

<400> SEQUENCE: 4

Cys Thr Gly Ser Ser Ser Asn Ile Gly Ala Gly Tyr Asp Val Asn
1               5                   10                  15
```

<210> SEQ ID NO 5
<211> LENGTH: 7
<212> TYPE: PRT
<213> ORGANISM: Homo sapiens

<400> SEQUENCE: 5

Gly Asn Phe Asn Arg Pro Ser
1               5

<210> SEQ ID NO 6
<211> LENGTH: 12
<212> TYPE: PRT
<213> ORGANISM: Homo sapiens

<400> SEQUENCE: 6

Cys Gln Ser Tyr Asp Ser Arg Leu Ser Gly Ser Val
1               5                   10

<210> SEQ ID NO 7
<211> LENGTH: 122
<212> TYPE: PRT
<213> ORGANISM: Homo sapiens

<400> SEQUENCE: 7

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Glu Met Ser Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Met Val Arg Gly Val Ser Asn Trp Phe Asp Pro Trp
                100                 105                 110

Gly Gln Gly Thr Leu Val Thr Val Ser Ser
            115                 120

<210> SEQ ID NO 8
<211> LENGTH: 112
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val Asn Trp Tyr Gln Gln Leu Pro Gly Thr Ala Pro Lys Leu
        35                  40                  45

Leu Ile Tyr Gly Asn Phe Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Arg 85                  90                  95

Leu Ser Gly Ser Val Phe Gly Gly Gly Thr Lys Leu Thr Val Leu Gly
                100                 105                 110

<210> SEQ ID NO 9
<211> LENGTH: 16
<212> TYPE: PRT
<213> ORGANISM: Homo sapiens

<400> SEQUENCE: 9

Phe Thr Phe Gly Asp Tyr Ala Val Ala Trp Phe Arg Gln Ala Pro Gly
1               5                   10                  15

<210> SEQ ID NO 10
<211> LENGTH: 11
<212> TYPE: PRT
<213> ORGANISM: Homo sapiens

<400> SEQUENCE: 10

Ile Thr Asp Tyr Ala Asp Pro Val Lys Gly Arg
1               5                   10

<210> SEQ ID NO 11
<211> LENGTH: 14
<212> TYPE: PRT
<213> ORGANISM: Homo sapiens

<400> SEQUENCE: 11

Ala Arg Asn Tyr Gly Gly Tyr Tyr Tyr Gly Met Asp Val
1               5                   10

<210> SEQ ID NO 12
<211> LENGTH: 15
<212> TYPE: PRT
<213> ORGANISM: Homo sapiens

<400> SEQUENCE: 12

Cys Thr Gly Ser Ser Ser Asn Ile Gly Ala Gly Tyr Asp Val His
1               5                   10                  15

<210> SEQ ID NO 13
<211> LENGTH: 16
<212> TYPE: PRT
<213> ORGANISM: Homo sapiens

<400> SEQUENCE: 13

Gly Thr Ala Pro Lys Leu Leu Ile Tyr Gly Thr Asn Asn Arg Pro Ser
1               5                   10                  15

<210> SEQ ID NO 14
<211> LENGTH: 12
<212> TYPE: PRT
<213> ORGANISM: Homo sapiens

<400> SEQUENCE: 14

Cys Ala Ala Trp Asp Gly Ser Leu Ser Gly Arg Val
1               5                   10

<210> SEQ ID NO 15
<211> LENGTH: 121
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Val Ala Trp Phe Arg Gln Ala Pro Gly Lys Gly Leu Glu Trp Val
        35                  40                  45

Ser Ile Val Ser Gly Ser Gly Thr Ile Thr Asp Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Gly Gly Tyr Tyr Tyr Gly Met Asp Val Trp Gly
            100                 105                 110

Gln Gly Thr Leu Val Thr Val Ser Ser
            115                 120

<210> SEQ ID NO 16
<211> LENGTH: 112
<212> TYPE: PRT
<213> ORGANISM: Homo sapiens

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Thr Asn Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Ser
                85                  90                  95

Leu Ser Gly Arg Val Phe Gly Gly Gly Thr Lys Leu Thr Val Leu Gly
            100                 105                 110

<210> SEQ ID NO 17
<211> LENGTH: 14
<212> TYPE: PRT
<213> ORGANISM: Homo sapiens

<400> SEQUENCE: 17

Phe Ser Ser Asn Tyr Met Ser Trp Val Arg Gln Ala Pro Gly
1               5                   10

<210> SEQ ID NO 18
<211> LENGTH: 19
<212> TYPE: PRT
<213> ORGANISM: Homo sapiens

<400> SEQUENCE: 18

Ser Ser Ile Ser Ser Gly Ser Ser Tyr Ile Tyr Tyr Ala Asp Ser Val
1               5                   10                  15

Lys Gly Arg

<210> SEQ ID NO 19

```
<211> LENGTH: 13
<212> TYPE: PRT
<213> ORGANISM: Homo sapiens

<400> SEQUENCE: 19

Ala Lys Glu Pro Pro Ala Tyr Arg Glu Gly Ile Asp Tyr
1               5                   10

<210> SEQ ID NO 20
<211> LENGTH: 14
<212> TYPE: PRT
<213> ORGANISM: Homo sapiens

<400> SEQUENCE: 20

Cys Ser Gly Ser Ser Ser Asn Ile Ala Asn Asn Tyr Val Ser
1               5                   10

<210> SEQ ID NO 21
<211> LENGTH: 7
<212> TYPE: PRT
<213> ORGANISM: Homo sapiens

<400> SEQUENCE: 21

Asp Asn Thr Asn Arg Pro Ser
1               5

<210> SEQ ID NO 22
<211> LENGTH: 12
<212> TYPE: PRT
<213> ORGANISM: Homo sapiens

<400> SEQUENCE: 22

Cys Ala Ser Trp Asp Asp Ser Leu Ser Gly Pro Val
1               5                   10

<210> SEQ ID NO 23
<211> LENGTH: 120
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Ser Gly Ser Ser Tyr Ile Tyr Tyr Ala Asp Ser Val
    50                  55                  60

Lys Gly Arg Phe Thr Ile Ser Ile Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Pro Pro Ala Tyr Arg Glu Gly Ile Asp Tyr Trp Gly Gln
            100                 105                 110

Gly Thr Leu Val Thr Val Ser Ser
        115                 120

<210> SEQ ID NO 24
<211> LENGTH: 111
<212> TYPE: PRT
<213> ORGANISM: Homo sapiens
```

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Ala Asn Asn
            20                  25                  30

Tyr Val Ser Trp Tyr Gln Gln Leu Pro Gly Thr Ala Pro Lys Leu Leu
        35                  40                  45

Ile Tyr Asp Asn Thr Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 25
<211> LENGTH: 14
<212> TYPE: PRT
<213> ORGANISM: Homo sapiens

<400> SEQUENCE: 25

Phe Ser Ser Tyr Ser Met Asn Trp Val Arg Gln Ala Pro Gly
1               5                   10

<210> SEQ ID NO 26
<211> LENGTH: 19
<212> TYPE: PRT
<213> ORGANISM: Homo sapiens

<400> SEQUENCE: 26

Ala Val Ile Ser Tyr Asp Gly Ser Asn Lys Tyr Tyr Ala Asp Ser Met
1               5                   10                  15

Lys Gly Arg

<210> SEQ ID NO 27
<211> LENGTH: 19
<212> TYPE: PRT
<213> ORGANISM: Homo sapiens

<400> SEQUENCE: 27

Ala Arg Asp Ser Tyr Leu Gly Trp Cys Pro Ala Gly Ser Cys Thr Gly
1               5                   10                  15

Ile Asp Tyr

<210> SEQ ID NO 28
<211> LENGTH: 14
<212> TYPE: PRT
<213> ORGANISM: Homo sapiens

<400> SEQUENCE: 28

Cys Ser Gly Ser Ser Asn Ile Gly Asn Asn Ala Val Asn
1               5                   10

<210> SEQ ID NO 29
<211> LENGTH: 7
<212> TYPE: PRT
<213> ORGANISM: Homo sapiens

<400> SEQUENCE: 29

```
Tyr Asp Asp Leu Leu Pro Ser
 1               5

<210> SEQ ID NO 30
<211> LENGTH: 12
<212> TYPE: PRT
<213> ORGANISM: Homo sapiens

<400> SEQUENCE: 30

Cys Ala Ala Trp Asp Asp Ser Leu Ser Gly Trp Val
 1               5                  10

<210> SEQ ID NO 31
<211> LENGTH: 126
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Met
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Ser Tyr Leu Gly Trp Cys Pro Ala Gly Ser Cys Thr Gly
            100                 105                 110

Ile Asp Tyr Trp Gly Gln Gly Thr Leu Val Thr Val Ser Ser
        115                 120                 125

<210> SEQ ID NO 32
<211> LENGTH: 111
<212> TYPE: PRT
<213> ORGANISM: Homo sapiens

<400> SEQUENCE: 32

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
            100                 105                 110

<210> SEQ ID NO 33
<211> LENGTH: 14
```

```
<212> TYPE: PRT
<213> ORGANISM: Homo sapiens

<400> SEQUENCE: 33

Phe Ser Asn Tyr Val Leu Thr Trp Val Arg Gln Ser Pro Gly
1               5                   10

<210> SEQ ID NO 34
<211> LENGTH: 16
<212> TYPE: PRT
<213> ORGANISM: Homo sapiens

<400> SEQUENCE: 34

Ser Gly Ser Gly Tyr Asn Thr Tyr His Ala Asp Ser Val Lys Gly Arg
1               5                   10                  15

<210> SEQ ID NO 35
<211> LENGTH: 16
<212> TYPE: PRT
<213> ORGANISM: Homo sapiens

<400> SEQUENCE: 35

Ala Arg Ala Ala Tyr Asp Ser Ser Gly Tyr Ala Asp Ala Phe Asp Ile
1               5                   10                  15

<210> SEQ ID NO 36
<211> LENGTH: 14
<212> TYPE: PRT
<213> ORGANISM: Homo sapiens

<400> SEQUENCE: 36

Cys Ser Gly Ser Ser Ser Asn Ile Gly Ser Asn Tyr Val Tyr
1               5                   10

<210> SEQ ID NO 37
<211> LENGTH: 7
<212> TYPE: PRT
<213> ORGANISM: Homo sapiens

<400> SEQUENCE: 37

Gly Asp Asn Arg Arg Pro Ser
1               5

<210> SEQ ID NO 38
<211> LENGTH: 12
<212> TYPE: PRT
<213> ORGANISM: Homo sapiens

<400> SEQUENCE: 38

Cys Ala Ala Trp Asp Asp Ser Leu Asn Gly Trp Val
1               5                   10

<210> SEQ ID NO 39
<211> LENGTH: 123
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Leu Thr Trp Val Arg Gln Ser Pro Gly Lys Gly Leu Glu Trp Val
        35                  40                  45
```

Ser Gly Ile Ser Gly Ser Gly Tyr Asn Thr Tyr His Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Tyr Asp Ser Ser Gly Tyr Ala Asp Ala Phe Asp Ile
            100                 105                 110

Trp Gly Gln Gly Thr Leu Val Thr Val Ser Ser
            115                 120

<210> SEQ ID NO 40
<211> LENGTH: 111
<212> TYPE: PRT
<213> ORGANISM: Homo sapiens

<400> SEQUENCE: 40

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Tyr Val Tyr Trp Tyr Gln Gln Leu Pro Gly Thr Ala Pro Lys Leu Leu
         35                  40                  45

Ile Tyr Gly Asp Asn Arg Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu Gly
            100                 105                 110

<210> SEQ ID NO 41
<211> LENGTH: 24
<212> TYPE: PRT
<213> ORGANISM: Homo sapiens

<400> SEQUENCE: 41

Arg Leu Ser Cys Ala Ala Ser Gly Phe Thr Phe Ser Asp Tyr Tyr Met
 1               5                  10                  15

Ser Trp Val Arg Gln Ala Pro Gly
             20

<210> SEQ ID NO 42
<211> LENGTH: 19
<212> TYPE: PRT
<213> ORGANISM: Homo sapiens

<400> SEQUENCE: 42

Ala Asn Ile Lys Gln Asp Gly Ser Glu Lys Tyr Tyr Gly Asp Ser Ala
 1               5                  10                  15

Thr Gly Arg

<210> SEQ ID NO 43
<211> LENGTH: 11
<212> TYPE: PRT
<213> ORGANISM: Homo sapiens

<400> SEQUENCE: 43

Ala Lys Glu Glu Arg Ile Gly Thr Tyr Tyr Tyr
1               5                   10

<210> SEQ ID NO 44
<211> LENGTH: 14
<212> TYPE: PRT
<213> ORGANISM: Homo sapiens

<400> SEQUENCE: 44

Cys Ser Gly Ser Ser Phe Asn Ile Gly Ser Asn Tyr Val Tyr
1               5                   10

<210> SEQ ID NO 45
<211> LENGTH: 7
<212> TYPE: PRT
<213> ORGANISM: Homo sapiens

<400> SEQUENCE: 45

Lys Asn Asn Gln Arg Pro Ser
1               5

<210> SEQ ID NO 46
<211> LENGTH: 12
<212> TYPE: PRT
<213> ORGANISM: Homo sapiens

<400> SEQUENCE: 46

Cys Ala Ala Trp Asp Asp Ser Leu Asn Gly Gln Val
1               5                   10

<210> SEQ ID NO 47
<211> LENGTH: 118
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Gly Asp Ser Ala
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Arg Ile Gly Thr Tyr Tyr Tyr Trp Gly Gln Gly Thr
            100                 105                 110

Leu Val Thr Val Ser Ser
        115

<210> SEQ ID NO 48
<211> LENGTH: 111
<212> TYPE: PRT
<213> ORGANISM: Homo sapiens

<400> SEQUENCE: 48

Gln Ser Val Leu Thr Gln Pro Pro Ser Ala Ser Gly Thr Pro Gly Gln
1               5                   10                  15

-continued

```
Arg Val Thr Ile Ser Cys Ser Gly Ser Ser Phe Asn Ile Gly Ser Asn
             20                  25                  30

Tyr Val Tyr Trp Tyr Gln Gln Leu Pro Gly Thr Ala Pro Lys Leu Leu
         35                  40                  45

Ile Tyr Lys Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Gln Val Phe Gly Gly Gly Thr Lys Leu Thr Val Leu Gly
            100                 105                 110

<210> SEQ ID NO 49
<211> LENGTH: 14
<212> TYPE: PRT
<213> ORGANISM: Homo sapiens

<400> SEQUENCE: 49

Phe Ser Asp Tyr Tyr Met Thr Trp Ile Arg Gln Ala Pro Gly
1               5                   10

<210> SEQ ID NO 50
<211> LENGTH: 19
<212> TYPE: PRT
<213> ORGANISM: Homo sapiens

<400> SEQUENCE: 50

Ser Ser Ile Ser Ser Ser Ser Tyr Ile Tyr Tyr Ala Asp Ser Val
1               5                   10                  15

Lys Gly Arg

<210> SEQ ID NO 51
<211> LENGTH: 22
<212> TYPE: PRT
<213> ORGANISM: Homo sapiens

<400> SEQUENCE: 51

Ala Ser Thr Gln Thr Pro Tyr Gly Ser Gly Asn Tyr Pro Ile Tyr Tyr
1               5                   10                  15

Tyr Tyr Gly Met Asp Val
            20

<210> SEQ ID NO 52
<211> LENGTH: 14
<212> TYPE: PRT
<213> ORGANISM: Homo sapiens

<400> SEQUENCE: 52

Cys Ser Gly Ser Arg Ser Asn Ile Arg Ser Asn Ser Val Ser
1               5                   10

<210> SEQ ID NO 53
<211> LENGTH: 7
<212> TYPE: PRT
<213> ORGANISM: Homo sapiens

<400> SEQUENCE: 53

Gly Asn Ser Asn Arg Pro Ser
1               5
```

<210> SEQ ID NO 54
<211> LENGTH: 12
<212> TYPE: PRT
<213> ORGANISM: Homo sapiens

<400> SEQUENCE: 54

Cys Gly Thr Trp Asp Asp Arg Leu Asn Arg Pro Val
1               5                   10

<210> SEQ ID NO 55
<211> LENGTH: 129
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Thr Gln Thr Pro Tyr Gly Ser Gly Asn Tyr Pro Ile Tyr Tyr
            100                 105                 110

Tyr Tyr Gly Met Asp Val Trp Gly Gln Gly Thr Leu Val Thr Val Ser
        115                 120                 125

Ser

<210> SEQ ID NO 56
<211> LENGTH: 111
<212> TYPE: PRT
<213> ORGANISM: Homo sapiens

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Arg Ser Asn
            20                  25                  30

Ser Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Arg Leu
                85                  90                  95

Asn Arg Pro Val Phe Gly Gly Gly Thr Lys Leu Thr Val Leu Gly
            100                 105                 110

<210> SEQ ID NO 57
<211> LENGTH: 14
<212> TYPE: PRT
<213> ORGANISM: Homo sapiens

<400> SEQUENCE: 57

Phe Ser Ser Tyr Trp Met Ser Trp Val Arg Gln Thr Pro Gly
1               5                   10

<210> SEQ ID NO 58
<211> LENGTH: 19
<212> TYPE: PRT
<213> ORGANISM: Homo sapiens

<400> SEQUENCE: 58

Ser Ala Ile Asn Ala Ala Gly Asp Phe Gln Ser Tyr Ala Asp Ser Val
1               5                   10                  15

Arg Gly Arg

<210> SEQ ID NO 59
<211> LENGTH: 11
<212> TYPE: PRT
<213> ORGANISM: Homo sapiens

<400> SEQUENCE: 59

Ala Arg Gly Asp Gly Tyr Asn Tyr Phe Asp Ile
1               5                   10

<210> SEQ ID NO 60
<211> LENGTH: 14
<212> TYPE: PRT
<213> ORGANISM: Homo sapiens

<400> SEQUENCE: 60

Cys Ser Gly Ser Ser Asn Ile Gly Ser Asn Tyr Val Tyr
1               5                   10

<210> SEQ ID NO 61
<211> LENGTH: 7
<212> TYPE: PRT
<213> ORGANISM: Homo sapiens

<400> SEQUENCE: 61

Gly Asn Ser Asn Arg Pro Ser
1               5

<210> SEQ ID NO 62
<211> LENGTH: 12
<212> TYPE: PRT
<213> ORGANISM: Homo sapiens

<400> SEQUENCE: 62

Cys Gln Ser Tyr Asp Ser Ser Leu Ser Gly Leu Val
1               5                   10

<210> SEQ ID NO 63
<211> LENGTH: 118
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Thr Pro Gly Lys Gly Leu Glu Trp Val
            35                  40                  45

Ser Ala Ile Asn Ala Ala Gly Asp Phe Gln Ser Tyr Ala Asp Ser Val
            50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                85                  90                  95

Ala Arg Gly Asp Gly Tyr Asn Tyr Phe Asp Ile Trp Gly Gln Gly Thr
            100                 105                 110

Leu Val Thr Val Ser Ser
            115

<210> SEQ ID NO 64
<211> LENGTH: 111
<212> TYPE: PRT
<213> ORGANISM: Homo sapiens

<400> SEQUENCE: 64

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Gly Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Ser Ser Leu
                85                  90                  95

Ser Gly Leu Val Phe Gly Gly Gly Thr Lys Leu Thr Val Leu Gly
            100                 105                 110

<210> SEQ ID NO 65
<211> LENGTH: 14
<212> TYPE: PRT
<213> ORGANISM: Homo sapiens

<400> SEQUENCE: 65

Phe Ser Arg Tyr Glu Met Asn Trp Val Arg Gln Ala Pro Gly
 1               5                  10

<210> SEQ ID NO 66
<211> LENGTH: 19
<212> TYPE: PRT
<213> ORGANISM: Homo sapiens

<400> SEQUENCE: 66

Ser Gly Ile Asn Trp Asn Gly Gly Ser Thr Gly Tyr Ala Asp Ser Val
 1               5                  10                  15

Lys Gly Arg

<210> SEQ ID NO 67
<211> LENGTH: 14
<212> TYPE: PRT
<213> ORGANISM: Homo sapiens

<400> SEQUENCE: 67

Ala Arg His Arg Asn Pro Asp Pro Leu Asp Ala Phe Asp Ile
 1               5                  10

<210> SEQ ID NO 68
<211> LENGTH: 15
<212> TYPE: PRT
<213> ORGANISM: Homo sapiens

<400> SEQUENCE: 68

Cys Thr Gly Ser Ser Ser Asn Ile Gly Ala Gly Tyr Asp Val His
1               5                   10                  15

<210> SEQ ID NO 69
<211> LENGTH: 7
<212> TYPE: PRT
<213> ORGANISM: Homo sapiens

<400> SEQUENCE: 69

Ser Asn Asn Gln Arg Pro Ser
1               5

<210> SEQ ID NO 70
<211> LENGTH: 11
<212> TYPE: PRT
<213> ORGANISM: Homo sapiens

<400> SEQUENCE: 70

Cys Ala Ser Tyr Thr Ser Ile Ser Thr Val Leu
1               5                   10

<210> SEQ ID NO 71
<211> LENGTH: 121
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Glu Met Asn Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Arg Asn Pro Asp Pro Leu Asp Ala Phe Asp Ile Trp Gly
            100                 105                 110

Gln Gly Thr Leu Val Thr Val Ser Ser
        115                 120

<210> SEQ ID NO 72
<211> LENGTH: 111
<212> TYPE: PRT
<213> ORGANISM: Homo sapiens

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

-continued

```
Tyr Asp Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ser Tyr Thr Ser Ile
                 85                  90                  95

Ser Thr Val Leu Phe Gly Gly Gly Thr Lys Leu Thr Val Leu Gly
                100                 105                 110
```

<210> SEQ ID NO 73
<211> LENGTH: 14
<212> TYPE: PRT
<213> ORGANISM: Homo sapiens

<400> SEQUENCE: 73

```
Phe Ser Ser Tyr Ala Met Ser Trp Val Arg Gln Ala Pro Gly
 1               5                  10
```

<210> SEQ ID NO 74
<211> LENGTH: 19
<212> TYPE: PRT
<213> ORGANISM: Homo sapiens

<400> SEQUENCE: 74

```
Ser Gly Ile Asn Gly Tyr Gly Asp Thr Pro Lys Asp Ala Asp Ser Val
 1               5                  10                  15

Lys Gly Arg
```

<210> SEQ ID NO 75
<211> LENGTH: 14
<212> TYPE: PRT
<213> ORGANISM: Homo sapiens

<400> SEQUENCE: 75

```
Ala Thr Leu Tyr Cys Gly Gly Gly Gly Cys Tyr Pro Asp Ser
 1               5                  10
```

<210> SEQ ID NO 76
<211> LENGTH: 15
<212> TYPE: PRT
<213> ORGANISM: Homo sapiens

<400> SEQUENCE: 76

```
Cys Thr Gly Ser Arg Ser Asn Ile Gly Ala Gly Tyr Asp Val His
 1               5                  10                  15
```

<210> SEQ ID NO 77
<211> LENGTH: 7
<212> TYPE: PRT
<213> ORGANISM: Homo sapiens

<400> SEQUENCE: 77

```
Asp Tyr Asp Glu Gln Pro Ser
 1               5
```

<210> SEQ ID NO 78
<211> LENGTH: 12
<212> TYPE: PRT
<213> ORGANISM: Homo sapiens

<400> SEQUENCE: 78

Cys Ala Ala Trp Asp Asp Ser Leu Asn Gly Val Val
1               5                   10

<210> SEQ ID NO 79
<211> LENGTH: 121
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Asn Gly Tyr Gly Asp Thr Pro Lys Asp Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Tyr Cys Gly Gly Gly Cys Tyr Pro Asp Ser Trp Gly
            100                 105                 110

Gln Gly Thr Leu Val Thr Val Ser Ser
        115                 120

<210> SEQ ID NO 80
<211> LENGTH: 112
<212> TYPE: PRT
<213> ORGANISM: Homo sapiens

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Thr Gly Ser Arg Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Tyr Asp Glu Gln Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Val Val Phe Gly Gly Gly Thr Lys Leu Thr Val Leu Gly
            100                 105                 110

<210> SEQ ID NO 81
<211> LENGTH: 14
<212> TYPE: PRT
<213> ORGANISM: Homo sapiens

<400> SEQUENCE: 81

Phe Ser Gly Tyr Trp Met Thr Trp Val Arg Gln Ala Pro Gly
1               5                   10

<210> SEQ ID NO 82

```
<211> LENGTH: 19
<212> TYPE: PRT
<213> ORGANISM: Homo sapiens

<400> SEQUENCE: 82

Ser Ser Ile Ser Ser Ser Ser Tyr Ile Tyr Tyr Ala Asp Ser Val
1               5                   10                  15

Lys Gly Arg

<210> SEQ ID NO 83
<211> LENGTH: 11
<212> TYPE: PRT
<213> ORGANISM: Homo sapiens

<400> SEQUENCE: 83

Thr Ser Ser Asn Pro Phe Tyr Gly Met Asp Val
1               5                   10

<210> SEQ ID NO 84
<211> LENGTH: 14
<212> TYPE: PRT
<213> ORGANISM: Homo sapiens

<400> SEQUENCE: 84

Cys Ser Gly Ser Ser Ser Asn Ile Gly Asn Asn Tyr Val Ser
1               5                   10

<210> SEQ ID NO 85
<211> LENGTH: 7
<212> TYPE: PRT
<213> ORGANISM: Homo sapiens

<400> SEQUENCE: 85

Tyr Asp Asp Leu Leu Pro Ser
1               5

<210> SEQ ID NO 86
<211> LENGTH: 12
<212> TYPE: PRT
<213> ORGANISM: Homo sapiens

<400> SEQUENCE: 86

Cys Ala Ala Trp Asp Asp Ser Leu Asn Gly Gly Val
1               5                   10

<210> SEQ ID NO 87
<211> LENGTH: 118
<212> TYPE: PRT
<213> ORGANISM: Homo sapiens

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met Thr Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95

Thr Ser Ser Asn Pro Phe Tyr Gly Met Asp Val Trp Gly Gln Gly Thr
                100                 105                 110

Leu Val Thr Val Ser Ser
            115

<210> SEQ ID NO 88
<211> LENGTH: 111
<212> TYPE: PRT
<213> ORGANISM: Homo sapiens

<400> SEQUENCE: 88

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Gly Val Phe Gly Gly Gly Thr Lys Leu Thr Val Leu Gly
                100                 105                 110

<210> SEQ ID NO 89
<211> LENGTH: 14
<212> TYPE: PRT
<213> ORGANISM: Homo sapiens

<400> SEQUENCE: 89

Phe Ser Asp Tyr Tyr Met Ser Trp Val Arg Gln Ala Pro Gly
1               5                   10

<210> SEQ ID NO 90
<211> LENGTH: 19
<212> TYPE: PRT
<213> ORGANISM: Homo sapiens

<400> SEQUENCE: 90

Ser Ser Ile Thr Gly Thr Ala Gly Leu Thr Tyr Asn Ala Asp Ser Val
1               5                   10                  15

Lys Gly Arg

<210> SEQ ID NO 91
<211> LENGTH: 12
<212> TYPE: PRT
<213> ORGANISM: Homo sapiens

<400> SEQUENCE: 91

Ala Arg Met Asp Trp Gly Tyr Gly Asn Phe Asp Tyr
1               5                   10

<210> SEQ ID NO 92
<211> LENGTH: 14
<212> TYPE: PRT
<213> ORGANISM: Homo sapiens

<400> SEQUENCE: 92
```

```
Cys Ser Gly Ser Ser Ser Asn Ile Gly Ser Tyr Thr Val Asn
1               5                   10
```

<210> SEQ ID NO 93
<211> LENGTH: 7
<212> TYPE: PRT
<213> ORGANISM: Homo sapiens

<400> SEQUENCE: 93

```
Gly Asn Asn Asn Arg Pro Ser
1               5
```

<210> SEQ ID NO 94
<211> LENGTH: 12
<212> TYPE: PRT
<213> ORGANISM: Homo sapiens

<400> SEQUENCE: 94

```
Cys Ala Thr Trp Asp Asp Ser Leu Ser Gly Pro Val
1               5                   10
```

<210> SEQ ID NO 95
<211> LENGTH: 119
<212> TYPE: PRT
<213> ORGANISM: Homo sapiens

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Thr Gly Thr Ala Gly Leu Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Asp Trp Gly Tyr Gly Asn Phe Asp Tyr Trp Gly Gln Gly
            100                 105                 110

Thr Leu Val Thr Val Ser Ser
        115
```

<210> SEQ ID NO 96
<211> LENGTH: 111
<212> TYPE: PRT
<213> ORGANISM: Homo sapiens

<400> SEQUENCE: 96

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Thr Val Asn Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
```

```
                65                  70                  75                  80
Ser Glu Asp Glu Ala Asp Tyr Tyr Cys Ala Thr Trp Asp Asp Ser Leu
                    85                  90                  95

Ser Gly Pro Val Phe Gly Gly Gly Thr Lys Leu Thr Val Leu Gly
            100                 105                 110

<210> SEQ ID NO 97
<211> LENGTH: 14
<212> TYPE: PRT
<213> ORGANISM: Homo sapiens

<400> SEQUENCE: 97

Phe Ser Asp Tyr Glu Met Asn Trp Val Arg Gln Ala Pro Gly
1               5                   10

<210> SEQ ID NO 98
<211> LENGTH: 19
<212> TYPE: PRT
<213> ORGANISM: Homo sapiens

<400> SEQUENCE: 98

Ala Val Ile Ser Tyr Asp Gly Ser Asn Lys Tyr Tyr Ala Asp Ser Val
1               5                   10                  15

Lys Gly Arg

<210> SEQ ID NO 99
<211> LENGTH: 8
<212> TYPE: PRT
<213> ORGANISM: Homo sapiens

<400> SEQUENCE: 99

Ala Ala Asn Ser Pro Phe Asp Pro
1               5

<210> SEQ ID NO 100
<211> LENGTH: 15
<212> TYPE: PRT
<213> ORGANISM: Homo sapiens

<400> SEQUENCE: 100

Cys Thr Gly Ser Ser Ser Asn Ile Gly Ala Gly Tyr Asp Val His
1               5                   10                  15

<210> SEQ ID NO 101
<211> LENGTH: 7
<212> TYPE: PRT
<213> ORGANISM: Homo sapiens

<400> SEQUENCE: 101

Asn Asp Asn Val Arg Pro Ser
1               5

<210> SEQ ID NO 102
<211> LENGTH: 12
<212> TYPE: PRT
<213> ORGANISM: Homo sapiens

<400> SEQUENCE: 102

Cys Ala Ala Trp Asp Ala Asn Leu Ser Gly Trp Val
1               5                   10

<210> SEQ ID NO 103
<211> LENGTH: 115
```

```
<212> TYPE: PRT
<213> ORGANISM: Homo sapiens

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asn Ser Pro Phe Asp Pro Trp Gly Gln Gly Thr Leu Val Thr
            100                 105                 110

Val Ser Ser
        115

<210> SEQ ID NO 104
<211> LENGTH: 112
<212> TYPE: PRT
<213> ORGANISM: Homo sapiens

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asn Asp Asn Val Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Ala Asn
                85                  90                  95

Leu Ser Gly Trp Val Phe Gly Gly Gly Thr Lys Leu Thr Val Leu Gly
            100                 105                 110

<210> SEQ ID NO 105
<211> LENGTH: 14
<212> TYPE: PRT
<213> ORGANISM: Homo sapiens

<400> SEQUENCE: 105

Phe Ser Ser Tyr Glu Met Asn Trp Val Arg Gln Ala Pro Gly
1               5                   10

<210> SEQ ID NO 106
<211> LENGTH: 19
<212> TYPE: PRT
<213> ORGANISM: Homo sapiens

<400> SEQUENCE: 106

Ala Val Ile Ser Tyr Asp Gly Ser Asn Lys Tyr Tyr Ala Asp Ser Val
1               5                   10                  15
```

Lys Gly Arg

<210> SEQ ID NO 107
<211> LENGTH: 8
<212> TYPE: PRT
<213> ORGANISM: Homo sapiens

<400> SEQUENCE: 107

Ala Ala Asn Ser Pro Phe Asp Pro
1               5

<210> SEQ ID NO 108
<211> LENGTH: 15
<212> TYPE: PRT
<213> ORGANISM: Homo sapiens

<400> SEQUENCE: 108

Cys Thr Gly Ser Ser Ser Asn Ile Gly Ala Gly Tyr Asp Val His
1               5                   10                  15

<210> SEQ ID NO 109
<211> LENGTH: 7
<212> TYPE: PRT
<213> ORGANISM: Homo sapiens

<400> SEQUENCE: 109

Ser Asn Asn Gln Arg Pro Ser
1               5

<210> SEQ ID NO 110
<211> LENGTH: 12
<212> TYPE: PRT
<213> ORGANISM: Homo sapiens

<400> SEQUENCE: 110

Cys Ala Ala Trp Asp Asp Ser Leu Ser Gly Trp Val
1               5                   10

<210> SEQ ID NO 111
<211> LENGTH: 115
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ala Asn Ser Pro Phe Asp Pro Trp Gly Gln Gly Thr Leu Val Thr
            100                 105                 110

Val Ser Ser
        115

<210> SEQ ID NO 112
<211> LENGTH: 112
<212> TYPE: PRT
<213> ORGANISM: Homo sapiens

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Phe Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Ser
                85                  90                  95

Leu Ser Gly Trp Val Phe Gly Gly Gly Thr Lys Leu Thr Val Leu Gly
            100                 105                 110

<210> SEQ ID NO 113
<211> LENGTH: 14
<212> TYPE: PRT
<213> ORGANISM: Homo sapiens

<400> SEQUENCE: 113

Phe Asp Asn His Trp Met Ser Trp Val Arg Gln Ala Pro Gly
1               5                   10

<210> SEQ ID NO 114
<211> LENGTH: 19
<212> TYPE: PRT
<213> ORGANISM: Homo sapiens

<400> SEQUENCE: 114

Ser Ser Ile Ser Ser Ser Ser Tyr Ile Tyr Tyr Ala Asp Ser Val
1               5                   10                  15

Lys Gly Arg

<210> SEQ ID NO 115
<211> LENGTH: 9
<212> TYPE: PRT
<213> ORGANISM: Homo sapiens

<400> SEQUENCE: 115

Ala Arg Glu Asp Trp Ser Phe Asp Leu
1               5

<210> SEQ ID NO 116
<211> LENGTH: 14
<212> TYPE: PRT
<213> ORGANISM: Homo sapiens

<400> SEQUENCE: 116

Cys Ser Gly Ser Ser Ser Asn Ile Gly Asn Asn Ala Val Asn
1               5                   10

<210> SEQ ID NO 117
<211> LENGTH: 7
<212> TYPE: PRT

<213> ORGANISM: Homo sapiens

<400> SEQUENCE: 117

Gly Asn Ser Asn Arg Pro Ser
1               5

<210> SEQ ID NO 118
<211> LENGTH: 12
<212> TYPE: PRT
<213> ORGANISM: Homo sapiens

<400> SEQUENCE: 118

Cys Gln Thr Phe Asp Val Ser Gln Asn Ala Trp Val
1               5                   10

<210> SEQ ID NO 119
<211> LENGTH: 116
<212> TYPE: PRT
<213> ORGANISM: Homo sapiens

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn His
            20                  25                  30

Trp Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Asp Trp Ser Phe Asp Leu Trp Gly Gln Gly Thr Leu Val
            100                 105                 110

Thr Val Ser Ser
        115

<210> SEQ ID NO 120
<211> LENGTH: 111
<212> TYPE: PRT
<213> ORGANISM: Homo sapiens

<400> SEQUENCE: 120

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Thr Phe Asp Val Ser Gln
                85                  90                  95

Asn Ala Trp Val Phe Gly Gly Gly Thr Lys Leu Thr Val Leu Gly
            100                 105                 110

<210> SEQ ID NO 121
<211> LENGTH: 14
<212> TYPE: PRT
<213> ORGANISM: Homo sapiens

<400> SEQUENCE: 121

Phe Ser Asn Ser Asp Met Asn Trp Val Arg Gln Ala Pro Gly
1               5                   10

<210> SEQ ID NO 122
<211> LENGTH: 19
<212> TYPE: PRT
<213> ORGANISM: Homo sapiens

<400> SEQUENCE: 122

Ser Ala Ile Ser Asn Ser Gly Asp Gly Thr Tyr Tyr Ala Asp Ser Val
1               5                   10                  15

Lys Gly Arg

<210> SEQ ID NO 123
<211> LENGTH: 11
<212> TYPE: PRT
<213> ORGANISM: Homo sapiens

<400> SEQUENCE: 123

Arg Glu Lys Thr Trp Gly Ala Ala Phe Asp Ile
1               5                   10

<210> SEQ ID NO 124
<211> LENGTH: 15
<212> TYPE: PRT
<213> ORGANISM: Homo sapiens

<400> SEQUENCE: 124

Cys Thr Gly Ser Ser Ser Asn Ile Gly Ala Gly Tyr Asp Val His
1               5                   10                  15

<210> SEQ ID NO 125
<211> LENGTH: 7
<212> TYPE: PRT
<213> ORGANISM: Homo sapiens

<400> SEQUENCE: 125

Ser Gln Asn Leu Arg Pro Ser
1               5

<210> SEQ ID NO 126
<211> LENGTH: 12
<212> TYPE: PRT
<213> ORGANISM: Homo sapiens

<400> SEQUENCE: 126

Cys Gln Ser Tyr Asp Ser Ser Leu Ser Gly Ser Val
1               5                   10

<210> SEQ ID NO 127
<211> LENGTH: 119
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Ala Ile Ser Asn Ser Gly Asp Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Thr Trp Gly Ala Ala Phe Asp Ile Trp Gly Gln Gly
            100                 105                 110

Thr Leu Val Thr Val Ser Ser
            115

<210> SEQ ID NO 128
<211> LENGTH: 112
<212> TYPE: PRT
<213> ORGANISM: Homo sapiens

<400> SEQUENCE: 128

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Gln Asn Leu Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

<210> SEQ ID NO 129
<211> LENGTH: 14
<212> TYPE: PRT
<213> ORGANISM: Homo sapiens

<400> SEQUENCE: 129

Phe Ser Asp Tyr Thr Met Asn Trp Val Arg Gln Ala Pro Gly
1               5                   10

<210> SEQ ID NO 130
<211> LENGTH: 19
<212> TYPE: PRT
<213> ORGANISM: Homo sapiens

<400> SEQUENCE: 130

Ser Ala Ile Ser Gly Ser Gly Gly Ser Thr Tyr Tyr Pro Asp Ser Val
1               5                   10                  15

Lys Gly Arg

<210> SEQ ID NO 131
<211> LENGTH: 11
<212> TYPE: PRT
<213> ORGANISM: Homo sapiens

<400> SEQUENCE: 131

Ala Arg Gly Gly Gly Tyr Trp Pro Phe Asp Pro
1               5                   10

<210> SEQ ID NO 132
<211> LENGTH: 14
<212> TYPE: PRT
<213> ORGANISM: Homo sapiens

<400> SEQUENCE: 132

Cys Ser Gly Ser Ser Ser Thr Ile Gly Asn Asn Ala Ile Asn
1               5                   10

<210> SEQ ID NO 133
<211> LENGTH: 7
<212> TYPE: PRT
<213> ORGANISM: Homo sapiens

<400> SEQUENCE: 133

Arg Asp Asn Gln Arg Pro Ser
1               5

<210> SEQ ID NO 134
<211> LENGTH: 12
<212> TYPE: PRT
<213> ORGANISM: Homo sapiens

<400> SEQUENCE: 134

Cys Gln Ser Tyr Asp Ser Ser Leu Arg Val Val Val
1               5                   10

<210> SEQ ID NO 135
<211> LENGTH: 118
<212> TYPE: PRT
<213> ORGANISM: Homo sapiens

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Tyr Trp Pro Phe Asp Pro Trp Gly Gln Gly Thr
            100                 105                 110

Leu Val Thr Val Ser Ser
        115

<210> SEQ ID NO 136
<211> LENGTH: 111
<212> TYPE: PRT
<213> ORGANISM: Homo sapiens

<400> SEQUENCE: 136

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Thr Ile Gly Asn Asn
            20                  25                  30

Ala Ile Asn Trp Tyr Gln Gln Leu Pro Gly Thr Ala Pro Lys Leu Leu
        35                  40                  45

Ile Tyr Arg Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Arg Val Val Val Phe Gly Gly Gly Thr Lys Leu Thr Val Leu Gly
            100                 105                 110
```

<210> SEQ ID NO 137
<211> LENGTH: 14
<212> TYPE: PRT
<213> ORGANISM: Homo sapiens

<400> SEQUENCE: 137

```
Phe Ser Ser Tyr Ala Met Ser Trp Val Arg Gln Ala Pro Gly
1               5                   10
```

<210> SEQ ID NO 138
<211> LENGTH: 19
<212> TYPE: PRT
<213> ORGANISM: Homo sapiens

<400> SEQUENCE: 138

```
Ser Ser Ile Ser Ser Ser Ser Tyr Ile Tyr Tyr Ala Asp Ser Val
1               5                   10                  15

Lys Gly Arg
```

<210> SEQ ID NO 139
<211> LENGTH: 11
<212> TYPE: PRT
<213> ORGANISM: Homo sapiens

<400> SEQUENCE: 139

```
Val Arg Gly Thr Ser Leu Asp Ala Phe Asp Ile
1               5                   10
```

<210> SEQ ID NO 140
<211> LENGTH: 14
<212> TYPE: PRT
<213> ORGANISM: Homo sapiens

<400> SEQUENCE: 140

```
Cys Ser Gly Ser Ser Asn Ile Gly Asn Thr Tyr Val Ser
1               5                   10
```

<210> SEQ ID NO 141
<211> LENGTH: 7
<212> TYPE: PRT
<213> ORGANISM: Homo sapiens

<400> SEQUENCE: 141

```
Tyr Asp Asp Leu Leu Pro Ser
1               5
```

```
<210> SEQ ID NO 142
<211> LENGTH: 12
<212> TYPE: PRT
<213> ORGANISM: Homo sapiens

<400> SEQUENCE: 142

Cys Ala Ala Trp Asp Asp Ser Leu Ser Gly Val Val
1               5                   10

<210> SEQ ID NO 143
<211> LENGTH: 118
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Thr Ser Leu Asp Ala Phe Asp Ile Trp Gly Gln Gly Thr
            100                 105                 110

Leu Val Thr Val Ser Ser
        115

<210> SEQ ID NO 144
<211> LENGTH: 111
<212> TYPE: PRT
<213> ORGANISM: Homo sapiens

<400> SEQUENCE: 144

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly
            100                 105                 110

<210> SEQ ID NO 145
<211> LENGTH: 14
<212> TYPE: PRT
<213> ORGANISM: Homo sapiens

<400> SEQUENCE: 145
```

Phe Ser Asp Tyr Tyr Met Ser Trp Ile Arg Gln Ala Pro Gly
1               5                   10

<210> SEQ ID NO 146
<211> LENGTH: 19
<212> TYPE: PRT
<213> ORGANISM: Homo sapiens

<400> SEQUENCE: 146

Ser Ser Ile Ser Ser Ser Ser Tyr Ile Ser Tyr Ala Asp Ser Met
1               5                   10                  15

Lys Gly Arg

<210> SEQ ID NO 147
<211> LENGTH: 13
<212> TYPE: PRT
<213> ORGANISM: Homo sapiens

<400> SEQUENCE: 147

Ala Thr Ser Glu Ala Ala Ala Asp Tyr Phe Asp Tyr
1               5                   10

<210> SEQ ID NO 148
<211> LENGTH: 15
<212> TYPE: PRT
<213> ORGANISM: Homo sapiens

<400> SEQUENCE: 148

Cys Thr Gly Ser Ser Ser Asn Ile Gly Ala Gly Tyr Asp Val His
1               5                   10                  15

<210> SEQ ID NO 149
<211> LENGTH: 7
<212> TYPE: PRT
<213> ORGANISM: Homo sapiens

<400> SEQUENCE: 149

Asp Asn Asn Lys Arg Pro Ser
1               5

<210> SEQ ID NO 150
<211> LENGTH: 12
<212> TYPE: PRT
<213> ORGANISM: Homo sapiens

<400> SEQUENCE: 150

Cys Ala Ala Trp Asp Asp Ser Leu Asn Gly Pro Val
1               5                   10

<210> SEQ ID NO 151
<211> LENGTH: 120
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ser Ile Ser Ser Ser Ser Tyr Ile Ser Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Thr Ser Glu Ala Ala Ala Asp Tyr Phe Asp Tyr Trp Gly Gln
        100                 105                 110

Gly Thr Leu Val Thr Val Ser Ser
        115                 120

<210> SEQ ID NO 152
<211> LENGTH: 112
<212> TYPE: PRT
<213> ORGANISM: Homo sapiens

<400> SEQUENCE: 152

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Ser
            85                  90                  95

Leu Asn Gly Pro Val Phe Gly Gly Gly Thr Lys Leu Thr Val Leu Gly
            100                 105                 110

<210> SEQ ID NO 153
<211> LENGTH: 14
<212> TYPE: PRT
<213> ORGANISM: Homo sapiens

<400> SEQUENCE: 153

Phe Ser Ser Tyr Ala Met His Trp Val Arg Gln Ala Pro Gly
1               5                   10

<210> SEQ ID NO 154
<211> LENGTH: 19
<212> TYPE: PRT
<213> ORGANISM: Homo sapiens

<400> SEQUENCE: 154

Ala Val Ile Ser Tyr Asp Gly Ser Asn Lys Tyr Tyr Ala Asp Ser Val
1               5                   10                  15

Lys Gly Arg

<210> SEQ ID NO 155
<211> LENGTH: 13
<212> TYPE: PRT
<213> ORGANISM: Homo sapiens

<400> SEQUENCE: 155

Thr Arg Pro Leu Lys Asp Asp Pro Asp Ala Phe Asp Ile
1               5                   10

<210> SEQ ID NO 156

```
<211> LENGTH: 14
<212> TYPE: PRT
<213> ORGANISM: Homo sapiens

<400> SEQUENCE: 156

Cys Ser Gly Ser Ser Ser Asn Ile Gly Ser Tyr Ala Val Asn
1               5                   10

<210> SEQ ID NO 157
<211> LENGTH: 7
<212> TYPE: PRT
<213> ORGANISM: Homo sapiens

<400> SEQUENCE: 157

Arg Asn Asn Gln Arg Pro Ser
1               5

<210> SEQ ID NO 158
<211> LENGTH: 11
<212> TYPE: PRT
<213> ORGANISM: Homo sapiens

<400> SEQUENCE: 158

Cys Phe Ser Tyr Ala Gly Gly Asn Thr Trp Val
1               5                   10

<210> SEQ ID NO 159
<211> LENGTH: 120
<212> TYPE: PRT
<213> ORGANISM: Homo sapiens

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Pro Leu Lys Asp Asp Pro Asp Ala Phe Asp Ile Trp Gly Gln
            100                 105                 110

Gly Thr Leu Val Thr Val Ser Ser
        115                 120

<210> SEQ ID NO 160
<211> LENGTH: 110
<212> TYPE: PRT
<213> ORGANISM: Homo sapiens

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
                20                  25                  30

Ala Val Asn Trp Tyr Gln Gln Leu Pro Gly Thr Ala Pro Lys Leu Leu
            35                  40                  45
```

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Phe Ser Tyr Ala Gly Gly Asn
                85                  90                  95

Thr Trp Val Phe Gly Gly Gly Thr Lys Leu Thr Val Leu Gly
            100                 105                 110

<210> SEQ ID NO 161
<211> LENGTH: 137
<212> TYPE: PRT
<213> ORGANISM: Homo sapiens

<400> SEQUENCE: 161

Met Lys Cys Ser Trp Val Met Phe Phe Leu Met Ala Val Val Thr Gly
1               5                   10                  15

Val Asn Ser Glu Val Gln Leu Gln Gln Ser Gly Ala Glu Leu Val Lys
                20                  25                  30

Pro Gly Ala Ser Val Lys Leu Ser Cys Thr Ala Ser Gly Phe Asn Ile
            35                  40                  45

Lys Asp Ser Tyr Met Tyr Trp Val Lys Gln Arg Pro Glu Gln Gly Leu
    50                  55                  60

Glu Trp Ile Gly Arg Ile Tyr Pro Ala Asn Gly Asp Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Ala Ser Glu Asp Thr Ala Val
            100                 105                 110

Tyr Tyr Cys Thr Arg Gly Tyr Gly Ser Asn Phe Phe Asp Tyr Trp Gly
        115                 120                 125

Gln Gly Thr Thr Leu Thr Val Ser Ser
        130                 135

<210> SEQ ID NO 162
<211> LENGTH: 131
<212> TYPE: PRT
<213> ORGANISM: Homo sapiens

<400> SEQUENCE: 162

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Thr Thr Ile Ser Cys Arg Ala Ser Glu Ser
            35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Phe Thr Phe Gly Gly Gly Thr Lys Leu
        115                 120                 125

Glu Ile Lys
    130

<210> SEQ ID NO 163
<211> LENGTH: 14
<212> TYPE: PRT
<213> ORGANISM: Homo sapiens

<400> SEQUENCE: 163

Phe Ser Ser Tyr Glu Met Asn Trp Val Arg Gln Ala Pro Gly
1               5                   10

<210> SEQ ID NO 164
<211> LENGTH: 19
<212> TYPE: PRT
<213> ORGANISM: Homo sapiens

<400> SEQUENCE: 164

Ser Ala Ile Ser Gly Ser Ala Gly Ser Thr Tyr Tyr Ala Asp Ser Val
1               5                   10                  15

Lys Gly Arg

<210> SEQ ID NO 165
<211> LENGTH: 21
<212> TYPE: PRT
<213> ORGANISM: Homo sapiens

<400> SEQUENCE: 165

Ala Thr Tyr Pro Lys Glu Lys Thr Leu His Gly Gly Arg Tyr Pro Tyr
1               5                   10                  15

Tyr Gly Leu Asp Leu
            20

<210> SEQ ID NO 166
<211> LENGTH: 14
<212> TYPE: PRT
<213> ORGANISM: Homo sapiens

<400> SEQUENCE: 166

Cys Ser Gly Ser Ser Ser Asn Ile Gly Ser Asn Thr Val Asn
1               5                   10

<210> SEQ ID NO 167
<211> LENGTH: 7
<212> TYPE: PRT
<213> ORGANISM: Homo sapiens

<400> SEQUENCE: 167

Asp Asn Asn Lys Arg Pro Leu
1               5

<210> SEQ ID NO 168
<211> LENGTH: 12
<212> TYPE: PRT
<213> ORGANISM: Homo sapiens

<400> SEQUENCE: 168

Cys Ala Thr Trp Asp Asp Ser Leu Ser Gly Pro Val
1               5                   10

<210> SEQ ID NO 169
<211> LENGTH: 121
<212> TYPE: PRT

<213> ORGANISM: Homo sapiens

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Glu Met Asn Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Arg Asn Pro Asp Pro Leu Asp Ala Phe Asp Ile Trp Gly
            100                 105                 110

Gln Gly Thr Leu Val Thr Val Ser Ser
            115                 120

<210> SEQ ID NO 170
<211> LENGTH: 111
<212> TYPE: PRT
<213> ORGANISM: Homo sapiens

<400> SEQUENCE: 170

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Tyr Thr Ser Ile
                85                  90                  95

Ser Thr Val Leu Phe Gly Gly Gly Thr Lys Leu Thr Val Leu Gly
            100                 105                 110

<210> SEQ ID NO 171
<211> LENGTH: 13
<212> TYPE: PRT
<213> ORGANISM: Homo sapiens

<400> SEQUENCE: 171

Ser Ser Tyr Ala Met Ser Trp Val Arg Gln Ala Pro Gly
1               5                   10

<210> SEQ ID NO 172
<211> LENGTH: 19
<212> TYPE: PRT
<213> ORGANISM: Homo sapiens

<400> SEQUENCE: 172

Ala His Thr Asn Glu Asp Gly Ser Asp Lys Lys Tyr Val Asp Ser Val
1               5                   10                  15

Lys Gly Arg

<210> SEQ ID NO 173
<211> LENGTH: 15
<212> TYPE: PRT
<213> ORGANISM: Homo sapiens

<400> SEQUENCE: 173

Ala Arg Asp Gly Ser Gly Tyr Ser Ser Gly Trp Tyr Phe Asp Tyr
1               5                   10                  15

<210> SEQ ID NO 174
<211> LENGTH: 15
<212> TYPE: PRT
<213> ORGANISM: Homo sapiens

<400> SEQUENCE: 174

Cys Thr Gly Thr Thr Ser Asn Leu Gly Ala Gly Tyr Asp Val His
1               5                   10                  15

<210> SEQ ID NO 175
<211> LENGTH: 14
<212> TYPE: PRT
<213> ORGANISM: Homo sapiens

<400> SEQUENCE: 175

Ser Asn Asn Gln Arg Pro Ser Gly Val Pro Asp Arg Phe Ser
1               5                   10

<210> SEQ ID NO 176
<211> LENGTH: 12
<212> TYPE: PRT
<213> ORGANISM: Homo sapiens

<400> SEQUENCE: 176

Cys Gln Ser Tyr Asp Ser Ser Leu Ser Ala Leu Val
1               5                   10

<210> SEQ ID NO 177
<211> LENGTH: 122
<212> TYPE: PRT
<213> ORGANISM: Homo sapiens

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala His Thr Asn Glu Asp Gly Ser Asp Lys Lys Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Gly Tyr Ser Ser Gly Trp Tyr Phe Asp Tyr Trp
            100                 105                 110

Gly Gln Gly Thr Leu Val Thr Val Ser Ser
        115                 120

-continued

```
<210> SEQ ID NO 178
<211> LENGTH: 112
<212> TYPE: PRT
<213> ORGANISM: Homo sapiens

<400> SEQUENCE: 178
```

Gln Ser Val Leu Thr Gln Pro Pro Ser Ala Ser Gly Thr Pro Gly Gln
1               5                   10                  15

Arg Val Thr Ile Ser Cys Thr Gly Thr Thr Ser Asn Leu Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Ser Ala Leu Val Phe Gly Gly Gly Thr Lys Leu Thr Val Leu Gly
            100                 105                 110

```
<210> SEQ ID NO 179
<211> LENGTH: 1422
<212> TYPE: DNA
<213> ORGANISM: Artificial Sequence
<220> FEATURE:
<223> OTHER INFORMATION: Chimeric sequence; from Mus musculus and Rattus
      Norvegicus <400> SEQUENCE: 179
aagcttcagg acctcaccat ggagatctgg ctcagcttgg ttttccttgt ccttttcata      60
aaaggtgtcc agtgtgaggt gcagctggtg gagtctggtg gaggcttagt gcagcctgga    120
aggtccctga aactctcctg tgcagcctca ggattcactt tcagtaactt tggcatggcc    180
tgggtctgcc aggctccaac gacggggctg gagtgggtcg caaccattag ttatgatggt    240
actgacagtt actatcgaga ctccgtgaag gaccgattca ctatctccag agataatgca    300
aaaagcaccc tatacctgca aatggacagt ctgaggtctg aggacacggc cgcttattac    360
tgtgtaagac atgaggatgt atactacgga atggggtact tgatcactg gggccaagga    420
gtactagtca cagtctcctc agccaaaacg acaccccca tctgtctatcc actgcccct    480
ggatctgctg cccaaactaa ctccatggtg accctgggat gcctggtcaa gggctatttc    540
cctgagccag tgacagtgac ctggaactct ggttccctgt ccagcggtgt gcacaccttc    600
ccagctgtcc tgcagtctga cctctacact ctgagcagct cagtgactgt ccctccagc    660
acctggccca gcgagaccgt cacctgcaac gttgcccacc cggccagcag caccaaggtg    720
gacaagaaaa ttgtgcccag ggattgtggt tgtaagcctt gcatatgtac agtcccagaa    780
gtatcatctg tcttcatctt ccccccaaag cccaaggatg tgctcaccat tactctgact    840
cctaaggtca cgtgtgttgt ggtagacatc agcaaggatg atcccgaggt ccagttcagc    900
tggtttgtag atgatgtgga ggtgcacaca gctcagacgc aaccccggga ggagcagttc    960
aacagcactt tccgctcagt cagtgaactt ccatcatgc accaggactg gctcaatggc   1020
aaggagttca atgcagggt caacagtgca gctttccctg cccccatcga gaaaaccatc   1080
tccaaaacca aaggcagacc gaaggctcca caggtgtaca ccattccacc tcccaaggag   1140
cagatggcca aggataaagt cagtctgacc tgcatgataa cagacttctt ccctgaagac   1200
```

-continued

```
attactgtgg agtggcagtg gaatgggcag ccagcggaga actacaagaa cactcagccc      1260
atcatggaca cagatggctc ttacttcgtc tacagcaagc tcaatgtgca gaagagcaac      1320
tgggaggcag gaaatacttt cacctgctct gtgttacatg agggcctgca caaccaccat      1380
actgagaaga gcctctccca ctctcctggt aaatgagaat tc                         1422
```

<210> SEQ ID NO 180
<211> LENGTH: 465
<212> TYPE: PRT
<213> ORGANISM: Artificial Sequence
<220> FEATURE:
<223> OTHER INFORMATION: Chimeric sequence; from Mus musculus and Rattus
      Norvegicus
<220> FEATURE:
<221> NAME/KEY: MISC_FEATURE
<222> LOCATION: (1)..(19)
<223> OTHER INFORMATION: Residues 1-19 form leader sequence

<400> SEQUENCE: 180

```
Met Glu Ile Trp Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Phe Gly Met Ala Trp Val Cys Gln Ala Pro Thr Thr Gly Leu
    50                  55                  60

Glu Trp Val Ala Thr Ile Ser Tyr Asp Gly Thr Asp Ser Tyr Tyr Arg
65                  70                  75                  80

Asp Ser Val Lys Asp Arg Phe Thr Ile Ser Arg Asp Asn Ala Lys Ser
                85                  90                  95

Thr Leu Tyr Leu Gln Met Asp Ser Leu Arg Ser Glu Asp Thr Ala Ala
            100                 105                 110

Tyr Tyr Cys Val Arg His Glu Asp Val Tyr Tyr Gly Met Gly Tyr Phe
        115                 120                 125

Asp His Trp Gly Gln Gly Val Leu Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285

Pro Glu Val Gln Phe Ser Trp Phe Val Asp Asp Val Glu Val His Thr
    290                 295                 300
```

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
            325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
            355                 360                 365

Ile Pro Pro Pro Lys Glu Gln Met Ala Lys Asp Lys Val Ser Leu Thr
        370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met
                405                 410                 415

Asp Thr Asp Gly Ser Tyr Phe Val Tyr Ser Lys Leu Asn Val Gln Lys
            420                 425                 430

Ser Asn Trp Glu Ala Gly Asn Thr Phe Thr Cys Ser Val Leu His Glu
            435                 440                 445

Gly Leu His Asn His His Thr Glu Lys Ser Leu Ser His Ser Pro Gly
        450                 455                 460

Lys
465

<210> SEQ ID NO 181
<211> LENGTH: 1440
<212> TYPE: DNA
<213> ORGANISM: Artificial Sequence
<220> FEATURE:
<223> OTHER INFORMATION: Chimeric sequence; from Mus musculus and Rattus
      Norvegicus

<400> SEQUENCE: 181
aagcttcagg acctcaccat ggagatctgg ctcagcttgg ttttccttgt ccttttcata      60
aaaggtgtcc agtgtgaggt gcagctggtg gagtctggtg gaggcttagt gcagcctgga     120
aggtccctga actctcctg tgcagcctca ggattcactt tcagtaactt tggcatggcc      180
tgggtctgcc aggctccaac gacggggctg gagtgggtcg caaccattag ttatgatggt     240
actgacagtt actatcgaga ctccgtgaag gaccgattca ctatctccag agataatgca     300
aaaagcaccc tatacctgca aatggacagt ctgaggtctg aggacacggc cgcttattac     360
tgtgtaagac atgaggatgt atactacgga atggggtact tgatcactg ggccaagga      420 gtactagtca cagtctcctc agccaaaacg acagccccat cggtctatcc actggcccct     480
gtgtgtggag atacaactgg ctcctcggtg actctaggat gcctggtcaa gggttatttc     540
cctgagccag tgaccttgac ctggaactct ggatccctgt ccagtggtgt gcacaccttc     600
ccagctgtcc tgcagtctga cctctacacc ctcagcagct cagtgactgt aacctcgagc     660
acctggccca gccagtccat cacctgcaat gtggcccacc cggcaagcag caccaaggtg     720
gacaagaaaa ttgagcccag agggcccaca atcaagccct gtcctccatg caaatgccca     780
gcacctaacc tcttgggtgg accatccgtc ttcatcttcc ctccaaagat caaggatgta     840
ctcatgatct ccctgagccc catagtcaca tgtgtggtgg tggatgtgag cgaggatgac     900
ccagatgtcc agatcagctg gtttgtgaac aacgtggaag tacacacagc tcagacacaa     960
acccatagag aggattacaa cagtactctc cgggtggtca gtgccctccc catccagcac    1020

```
caggactgga tgagtggcaa ggagttcaaa tgcaaggtca acaacaaaga cctcccagcg    1080
cccatcgaga gaaccatctc aaaacccaaa gggtcagtaa gagctccaca ggtatatgtc    1140
ttgcctccac cagaagaaga gatgactaag aaacaggtca ctctgacctg catggtcaca    1200
gacttcatgc ctgaagacat ttacgtggag tggaccaaca cgggaaaac agagctaaac     1260 tacaagaaca ctgaaccagt cctggactct gatggttctt acttcatgta cagcaagctg    1320
agagtggaaa agaagaactg ggtggaaaga aatagctact cctgttcagt ggtccacgag    1380
ggtctgcaca atcaccacac gactaagagc ttctcccgga ctccgggtaa atgagaattc    1440
```

<210> SEQ ID NO 182
<211> LENGTH: 471
<212> TYPE: PRT
<213> ORGANISM: Artificial Sequence
<220> FEATURE:
<223> OTHER INFORMATION: Chimeric sequence; from Mus musculus and Rattus
      Norvegicus
<220> FEATURE:
<221> NAME/KEY: MISC_FEATURE
<222> LOCATION: (1)..(19)
<223> OTHER INFORMATION: Residues 1-19 form leader sequence

<400> SEQUENCE: 182

```
Met Glu Ile Trp Leu Ser Leu Val Phe Leu Val Leu Phe Ile Lys Gly
 1               5                  10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Phe Gly Met Ala Trp Val Cys Gln Ala Pro Thr Thr Gly Leu
    50                  55                  60

Glu Trp Val Ala Thr Ile Ser Tyr Asp Gly Thr Asp Ser Tyr Tyr Arg
65                  70                  75                  80

Asp Ser Val Lys Asp Arg Phe Thr Ile Ser Arg Asp Asn Ala Lys Ser
                85                  90                  95

Thr Leu Tyr Leu Gln Met Asp Ser Leu Arg Ser Glu Asp Thr Ala Ala
            100                 105                 110

Tyr Tyr Cys Val Arg His Glu Asp Val Tyr Tyr Gly Met Gly Tyr Phe
        115                 120                 125

Asp His Trp Gly Gln Gly Val Leu Val Thr Val Ser Ser Ala Lys Thr
    130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Thr Ser Ser Thr Trp Pro Ser Gln Ser Ile Thr Cys Asn
    210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Cys Lys Cys Pro Ala Pro
                245                 250                 255

Asn Leu Leu Gly Gly Pro Ser Val Phe Ile Phe Pro Pro Lys Ile Lys
            260                 265                 270
```

-continued

Asp Val Leu Met Ile Ser Leu Ser Pro Ile Val Thr Cys Val Val
    275                 280                 285
Asp Val Ser Glu Asp Asp Pro Asp Val Gln Ile Ser Trp Phe Val Asn
    290                 295                 300
Asn Val Glu Val His Thr Ala Gln Thr Gln Thr His Arg Glu Asp Tyr
305                 310                 315                 320
Asn Ser Thr Leu Arg Val Val Ser Ala Leu Pro Ile Gln His Gln Asp
                325                 330                 335
Trp Met Ser Gly Lys Glu Phe Lys Cys Lys Val Asn Asn Lys Asp Leu
            340                 345                 350
Pro Ala Pro Ile Glu Arg Thr Ile Ser Lys Pro Lys Gly Ser Val Arg
        355                 360                 365
Ala Pro Gln Val Tyr Val Leu Pro Pro Pro Glu Glu Glu Met Thr Lys
    370                 375                 380
Lys Gln Val Thr Leu Thr Cys Met Val Thr Asp Phe Met Pro Glu Asp
385                 390                 395                 400
Ile Tyr Val Glu Trp Thr Asn Asn Gly Lys Thr Glu Leu Asn Tyr Lys
                405                 410                 415
Asn Thr Glu Pro Val Leu Asp Ser Asp Gly Ser Tyr Phe Met Tyr Ser
            420                 425                 430
Lys Leu Arg Val Glu Lys Lys Asn Trp Val Glu Arg Asn Ser Tyr Ser
        435                 440                 445
Cys Ser Val Val His Glu Gly Leu His Asn His His Thr Thr Lys Ser
    450                 455                 460
Phe Ser Arg Thr Pro Gly Lys
465                 470

<210> SEQ ID NO 183
<211> LENGTH: 723
<212> TYPE: DNA
<213> ORGANISM: Mus musculus

<400> SEQUENCE: 183
aagcttcagg acctcaccat ggctgcacta caactcttag gctgctgct gctctggctc      60 ccagccatga gatgtgacat ccagatgacc cagtctcctt cattcctgtc tgcatctgtg     120
ggagacagag tcactctcaa ctgcaaagca agtcagaata ttaacaagta cttagactgg     180
tatcagcaaa agctgggtga agctcccaaa ctcctgatgt ataatacaaa cagtttgcat     240
acggcaatcc cgtcaaggtt cagtggcagt ggatctggtt ctgatttcac acttaccata     300
agcagcctgc agcctgaaga tgttgccaca tatttctgct ttcagcatag cagtgggtgg     360
acgttcggtg gaggcaccaa gctggaattg aaacgtacgg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600 agcacctca cgttgaccaa ggacgagtat gaacgacata cagctatac ctgtgaggcc      660 actcacaaga catcaacttc acccattgtc aagagcttca caggaatga gtgttaggaa     720 ttc                                                                  723

<210> SEQ ID NO 184
<211> LENGTH: 232
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: Residues 1-19 form leader sequence

<400> SEQUENCE: 184

```
Met Ala Ala Leu Gln Leu Leu Gly Leu Leu Leu Leu Trp Leu Pro Ala
1               5                   10                  15

Met Arg Cys Asp Ile Gln Met Thr Gln Ser Pro Ser Phe Leu Ser Ala
            20                  25                  30

Ser Val Gly Asp Arg Val Thr Leu Asn Cys Lys Ala Ser Gln Asn Ile
        35                  40                  45

Asn Lys Tyr Leu Asp Trp Tyr Gln Gln Lys Leu Gly Glu Ala Pro Lys
    50                  55                  60

Leu Leu Met Tyr Asn Thr Asn Ser Leu His Thr Ala Ile Pro Ser Arg
65                  70                  75                  80

Phe Ser Gly Ser Gly Ser Gly Ser Asp Phe Thr Leu Thr Ile Ser Ser
                85                  90                  95

Leu Gln Pro Glu Asp Val Ala Thr Tyr Phe Cys Gln His Ser Ser
            100                 105                 110

Gly Trp Thr Phe Gly Gly Gly Thr Lys Leu Glu Leu Lys Arg Thr Asp
        115                 120                 125

Ala Ala Pro Thr Val Ser Ile Phe Pro Pro Ser Ser Glu Gln Leu Thr
    130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
        195                 200                 205

Ser Tyr Thr Cys Glu Ala Thr His Lys Thr Ser Thr Ser Pro Ile Val
    210                 215                 220

Lys Ser Phe Asn Arg Asn Glu Cys
225                 230
```

<210> SEQ ID NO 185
<211> LENGTH: 1431
<212> TYPE: DNA
<213> ORGANISM: Artificial Sequence
<220> FEATURE:
<223> OTHER INFORMATION: Human IgG2 region cloned into murine mIgG2a constant regions, with hinge skewed to agonism enhanced 'B' form

<400> SEQUENCE: 185

```
aagcttcagg acctcaccat ggagatctgg ctcagcttgg ttttccttgt cctttcata      60 aaaggtgtcc agtgtgaggt gcagctggtg gagtctggtg gaggcttagt gcagcctgga    120
aggtccctga aactctcctg tgcagcctca ggattcactt tcagtaactt tggcatggcc    180
tgggtctgcc aggctccaac gacggggctg gagtgggtcg caaccattag ttatgatggt    240
actgacagtt actatcgaga ctccgtgaag gaccgattac tatctccag agataatgca    300 aaaagcaccc tatacctgca aatggacagt ctgaggtctg aggacacggc cgcttattac    360
tgtgtaagac atgaggatgt atactacgga atggggtact tgatcactg gggccaagga    420 gtactagtca ccgtctcctc agcctccacc aagggcccat cggtcttccc cctggcgccc    480
```

```
tgctccagga gcacctccga gagcacagcg ccctgggct gcctggtcaa ggactacttc      540
cccgaaccgg tgacggtgtc gtggaactca ggcgctctga ccagcggcgt gcacaccttc      600
ccagctgtcc tacagtcctc aggactctac tccctcagca gcgtggtgac cgtgccctcc      660
agcaacttcg gcacccagac ctacacctgc aacgtagatc acaagcccag caacaccaag      720
gtggacaaga cagttgagcg caaatgttgt gtcgagtgcc caccgtgccc agcacctaac      780
ctcttgggtg gaccatccgt cttcatcttc cctccaaaga tcaaggatgt actcatgatc      840
tccctgagcc ccatagtcac atgtgtggtg gtggatgtga gcgaggatga cccagatgtc      900
cagatcagct ggtttgtgaa caacgtggaa gtacacacag ctcagacaca aacccataga      960
gaggattaca acagtactct ccgggtggtc agtgccctcc ccatccagca ccaggactgg     1020
atgagtggca aggagttcaa atgcaaggtc aacaacaaag acctcccagc gcccatcgag     1080
agaaccatct caaacccaa agggtcagta agagctccac aggtatatgt cttgcctcca      1140
ccagaagaag agatgactaa gaaacaggtc actctgacct gcatggtcac agacttcatg     1200
cctgaagaca tttacgtgga gtggaccaac aacgggaaaa cagagctaaa ctacaagaac     1260
actgaaccag tcctggactc tgatggttct tacttcatgt acagcaagct gagagtggaa     1320
aagaagaact gggtggaaag aaatagctac tcctgttcag tggtccacga gggtctgcac     1380
aatcaccaca cgactaagag cttctcccgg actccgggta atgagaatt c              1431
```

<210> SEQ ID NO 186
<211> LENGTH: 468
<212> TYPE: PRT
<213> ORGANISM: Artificial Sequence
<220> FEATURE:
<223> OTHER INFORMATION: Human IgG2 region cloned into murine mIgG2a
      constant regions, with hinge skewed to agonism enhanced 'B' form
<220> FEATURE:
<221> NAME/KEY: MISC_FEATURE
<222> LOCATION: (1)..(19)
<223> OTHER INFORMATION: Residues 1-19 form leader sequence

<400> SEQUENCE: 186

```
Met Glu Ile Trp Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Arg Ser Leu Lys Leu Ser Cys Ala Ala Ser Gly Phe Thr Phe
            35                  40                  45

Ser Asn Phe Gly Met Ala Trp Val Cys Gln Ala Pro Thr Thr Gly Leu
        50                  55                  60

Glu Trp Val Ala Thr Ile Ser Tyr Asp Gly Thr Asp Ser Tyr Tyr Arg
65                  70                  75                  80

Asp Ser Val Lys Asp Arg Phe Thr Ile Ser Arg Asp Asn Ala Lys Ser
                85                  90                  95

Thr Leu Tyr Leu Gln Met Asp Ser Leu Arg Ser Glu Asp Thr Ala Ala
            100                 105                 110

Tyr Tyr Cys Val Arg His Glu Asp Val Tyr Tyr Gly Met Gly Tyr Phe
        115                 120                 125

Asp His Trp Gly Gln Gly Val Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Asn Phe Gly Thr Gln Thr Tyr Thr Cys
            210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Asn Leu Leu
                245                 250                 255
Gly Gly Pro Ser Val Phe Ile Phe Pro Pro Lys Ile Lys Asp Val Leu
            260                 265                 270
Met Ile Ser Leu Ser Pro Ile Val Thr Cys Val Val Asp Val Ser
            275                 280                 285
Glu Asp Asp Pro Asp Val Gln Ile Ser Trp Phe Val Asn Asn Val Glu
    290                 295                 300
Val His Thr Ala Gln Thr Gln Thr His Arg Glu Asp Tyr Asn Ser Thr
305                 310                 315                 320
Leu Arg Val Val Ser Ala Leu Pro Ile Gln His Gln Asp Trp Met Ser
                325                 330                 335
Gly Lys Glu Phe Lys Cys Lys Val Asn Asn Lys Asp Leu Pro Ala Pro
            340                 345                 350
Ile Glu Arg Thr Ile Ser Lys Pro Lys Gly Ser Val Arg Ala Pro Gln
            355                 360                 365
Val Tyr Val Leu Pro Pro Glu Glu Glu Met Thr Lys Lys Gln Val
370                 375                 380
Thr Leu Thr Cys Met Val Thr Asp Phe Met Pro Glu Asp Ile Tyr Val
385                 390                 395                 400
Glu Trp Thr Asn Asn Gly Lys Thr Glu Leu Asn Tyr Lys Asn Thr Glu
                405                 410                 415
Pro Val Leu Asp Ser Asp Gly Ser Tyr Phe Met Tyr Ser Lys Leu Arg
            420                 425                 430
Val Glu Lys Lys Asn Trp Val Glu Arg Asn Ser Tyr Ser Cys Ser Val
            435                 440                 445
Val His Glu Gly Leu His Asn His His Thr Thr Lys Ser Phe Ser Arg
450                 455                 460
Thr Pro Gly Lys
465

<210> SEQ ID NO 187
<211> LENGTH: 723
<212> TYPE: DNA
<213> ORGANISM: Homo sapiens

<400> SEQUENCE: 187
aagcttcagg acctcaccat ggctgcacta caactcttag gctgctgct gctctggctc      60 ccagccatga gatgtgacat ccagatgacc cagtctcctt cattcctgtc tgcatctgtg    120
ggagacagag tcactctcaa ctgcaaagca agtcagaata ttaacaagta cttagactgg    180
tatcagcaaa agctgggtga agctcccaaa ctcctgatgt ataatacaaa cagtttgcat    240
acggcaatcc cgtcaaggtt cagtggcagt ggatctggtt ctgatttcac acttaccata    300
agcagcctgc agcctgaaga tgttgccaca tatttctgct ttcagcatag cagtgggtgg    360
acgttcggtg gaggcaccaa gctggaattg aaacgtacgg tggctgcacc atctgtcttc    420
```

```
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca cagggaga gtgttgagaa      720 ttc                                                                  723
```

<210> SEQ ID NO 188
<211> LENGTH: 232
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Residues 1-19 form leader sequence

<400> SEQUENCE: 188

```
Met Ala Ala Leu Gln Leu Leu Gly Leu Leu Leu Leu Trp Leu Pro Ala
1               5                   10                  15

Met Arg Cys Asp Ile Gln Met Thr Gln Ser Pro Ser Phe Leu Ser Ala
            20                  25                  30

Ser Val Gly Asp Arg Val Thr Leu Asn Cys Lys Ala Ser Gln Asn Ile
        35                  40                  45

Asn Lys Tyr Leu Asp Trp Tyr Gln Gln Lys Leu Gly Glu Ala Pro Lys
    50                  55                  60

Leu Leu Met Tyr Asn Thr Asn Ser Leu His Thr Ala Ile Pro Ser Arg
65                  70                  75                  80

Phe Ser Gly Ser Gly Ser Gly Ser Asp Phe Thr Leu Thr Ile Ser Ser
                85                  90                  95

Leu Gln Pro Glu Asp Val Ala Thr Tyr Phe Cys Phe Gln His Ser Ser
            100                 105                 110

Gly Trp Thr Phe Gly Gly Gly Thr Lys Leu Glu Leu Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

COMBINATION OF A TREG DEPLETING ANTI-4-1BB ANTIBODY AND ANTI-PD1 ANTIBODY

This application is a national phase application under 35 U.S.C. § 371 of International Application No. PCT/EP2018/070359, filed Jul. 26, 2018, which claims priority to United Kingdom Application No. 1712032.0, filed Jul. 26, 2017. The entire text of each of the above referenced disclosures is specifically incorporated herein by reference.

FIELD OF THE INVENTION

The present invention relates to sequential administration of first a Treg depleting antibody molecule and then an immunostimulatory antibody molecule for use in the treatment of cancer. The invention also relates to novel antibodies for use in such treatment, including novel anti-4-1 BB antibodies and novel anti-OX40 antibodies.

BACKGROUND OF THE INVENTION

Promising clinical results with immunomodulatory mAb have revived the belief that the immune system holds the key to controlling cancer. The classification of these mAb into checkpoint blockers (antagonists) or activators of co-stimulatory molecules (agonists) has recently come into question with the finding that examples of both types may combat tumours through activatory FcγR engagement and depletion of suppressive regulatory T cells (Treg). In contrast to these findings, anti-CD40 mAb depend on inhibitory FcγR cross-linking for agonistic immune stimulation. Therefore whilst immunomodulatory mAb offer considerable promise for cancer immunotherapy the effector mechanisms employed by various mAb, and consequently their optimal application, remain to be defined.

Immunomodulatory mAb, such as ipilimumab (anti-CTLA4), anti-PD-1/PD-L1 and anti-CD40 have shown positive outcomes when trialled in difficult-to-treat malignancies, albeit in a minority of patients (1-4). These promising results have helped to reinvigorate the belief that the immune system can hold the key to controlling cancer. These mAb were generated to target key molecular regulators on T cells or APC and to boost anti-cancer immunity through blockade of inhibitory signals (checkpoint blockers) or delivery of co-stimulatory signals (agonists). Recently this binary classification has come into question when the therapeutic activity of anti-CTLA4, anti-GITR and anti-OX40, which all target T cells, was found to involve deletion of suppressive CD4+ T regulatory cells dependent on co-engagement of activatory FcγRs (5-7). The activity of the agonist APC-targeting anti-CD40 mAb, in contrast, requires co-engagement of the inhibitory FcγR to facilitate effective mAb cross-linking, which is necessary for CD40 signalling and immune stimulation (8-10). Therefore, whilst immunomodulatory mAb offer considerable promise for cancer immunotherapy, the mechanisms employed depend on both the Fab and Fc regions of the mAb in ways which are ill-defined and which may depend on the cell type being targeted. Understanding the relative importance of $T_{reg}$ depletion versus direct immune-stimulation will be vital to the development and successful translation of immunomodulatory mAb to patients.

SUMMARY OF THE INVENTION

The present invention is based on research demonstrating that anti-4-1BB mAb can employ either direct immune-stimulation or $T_{reg}$ depletion in solid tumours, with the primary mechanism dependent on antibody isotype and FcγR availability. Importantly, depletion and immunostimulation appear to be competitive mechanisms, likely limited by restrictions on FcγR engagement. The research leading to the present invention has further shown that sequential administration of isotype-disparate anti-4-1 BB mAbs or isotype-optimal anti-4-1 BB mAb followed by anti-PD-1 mAb to initially delete Treg and then stimulate CD8 T cells leads to augmented responses, resulting in enhanced therapy and improved outcome. Furthermore, the inventors engineered a depleting anti-4-1 BB mIgG2a with human IgG2 hinge region 'B' (mIgG2a/h2B) to provide FcγR independent agonism and demonstrate that this single mAb is capable of harnessing both mechanisms to deliver enhanced therapy.

This was then broadened by demonstration that Treg depletion followed by immunostimulation can be achieved with further antibodies in addition to anti-4-1 BB mAb, namely a Treg depleting antibody molecule, such as an antibody molecules binding specifically to target belonging to the tumour necrosis factor receptor superfamily (TNFRSF), for example a Treg depleting anti-4-1 BB antibody or a Treg depleting anti-OX40 antibody, in combination with an immunostimulatory antibody molecule, such as an immunostimulatory anti-4-1 BB antibody, an immunostimulatory anti-OX40 antibody or an immune activatory PD-1 blocking antibody, wherein the order of administration is of importance to achieve the desired effect. The research also lead to the development of novel anti-4-1BB antibodies and novel anti-OX40 antibodies.

Thus, the present invention relates to a Treg depleting antibody molecule for use in the treatment of cancer wherein the Treg depleting antibody molecule is administered sequentially with an immunostimulatory antibody molecule with the Treg depleting antibody molecule being administered prior to administration of the immunostimulatory antibody molecule.

The present invention further relates to a method of treating a cancer in a subject, said treatment comprising administration of a Treg depleting antibody molecule followed sequentially by administration of an immunostimulatory antibody molecule.

The present invention further relates to an anti-4-1 BB antibody molecule selected from the group consisting of antibody molecules comprising one or more of the CDRs selected from SEQ. ID. NOs: 1-6, 9-14, 17-22, 25-30, 33-38, 41-46, 49-54, 57-62, 65-70, 153-158 and 163-168. "One or more" means in this context that the antibody molecule comprises 1, 2, 3, 4, 5 or 6 of the indicated sequences, i.e. 1-6 of the indicated sequences. Thus, the anti-4-1 BB antibody molecule may comprise 1-6 of the CDRs selected from SEQ. ID. NOs: 1-6; 1-6 of the CDRs selected from SEQ. ID. NOs: 9-14; 1-6 of the CDRs selected from SEQ. ID. NOs: 17-22; 1-6 of the CDRs selected from SEQ. ID. NOs: 25-30; 1-6 of the CDRs selected from SEQ. ID. NOs: 33-38; 1-6 of the CDRs selected from SEQ. ID. NOs: 41-46; 1-6 of the CDRs selected from SEQ. ID. NOs: 49-54; 1-6 of the CDRs selected from SEQ. ID. NOs: 57-62; 1-6 of the CDRs selected from SEQ. ID. NOs: 65-70; 1-6 of the CDRs selected from SEQ. ID. NOs: 153-158; or 1-6 of the CDRs selected from SEQ. ID. NOs: 163-168.

The present invention further relates to nucleotide acids encoding the above anti-4-1BB antibody molecules.

The present invention further relates to an anti-OX40 antibody molecule selected from the group consisting of antibody molecule comprising one or more of the CDRs selected from SEQ. ID. NOs: 73-78, 81-86, 89-94, 97-102, 105-110, SEQ. ID. NOs: 113-118, SEQ. ID. NOs: 121-126, SEQ. ID. NOs: 129-134, SEQ. ID. NOs: 137-142, SEQ. ID. NOs: 145-150, and SEQ. ID. NOs: 171-176. Again "one or more" means in this context that the antibody molecule comprises 1, 2, 3, 4, 5 or 6 of the indicated sequences, i.e. 1-6 of the indicated sequences. Thus, the anti-OX40 antibody molecule may comprise 1-6 of the CDRs selected from SEQ. ID. NOs: 73-78; 1-6 of the CDRs selected from SEQ. ID. NOs: 81-86; 1-6 of the CDRs selected from SEQ. ID. NOs: 89-94; 1-6 of the CDRs selected from SEQ. ID. NOs: 97-102; 1-6 of the CDRs selected from SEQ. ID. NOs: 105-110; 1-6 of the CDRs selected from SEQ. ID. NOs: 113-118; 1-6 of the CDRs selected from SEQ. ID. NOs: 121-126; 1-6 of the CDRs selected from SEQ. ID. NOs: 129-134; 1-6 of the CDRs selected from SEQ. ID. NOs: 137-142; 1-6 of the CDRs selected from SEQ. ID. NOs: 145-150, or 1-6 of the CDRs selected from SEQ. ID. NOs: 171-176.

The present invention further relates to vectors comprising the above nucleotide acids.

The present invention further relates to host cells comprising the above nucleotide acids and/or the above vectors.

DETAILED DESCRIPTION OF THE INVENTION

Regulatory T cells, Treg cells, Tregs or $T_{regs}$, (formerly known as suppressor T cells, sometimes also called suppressive regulatory T cells), are a subpopulation of T cells which are capable of suppressing other immune cells in normal and pathological immune settings.

By depletion of Tregs, or Treg depletion, we refer herein to depletion, deletion or elimination of Tregs through physical clearance of cells. In particular, we refer to depletion of intratumoural Tregs.

Effector T cells are T cells or T lymphocytes that in response to stimulus activate, attack or destroy antigen-expressing cells in an antigen:MHC:TCR-restricted manner. Effector T cells may control cancer and eradicate tumor cells directly (cytotoxic T cells), or indirectly (T Helper cells) through activation of other immune cells.

Antibodies are well known to those skilled in the art of immunology and molecular biology. Typically, an antibody comprises two heavy (H) chains and two light (L) chains. Herein, we sometimes refer to this complete antibody molecule as a full-size or full-length antibody. The antibody's heavy chain comprises one variable domain (VH) and three constant domains (CH1, CH2 and CH3), and the antibody's molecule light chain comprises one variable domain (VL) and one constant domain (CL). The variable domains (sometimes collectively referred to as the $F_v$ region) bind to the antibody's target, or antigen. Each variable domain comprises three loops, referred to as complementary determining regions (CDRs), which are responsible for target binding. The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and in humans several of these are further divided into subclasses (isotypes), e.g., IgG1, IgG2, IgG3, and IgG4; IgA1 and IgA2. Another part of an antibody is the Fc domain (otherwise known as the fragment crystallisable domain), which comprises two of the constant domains of each of the antibody's heavy chains. The Fc domain is responsible for interactions between the antibody and Fc receptor.

Fc receptors are membrane proteins which are often found on the cell surface of cells of the immune system (i.e. Fc receptors are found on the target cell membrane—otherwise known as the plasma membrane or cytoplasmic membrane). The role of Fc receptors is to bind antibodies via the Fc domain, and to internalize the antibody into the cell. In the immune system, this can result in antibody-mediated phagocytosis and antibody-dependent cell-mediated cytotoxicity.

The term antibody molecule, as used herein, encompasses full-length or full-size antibodies as well as functional fragments of full length antibodies and derivatives of such antibody molecules.

Functional fragments of a full-size antibody have the same antigen binding characteristics as the corresponding full-size antibody and include either the same variable domains (i.e. the VH and VL sequences) and/or the same CDR sequences as the corresponding full-size antibody. That the functional fragment has the same antigen binding characteristics as the corresponding full-size antibody means that it binds to the same epitope on the target as the full-size antibody. Such a functional fragment may correspond to the $F_v$ part of a full-size antibody. Alternatively, such a fragment may be a Fab, also denoted F(ab), which is a monovalent antigen-binding fragment that does not contain a Fc part, or a F(ab')$_2$, which is an divalent antigen-binding fragment that contains two antigen-binding Fab parts linked together by disulfide bonds or a F(ab'), i.e. a monovalent-variant of a F(ab')$_2$. Such a fragment may also be single chain variable fragment (scFv).

A functional fragment does not always contain all six CDRs of a corresponding full-size antibody. It is appreciated that molecules containing three or fewer CDR regions (in some cases, even just a single CDR or a part thereof) are capable of retaining the antigen-binding activity of the antibody from which the CDR(s) are derived. For example, in Gao et al., 1994, J. Biol. Chem., 269: 32389-93 it is described that a whole VL chain (including all three CDRs) has a high affinity for its substrate.

Molecules containing two CDR regions are described, for example, by Vaughan & Sollazzo 2001, Combinatorial Chemistry & High Throughput Screening, 4: 417-430. On page 418 (right column—3 Our Strategy for Design) a minibody including only the H1 and H2 CDR hypervariable regions interspersed within framework regions is described. The minibody is described as being capable of binding to a target. Pessi et al., 1993, Nature, 362: 367-9 and Bianchi et al., 1994, J. Mol. Biol., 236: 649-59 are referenced by Vaughan & Sollazzo and describe the H1 and H2 minibody and its properties in more detail. In Qiu et al., 2007, Nature Biotechnology, 25:921-9 it is demonstrated that a molecule consisting of two linked CDRs are capable of binding antigen. Quiocho 1993, Nature, 362: 293-4 provides a summary of "minibody" technology. Ladner 2007, Nature Biotechnology, 25:875-7 comments that molecules containing two CDRs are capable of retaining antigen-binding activity.

Antibody molecules containing a single CDR region are described, for example, in Laune et al., 1997, JBC, 272: 30937-44, in which it is demonstrated that a range of hexapeptides derived from a CDR display antigen-binding activity and it is noted that synthetic peptides of a complete, single, CDR display strong binding activity. In Monnet et al., 1999, JBC, 274: 3789-96 it is shown that a range of 12-mer peptides and associated framework regions have antigen-binding activity and it is commented on that a CDR3-like peptide alone is capable of binding antigen. In Heap et al., 2005, J. Gen. Virol., 86: 1791-1800 it is reported that a "micro-antibody" (a molecule containing a single CDR) is capable of binding antigen and it is shown that a cyclic peptide from an anti-HIV antibody has antigen-binding activity and function. In Nicaise et al., 2004, Protein Science, 13:1882-91 it is shown that a single CDR can confer antigen-binding activity and affinity for its lysozyme antigen.

Thus, antibody molecules having five, four, three or fewer CDRs are capable of retaining the antigen binding properties of the full-length antibodies from which they are derived.

The antibody molecule may also be a derivative of a full-length antibody or a fragment of such an antibody. The derivative has the same antigen binding characteristics as the corresponding full-size antibody in the sense that it binds to the same epitope on the target as the full-size antibody.

Thus, by the term "antibody molecule", as used herein, we include all types of antibody molecules and functional fragments thereof and derivatives thereof, including: monoclonal antibodies, polyclonal antibodies, synthetic antibodies, recombinantly produced antibodies, multi-specific antibodies, bi-specific antibodies, human antibodies, humanized antibodies, chimeric antibodies, single chain antibodies, single-chain Fvs (scFv), Fab fragments, F(ab')$_2$ fragments, F(ab') fragments, disulfide-linked Fvs (sdFv), antibody heavy chains, antibody light chains, homo-dimers of antibody heavy chains, homo-dimers of antibody light chains, heterodimers of antibody heavy chains, heterodimers of antibody light chains, antigen binding functional fragments of such homo- and heterodimers.

Further, the term "antibody molecule", as used herein, includes all classes of antibody molecules and functional fragments, including: IgG, IgG1, IgG2, IgG3, IgG4, IgA, IgM, IgD, and IgE.

In some embodiments, the antibody is a human IgG1. The skilled person is aware that the mouse IgG2a and human IgG1 productively engage with activatory Fc gamma receptors, and share the ability to activate deletion of target cells through activation of activatory Fc gamma receptor bearing immune cells (e.g. macrophages and NK cells) by e.g. ADCP and ADCC. As such, whereas the mouse IgG2a is the preferred isotype for deletion in the mouse, human IgG1 is a preferred isotype for deletion in human. Conversely, it is known that optimal co-stimulation of TNFR superfamily agonist receptors e.g. 4-1BB, ox40, TNFRII, CD40 depends on antibody engagement of the inhibitory FcγRII. In the mouse the IgG1 isotype, which binds preferentially to inhibitory Fc gamma receptor (FcγRIIB) and only weakly to activatory Fc gamma receptors, is known to be optimal for costimulatory activity of TNFR-superfamily targeting mAb. While no direct equivalent of the mouse IgG1 isotype has been described in man, antibodies may be engineered to show a similarly enhanced binding to inhibitory over activatory human Fc gamma receptors. Such engineered TNFR-superfamily targeting antibodies also have improved co-stimulatory activity in vivo, in transgenic mice engineered to express human activatory and inhibitory Fc gamma receptors (49).

As outlined above, different types and forms of antibody molecules are included in the invention, and would be known to the person skilled in immunology. It is well known that antibodies used for therapeutic purposes are often modified with additional components which modify the properties of the antibody molecule.

Accordingly, we include that an antibody molecule of the invention or an antibody molecule used in accordance with the invention (for example, a monoclonal antibody molecule, and/or polyclonal antibody molecule, and/or bi-specific antibody molecule) comprises a detectable moiety and/or a cytotoxic moiety.

By "detectable moiety", we include one or more from the group comprising of: an enzyme; a radioactive atom; a fluorescent moiety; a chemiluminescent moiety; a bioluminescent moiety. The detectable moiety allows the antibody molecule to be visualised in vitro, and/or in vivo, and/or ex vivo.

By "cytotoxic moiety", we include a radioactive moiety, and/or enzyme, wherein the enzyme is a caspase, and/or toxin, wherein the toxin is a bacterial toxin or a venom; wherein the cytotoxic moiety is capable of inducing cell lysis.

We further include that the antibody molecule may be in an isolated form and/or purified form, and/or may be PEGylated.

As discussed above, the CDRs of an antibody bind to the antibody target. The assignment of amino acids to each CDR described herein is in accordance with the definitions according to Kabat E A et al. 1991, In "Sequences of Proteins of Immulogical Interest" Fifth Edition, NIH Publication No. 91-3242, pp xv-xvii.

As the skilled person would be aware, other methods also exist for assigning amino acids to each CDR. For example, the International ImMunoGeneTics information system (IMGT(R)) (http://www.imgt.org/ and Lefranc and Lefranc "The Immunoglobulin FactsBook" published by Academic Press, 2001).

In a further embodiment, the antibody molecule of the present invention or used according to the invention is an antibody molecule that is capable of competing with the specific antibodies provided herein, for example antibody molecules comprising any of the amino acid sequences set out in for example SEQ ID NOs: 1-152 for binding to the specific target.

By "capable of competing for" we mean that the competing antibody is capable of inhibiting or otherwise interfering, at least in part, with the binding of an antibody molecule as defined herein to the specific target.

For example, such a competing antibody molecule may be capable of inhibiting the binding of an antibody molecule described herein by at least about 10%; for example at least about 20%, or at least about 30%, at least about 40%, at least about 50%, at least about 60%, at least about 70%, at least about 80%, at least about 90%, at least about 95%, at least about 100% and/or inhibiting the ability of the antibody described herein to prevent or reduce binding to the specific target by at least about 10%; for example at least about 20%, at least about 30%, at least about 40%, at least about 50%, at least about 60%, at least about 70%, at least about 80%, at least about 90%, at least about 95%, or at least about 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in *Antibodies: A Laboratory Manual*, Harlow & Lane, which is incorporated herein by reference (for example, see pages 567 to 569, 574 to 576, 583 and 590 to 612, 1988, CSHL, N.Y., ISBN 0-87969-314-2).

It is well known that an antibody specifically binds a defined target molecule or antigen. That is to say, the antibody preferentially and selectively binds its target and not a molecule which is not a target.

The targets of the antibodies according to the present invention, or of the antibodies used in accordance with the invention, are expressed on the surface of cells, i.e. they are cell surface antigen, which would include an epitope (otherwise known in this context as a cell surface epitope) for the antibody. Cell surface antigen and epitope are terms that would be readily understood by one skilled in immunology or cell biology.

By "cell surface antigen", we include that the cell surface antigen is exposed on the extracellular side of the cell membrane, but may only be transiently exposed on the extracellular side of the cell membrane. By "transiently exposed", we include that the cell surface antigen may be internalized into the cell, or released from the extracellular side of the cell membrane into the extracellular space. The cell surface antigen may be released from the extracellular side of the cell membrane by cleavage, which may be mediated by a protease.

We also include that the cell surface antigen may be connected to the cell membrane, but may only be transiently associated with the cell membrane. By "transiently associated", we include that the cell surface antigen may be released from the extracellular side of the cell membrane into the extracellular space. The cell surface antigen may be released from the extracellular side of the cell membrane by cleavage, which may be mediated by a protease.

We further include that the cell surface antigen may be a peptide, or a polypeptide, or a carbohydrate, or an oligosaccharide chain, or a lipid; and/or an epitope that is present on a protein, or a glycoprotein, or a lipoprotein.

Methods of assessing protein binding are known to the person skilled in biochemistry and immunology. It would be appreciated by the skilled person that those methods could be used to assess binding of an antibody to a target and/or binding of the Fc domain of an antibody to an Fc receptor; as well as the relative strength, or the specificity, or the inhibition, or prevention, or reduction in those interactions. Examples of methods that may be used to assess protein binding are, for example, immunoassays, BIAcore, western blots, radioimmunoassay (RIA) and enzyme-linked immunosorbent assays (ELISAs) (See Fundamental Immunology Second Edition, Raven Press, New York at pages 332-336 (1989) for a discussion regarding antibody specificity).

Accordingly, by "antibody molecule the specifically binds" or "target specific antibody molecule" we include that the antibody molecule specifically binds a target but does not bind to non-target, or binds to a non-target more weakly (such as with a lower affinity) than the target.

We also include the meaning that the antibody specifically binds to the target at least two-fold more strongly, or at least five-fold more strongly, or at least 10-fold more strongly, or at least 20-fold more strongly, or at least 50-fold more strongly, or at least 100-fold more strongly, or at least 200-fold more strongly, or at least 500-fold more strongly, or at least than about 1000-fold more strongly than to a non-target.

Additionally, we include the meaning that the antibody specifically binds to the target if it binds to the target with a $K_d$ of at least about $10^{-1}$ $K_d$, or at least about $10^{-2}$ $K_d$, or at least about $10^{-3}$ $K_d$, or at least about $10^{-4}$ $K_d$, or at least about $10^{-5}$ $K_d$, or at least about $10^{-6}$ $K_d$, or at least about $10^{-7}$ $K_d$, or at least about $10^{-8}$ $K_d$, or at least about $10^{-9}$ $K_d$, or at least about $10^{-10}$ $K_d$, or at least about $10^{-11}$ $K_d$, or at least about $10^{-12}$ $K_d$, or at least about $10^{-13}$ $K_d$, or at least about $10^{-14}$ $K_d$, or at least about $10^{-15}$ $K_d$.

As used herein, the term Treg depleting antibody refers to an antibody that upon administration to a subject, such as a human, specifically binds to a target expressed on the surface of Tregs, wherein this binding results in depletion of Tregs. Thus, a Treg depleting antibody selected from antibodies binding specifically to target belonging to the tumour necrosis factor receptor superfamily (TNFRSF) is an antibody that upon administration to a subject, such as a human, binds to a target belonging to the tumour necrosis factor receptor superfamily expressed on the surface of Tregs and wherein the binding results in depletion of Tregs. In some embodiments, the target belonging to the tumour necrosis factor receptor superfamily is a target that is preferentially expressed on a tumour or in the tumour microenvironment.

In some embodiments, the Treg depleting antibody does not have any immunostimulatory effects in addition to the Treg depleting effects. In some embodiments, the Treg depleting antibody also has an immunostimulatory effect, in addition to the Treg depleting effects; in such embodiments the Treg depleting antibody has a sufficiently poor immunostimulatory activity to allow for enhanced therapeutic activity following sequential administration of a second immunostimulatory antibody.

To decide whether an antibody is a Treg depleting antibody in the meaning of the present invention or not, it is possible to use an in vitro antibody-dependent cellular cytotoxicity (ADCC) or antibody-dependent cellular phagocytosis (ADCP) assay.

An ADCC assay may be done by labelling target cells with calcein AM, followed by the addition of diluting concentrations of Ab. Target cells is then cocultured with human PBMCs at a 50:1 E:T ratio for 4 h at 37° C. The plate is centrifuged at 400 3 g for 5 min to pellet the cells, and the supernatant is transferred to a white 96-well plate. Calcein release is measured using a Varioskan (Thermo Scientific) using an excitation wavelength of 485 nm and emission wavelength, 530 nm. The percentage of maximal release is calculated as follows: % max release=(sample/triton treated) *100.

An ADCP assay may be done by labelling target cells with 5 mM CFSE for 10 min at room temperature before washing in complete media. CFSE-labeled targets is then opsonized with diluting concentrations of Ab before coculturing at a 1:5 E:T ratio with BMDMs in 96-well plates for 1 h at 37° C. BMDMs are then labeled with anti-F4/80-allophycocyanin for 15 min at room temperature and washed with PBS twice. Plates are kept on ice, wells are scraped to collect BMDMs, and phagocytosis is assessed by flow cytometry using a FACSCalibur (BD) to determine the percentage of F4/80+CFSE+ cells within the F4/80+ cell population.

To decide whether an antibody has immunostimulatory effects, it is possible to use an in vitro agonism assay. For such an assay the following generic method may be used. Cell culture is in RPMI 1640 media (Gibco™) supplemented with 10% foetal calf serum, glutamine (2 mM), pyruvate (1 mM), penicillin, and streptomycin (100 IU/mL) at 37° C. in 5% $CO_2$. Fresh PBMCs are labelled with 2 mM carboxyfluorescein succinimidyl ester (CFSE). PBMCs are then cultured in a 24-well plate at 1×10⁷ cells/mL as described by Römer et al (51) for 48 hours prior to mAb stimulation assays. For PBMC stimulation, round-bottomed 96-well plates are wet-coated with 0.01 μg/mL of OKT3 antibody (in-house) in PBS for 4 hours after which excess antibody is discarded and the plates are washed with PBS. 1×10⁵ PBMCs/well are transferred to the plates and stimulated with 5 μg/mL of test mAb. On day 4 or day 5 post-stimulation, cells are labelled with anti-CD8-APC (BioLegend), and anti-CD4-PE (in-house) and proliferation is assessed by CFSE dilution on a FACSCalibur (BD Biosciences).

To decide whether sequential treatment of a Treg deleting and immunostimulatory antibody results in improved therapeutic activity, in vivo assays with immune competent animals bearing tumours and expressing activatory and inhibitory Fc gamma receptors can be used. For such an assay, one described in the examples below may be used, for example as illustrated in FIGS. 1a and 4c.

As used herein, the term immunostimulatory antibody, or immunostimulating antibody, refers to an antibody that upon administration to a subject, such as a human, specifically binds to a target present on the surface of an effector T cell. The binding of the immunostimulatory antibody to the target results in stimulation of an immune response, either directly through agonism (e.g. antibodies to TNF superfamily agonist receptors such as anti-4-1 BB, OX40 antibodies) or indirectly through blockade of inhibitory signals (e.g. through antibody blockade of the PD1/PDL1 axis) through stimulation of an effector T cell. Such an effector T cell can be a CD8+ cell; in such embodiments, the immunostimulatory antibody is a CD8 activating and/or CD8 boosting antibody. Alternatively, or in addition, such an effector T cell can be a CD4+ cell; in such embodiments, the immunostimulatory antibody is a CD4 activating and/or CD4 boosting antibody.

We show herein that different antibodies to different targets of immunostimulatory or co-inhibitory nature, which act in an Fc:FcγR dependent or independent manner can be used for immune stimulation. The immunostimulatory antibody may be an antibody that agonizes an immune stimulatory receptor, such as 4-1BB, expressed on effector T cells, in an Fc:FcγR dependent manner, or an antibody that antagonises an immune checkpoint receptor, such as PD-1, expressed on effector T cells, in an Fc:FcγR-independent manner.

To decide whether an antibody is an immunostimulatory antibody in the meaning of the present invention, it is possible to use an in vitro assay that demonstrates T cell proliferation in response to mAb. The assays described above may be used for this purposes.

To decide whether an antibody lacks Treg depleting effects or has a poor Treg depleting effect, it is possible to use in vitro phagocytosis assays or in vivo depletion studies. The assays described in the examples may be used for this purposes. For example, groups of test mice receive tumour on day 0. When tumours are palpable (or at appropriate stage for tumour model) mice receive the mAb i.v. followed by 3 further administrations i.p. every other day (200 μg final dose, or as established for mAb). Mice are then sacrificed 1 or 2 day(s) after the final mAb administration and the spleen and tumour are analysed by flow cytometry for TIL content and the frequency of Foxp3+ cells within the CD4+ population in the tumour plotted and spleen (control tissue).

In some embodiments, the Treg depleting antibody is a human antibody.

In some embodiments, the Treg depleting antibody is a humanized antibody.

In some embodiments, the immunostimulatory antibody is a human antibody.

In some embodiments, the immunostimulatory antibody is a humanized antibody.

The Treg depleting antibody and the immunostimulatory antibody used in combination in accordance with the present invention may both comprise the same CDRs since the depleting/immunostimulatory effects may be adjusted by modifications of other parts of the antibody, as also discussed above.

For example, a Treg depleting antibody may be obtained by using an antibody in the form of a human IgG1 antibody; accordingly, in some embodiments, the Treg depleting antibody is a human IgG1 antibody. A Treg depleting antibody may also be obtained by using an antibody in the form of a human IgG1 antibody showing improved binding to one or several activatory Fc receptors and/or being engineered for improved binding to one or several activatory Fc receptors; accordingly, in some embodiments, the Treg depleting antibody is an Fc-engineered human IgG1 antibody. A Treg depleting antibody may also be obtained by using murine or a humanized murine IgG2a antibody, and accordingly, in some embodiments, the Treg depleting antibody is a humanized murine IgG2a antibody.

Furthermore, an immunostimulatory antibody may be obtained by using an antibody in the form of a human IgG2 antibody, such as a human IgG2b antibody, or in the form of a human IgG4 antibody. Thus, in some embodiments the immunostimulatory antibody is a human IgG2 antibody. In some embodiments the immunostimulatory antibody is a human IgG2b antibody. In some embodiments the immunostimulatory antibody is a human IgG4 antibody. An immunostimulatory antibody may also be obtained by using a murine or a humanized murine IgG1 antibody, and in some embodiments the immunostimulatory antibody is a humanized murine IgG1 antibody.

In some embodiments, the immunostimulatory antibody is and antibody showing enhanced binding to inhibitory over activatory Fcγ receptors. In some embodiments, the immunostimulatory antibody is an antibody showing enhanced binding to human FcγRIIB over activatory Fcγ receptors.

In some embodiments, the immunostimulatory antibody is engineered for enhanced binding to inhibitory over activatory Fcγ receptors. In some embodiments, the immunostimulatory antibody is engineered for enhanced binding to human FcγRIIB over activatory Fcγ receptors.

The target that the Treg depleting antibody of the present invention or the Treg depleting antibody used in accordance with the present invention binds to may be selected from the group consisting of targets belonging to the TNFRS. The target belonging to the TNFRS may be selected from the group consisting of 4-1BB, OX40, and TNFR2.

The target that the Treg depleting antibody of the present invention or the Treg depleting antibody used in accordance with the present invention binds to may alternatively be selected from the group consisting of ICOS, GITR, CTLA-4, CD25, and neuroplin-1. In some embodiments, the target is not CD25.

The target that the immunostimulatory antibody of the present invention or the immunostimulatory used in accordance with the present invention binds to may be selected from the group consisting of 4-1BB and OX40.

The target that the immunostimulatory antibody of the present invention or the Treg depleting antibody used in accordance with the present invention binds to may alternatively be selected from the group consisting of ICOS, GITR, CTLA-4, TNFR2, CD25 and PD-1. In some embodiments, the target is not CD25.

In some embodiments of the present invention, at least one target is 4-1BB, which is also denoted CD137 and tumour necrosis factor receptor superfamily member 9 (TNFRSF9). 4-1BB is expressed on Tregs following activation of CD4+ and CD8+ T cells and its ligation is required for optimal protective CD8 T cell responses against viruses and B cell lymphoma in mice (11, 12). Anti-4-1BB specific antibodies enhance the proliferation and survival of antigen-stimulated T cells in vitro and, similar to anti-CD40, anti-4-1 BB mAb promote anti-tumour immunity in pre-clinical cancer models dependent largely on CD8 T cells (12, 13). 4-1BB is a downstream target of the Treg lineage-defining transcription factor Foxp3, is expressed on resting Treg cells and is upregulated on Treg activation (14, 15), and it is possible therefore that anti-4-1BB may act in part through the depletion of Treg cells. Whether anti-4-1 BB antibody is a depleting or a stimulating antibody is likely to depend on its FcγR usage and in the work leading to the present invention, the inventors carried out in vitro and in vivo experiments to explore the optimal isotype for a therapeutic anti-4-1 BB mAb in a tumour setting.

We found that although a mIgG1 isotype mAb exerted superior agonistic activity and direct immune-stimulation of CD8+ T cells compared with a mIgG2a version of the same specificity, in established solid tumour settings the mIgG2a mAb provided optimal therapeutic activity. We found that the potency of the mIgG2a mAb is due to intratumoural Treg depletion. However when depletion was prevented, in mice lacking activatory FcγR, the therapeutic potential of the mIgG2a was retained. Under these conditions mIgG2a was converted to an agonist by engaging the inhibitory FcγRIIB. Further to this we established that depletion and agonism are competing mechanisms and that engaging both simultaneously led to reduced efficacy. This blunting of activity could be overcome through sequential administration of Treg depleting and then immunostimulatory isotypes or through Fc engineering to produce a dual-activity anti-4-1 BB mAb posessing optimal FcγR depleting capacity together with FcγR independent agonism. Together, these results demonstrate that immunomodulatory mAb with the same target specificity can utilise different mechanisms to mediate therapy and that their optimal use depends on both isotype, the local FcγR repertoire, abundance and function of immune suppressor and effector cells and their relative and absolute expression of target, in the tumor microenvironment. Importantly, our results further demonstrate that temporal administration of immunomodulatory mAb, with complementary, but competing, mechanisms-of-action may be used to optimize outcome and further that it is possible through mAb engineering to generate a single agent capable of harnessing multiple mechanisms to deliver enhanced therapeutic efficacy. These results have implications for the administration of existing and in-development immunomodulatory mAb, and for the design of next generation immunomodulatory antibodies.

In some embodiments, the Treg depleting antibody molecule is an anti-4-1 BB antibody molecule selected from the group presented in Table 1 below.

In some embodiments, the Treg depleting antibody molecule is an anti-4-1 BB antibody molecule selected from the group consisting of antibody molecules comprising 1-6 of the CDRs from each group selected from of SEQ ID. Nos: 1-6, SEQ ID. Nos: 9-14, SEQ ID. Nos: 17-22, SEQ ID. Nos: 25-30, SEQ ID. Nos: 33-38, SEQ ID. Nos: 41-46, SEQ ID. Nos: 49-54, SEQ ID. Nos: 57-62, SEQ ID. Nos: 65-70, SEQ ID. Nos: 153-158 and SEQ ID. Nos: 163-168.

In some embodiments, the Treg depleting antibody molecule is an anti-4-1 BB antibody molecule selected from the group consisting of antibody molecules comprising the 6 CDRs selected from SEQ ID. Nos: 1-6, SEQ ID. Nos: 9-14, SEQ ID. Nos: 17-22, SEQ ID. Nos: 25-30, SEQ ID. Nos: 33-38, SEQ ID. Nos: 41-46, SEQ ID. Nos: 49-54, SEQ ID. Nos: 57-62, SEQ ID. Nos: 65-70, SEQ ID. Nos: 153-158 and SEQ ID. Nos: 163-168.

In some embodiments, the Treg depleting antibody molecule is an anti-4-1BB antibody molecule selected from the group consisting of antibody molecules comprising a VH selected from the group consisting of SEQ ID. Nos: 7, 15, 23, 31, 39, 47, 55, 63, 71, 159, 161 and 169.

In some embodiments, the Treg depleting antibody molecule is an anti-4-1 BB antibody molecule selected from the group consisting of antibody molecules comprising a VL selected from the group consisting of SEQ ID. Nos: 8, 16, 24, 32, 40, 48, 56, 64, 72, 160, 162 and 170.

In some embodiments, the Treg depleting antibody molecule is an anti-4-1 BB antibody molecule selected from the group consisting of antibody molecules comprising a VH and a VL selected from the group consisting of SEQ ID. Nos: 7-8, 15-16, 23-24, 31-32, 39-40, 47-48, 55-56, 63-64, 71-72, 159-160, 161-162 and 169-170.

In some embodiments, the immunostimulatory antibody molecule is an anti-4-1 BB antibody molecule selected from the group presented in Table 1 below.

In some embodiments, the immunostimulatory antibody molecule is an anti-4-1 BB antibody molecule selected from the group consisting of antibody molecules comprising 1-6 of the CDRs from each group SEQ ID. Nos: 1-6, SEQ ID. Nos: 9-14, SEQ ID. Nos: 17-22, SEQ ID. Nos: 25-30, SEQ ID. Nos: 33-38, SEQ ID. Nos: 41-46, SEQ ID. Nos: 49-54, SEQ ID. Nos: 57-62, SEQ ID. Nos: 65-70, SEQ ID. Nos: 153-158 and SEQ ID. Nos: 163-168.

In some embodiments, the immunostimulatory antibody molecule is an anti-4-1 BB antibody molecule selected from the group consisting of antibody molecules comprising the 6 CDRs selected from SEQ ID. Nos: 1-6, SEQ ID. Nos: 9-14, SEQ ID. Nos: 17-22, SEQ ID. Nos: 25-30, SEQ ID. Nos: 33-38, SEQ ID. Nos: 41-46, SEQ ID. Nos: 49-54, SEQ ID. Nos: 57-62, SEQ ID. Nos: 65-70, 153-158 and SEQ ID. Nos: 163-168.

In some embodiments, the immunostimulatory antibody molecule is an anti-4-1BB antibody molecule selected from the group consisting of antibody molecules comprising a VH selected from the group consisting of SEQ ID. Nos: 7, 15, 23, 31, 39, 47, 55, 63, 71, 159, 161 and 169.

In some embodiments, the immunostimulatory antibody molecule is an anti-4-1 BB antibody molecule selected from the group consisting of antibody molecules comprising a VL selected from the group consisting of SEQ ID. Nos: 8, 16, 24, 32, 40, 48, 56, 64, 72, 160, 162 and 170.

In some embodiments, the immunostimulatory antibody molecule is an anti-4-1 BB antibody selected from the group consisting of antibody molecules comprising a VH and VL selected from the group consisting of SEQ ID. Nos: 7-8, 15-16, 23-24, 31-32, 39-40, 47-48, 55-56, 63-64, 71-72, 159-160, 161-162 and 169-170.

TABLE 1

4-1BB antibodies

| Antibody | | Sequence | SEQ. ID. NO: |
|---|---|---|---|
| 2-A11 | VH-CDR1 | FSSNEMSWVRQAPG | 1 |
| | VH-CDR2 | SGSIGYADSVKGR | 2 |
| | VH-CDR3 | ARDRMVRGVSNWFDP | 3 |
| | VL-CDR1 | CTGSSSNIGAGYDVN | 4 |
| | VL-CDR2 | GNFNRPS | 5 |
| | VL-CDR3 | CQSYDSRLSGSV | 6 |
| | VH | EVQLLESGGGLVQPGGSLRLSCAASGFTFSSNEMSWVR-QAPGKGLEWVSGISWNSGSIGYADSVKGRFTISRD-NSKNTLYLQMNSLRAEDTAVYYCARDRMVRGVSNWFDPWGQGTLVTVSS | 7 |
| | VL | QSVLTQPPSASGTPGQRVTISCTGSSSNI-GAGYDVNWYQQLPGTAPKLLIYGNFNRPSGVPDRFSG-SKSGTSASLAISGLR-SEDEADYYCQSYDSRLSGSVFGGGTKLTVLG | 8 |
| 2-D01 | VH-CDR1 | FTFGDYAVAWFRQAPG | 9 |
| | VH-CDR2 | ITDYADPVKGR | 10 |
| | VH-CDR3 | ARNYGGYYYYGMDV | 11 |
| | VL-CDR1 | CTGSSSNIGAGYDVH | 12 |
| | VL-CDR2 | GTAPKLLIYGTNNRPS | 13 |
| | VL-CDR3 | CAAWDGSLSGRV | 14 |
| | VH | EVQLLESGGGLVQPGGSLRLSCAASGFTFGDYAVAWFR-QAPGKGLEWVSIVSGSTITDYADPVKGRFTISRD-NSKNTLYLQMNSLRAEDTAVYYCARNYGGYYYYG-MDVWGQGTLVTVSS | 15 |
| | VL | QSVLTQPPSASGTPGQRVTISCTGSSSNI-GAGYDVHWYQQLPGTAPKLLIYGTNNRPSGVPDRFSG-SKSGTSASLAISGLR-SEDEADYYCAAWDGSLSGRVFGGGTKLTVLG | 16 |
| 5-A09 | VH-CDR1 | FSSNYMSWVRQAPG | 17 |
| | VH-CDR2 | SSISSGSSYIYYADSVKGR | 18 |
| | VH-CDR3 | AKEPPAYREGIDY | 19 |
| | VL-CDR1 | CSGSSSNIANNYVS | 20 |
| | VL-CDR2 | DNTNRPS | 21 |
| | VL-CDR3 | CASWDDSLSGPV | 22 |
| | VH | EVQLLESGGGLVQPGGSLRLSCAASGFTFSSNYMSWVR-QAPGKGLEWVSSISSGSSYIYYADSVKGRFTISID-NSKNTLYLQMNSLRAEDTAVYYCAKEP-PAYREGIDYWGQGTLVTVSS | 23 |
| | VL | QSVLTQPPSASGTPGQRVTISCSGSSSNI-ANNYVSWYQQLPGTAPKLLIYDNTNRPSGVPDRFSG-SKSGTSASLAISGLR-SEDEADYYCASWDDSLSGPVFGGGTKLTVLG | 24 |
| 6-A01 | VH-CDR1 | FSSYSMNWVRQAPG | 25 |
| | VH-CDR2 | AVISYDGSNKYYADSMKGR | 26 |
| | VH-CDR3 | ARDSYLGWCPAGSCTGIDY | 27 |
| | VL-CDR1 | CSGSSSNIGNNAVN | 28 |
| | VL-CDR2 | YDDLLPS | 29 |
| | VL-CDR3 | CAAWDDSLSGWV | 30 |
| | VH | EVQLLESGGGLVQPGGSLRLSCAASGFTFSSYSMNWVR-QAPGKGLEWVAVISYDGSNKYYADSMKGRFTISRD-NSKNTLYLQMNSLRAEDTAVYYCARDSYLGWCPAGSCT-GIDYWGQGTLVTVSS | 31 |
| | VL | QSVLTQPPSASGTPGQRVTISCSGSSS-NIGNNAVNWYQQLPGTAPKLLIYYDDLLPSGVPDRFSG-SKSGTSASLAISGLR-SEDEADYYCAAWDDSLSGWVFGGGTKLTVLG | 32 |
| 6-A11 | VH-CDR1 | FSNYVLTWVRQSPG | 33 |
| | VH-CDR2 | SGSGYNTYHADSVKGR | 34 |
| | VH-CDR3 | ARAAYDSSGYADAFDI | 35 |
| | VL-CDR1 | CSGSSSNIGSNYVY | 36 |
| | VL-CDR2 | GDNRRPS | 37 |
| | VL-CDR3 | CAAWDDSLNGWV | 38 |
| | VH | EVQLLESGGGLVQPGGSLRLSCAASGFTFSNYVLT-WVRQSPGKGLEWVSGISGSGYNTYHADSVKGRFTISRD-NSKNTLYLQMNSLRAEDTAVYYCARAAYDSSGYADAFD-IWGQGTLVTVSS | 39 |
| | VL | QSVLTQPPSASGTPGQRVTISCSGSSSNIGSNYVY-WYQQLPGTAPKLLIYGDNRRPSGVPDRFSG-SKSGTSASLAISGLR-SEDEADYYCAAWDDSLNGWVFGGGTKLTVLG | 40 |

TABLE 1-continued 4-1BB antibodies

| Antibody | | Sequence | SEQ. ID. NO: |
|---|---|---|---|
| 6-F05 | VH-CDR1 | RLSCAASGFTFSDYYMSWVRQAPG | 41 |
| | VH-CDR2 | ANIKQDGSEKYYGDSATGR | 42 |
| | VH-CDR3 | AKEERIGTYYY | 43 |
| | VL-CDR1 | CSGSSFNIGSNYVY | 44 |
| | VL-CDR2 | KNNQRPS | 45 |
| | VL-CDR3 | CAAWDDSLNGQV | 46 |
| | VH | EVQLLESGGGLVQPGGSLRLSCAASGFTFSDYYMSWVR-QAPGKGLEWVANIKQDGSEKYYGDSATGRFTISRD-NSKNTLYLQMNSLRAEDTAVYYCAKEERIGTYYYWGQGTLVTVSS | 47 |
| | VL | QSVLTQPPSASGTPGQRVTISCSGSSFNIGSNYVY-WYQQLPGTAPKLLIYKNNQRPSGVPDRFSG-SKSGTSASLAISGLR-SEDEADYYCAAWDDSLNGQVFGGGTKLTVLG | 48 |
| 6-H05 | VH-CDR1 | FSDYYMTWIRQAPG | 49 |
| | VH-CDR2 | SSISSSSSYIYYADSVKGR | 50 |
| | VH-CDR3 | ASTQTPYGSGNYPIYYYYGMDV | 51 |
| | VL-CDR1 | CSGSRSNIRSNSVS | 52 |
| | VL-CDR2 | GNSNRPS | 53 |
| | VL-CDR3 | CGTWDDRLNRPV | 54 |
| | VH | EVQLLESGGGLVQPGGSLRLS-CAASGFTFSDYYMTWIRQAPGKGLEWVSSISSSSSYIY-YADSVKGRFTISRD-NSKNTLYLQMNSLRAEDTAVYYCASTQTPYGSGNYPIY-YYYGMDVWGQGTLVTVSS | 55 |
| | VL | QSVLTQPPSASGTPGQRVTISCSGSRSNIRSNSVSWYQQLPGTAPKLLIYGNSNRPSGVPDRFSGSKSGTSASLAISGLR-SEDEADYYCGTWDDRLNRPVFGGGTKLTVLG | 56 |
| 7-B08 | VH-CDR1 | FSSYWMSWVRQTPG | 57 |
| | VH-CDR2 | SAINAAGDFQSYADSVRGR | 58 |
| | VH-CDR3 | ARGDGYNYFDI | 59 |
| | VL-CDR1 | CSGSSSNIGSNYVY | 60 |
| | VL-CDR2 | GNSNRPS | 61 |
| | VL-CDR3 | CQSYDSSLSGLV | 62 |
| | VH | EVQLLESGGGLVQPGGSLRLS-CAASGFTFSSYWMSWVRQTPGKGLEWVSAINAAGDFQSYADSVRGRFTISRDNSKNTLYLQMNSLRAEDTAMYYCAR-GDGYNYFDIWGQGTLVTVSS | 63 |
| | VL | QSVLTQPPSASGTPGQRVTISCSGSSSNIGSNYVY-WYQQLPGTAPKLLIYGNSNRPSGVPDRFSG-SKSGTSASLAISGLR-SEDEADYYCQSYDSSLSGLVFGGGTKLTVLG | 64 |
| 6-A06 | VH-CDR1 | FSRYEMNWVRQAPG | 65 |
| | VH-CDR2 | SGINWNGGSTGYADSVKGR | 66 |
| | VH-CDR3 | ARHRNPDPLDAFDI | 67 |
| | VL-CDR1 | CTGSSSNIGAGYDVH | 68 |
| | VL-CDR2 | SNNQRPS | 69 |
| | VL-CDR3 | CASYTSISTVL | 70 |
| | VH | EVQLLESGGGLVQPGGSLRLSCAASGFTFSRYEMNWVR-QAPGKGLEWVSGINWNGGSTGYADSVKGRFTISRD-NSKNTLYLQMNSLRAEDTAMYYCARHRNPDPLDAFD-IWGQGTLVTVSS | 71 |
| | VL | QSVLTQPPSASGTPGQRVTISCTGSSSNI-GAGYDVHWYQQLPGTAPKLLIYSNNQRPSGVPDRFSG-SKSGTSASLAISGLR-SEDEADYYCASYTSISTVLFGGGTKLTVLG | 72 |
| 5-B02 | VH-CDR1 | FSSYAMHWVRQAPG | 153 |
| | VH-CDR2 | AVISYDGSNKYYADSVKGR | 154 |
| | VH-CDR3 | TRPLKDDPDAFDI | 155 |
| | VL-CDR1 | CSGSSSNIGSYAVN | 156 |
| | VL-CDR2 | RNNQRPS | 157 |
| | VL-CDR3 | CFSYAGGNTWV | 158 |
| | VH | EVQLLESGGGLVQPGGSLRLSCAASGFT<u>FSSYAMHWVR-QAPG</u>KGLEWVA<u>VISYDGSNKYYADSVKGR</u>FTISRD-NSKNTLYLQMNSLRAEDTAVYYC<u>TRPLKDDPDAFD-IW</u>GQGTLVTVSS | 159 |
| | VL | QSVLTQPPSASGTPGQRVTIS<u>CSGSSSNIGSYAVN</u>WYQQLPGTAP-KLLIY<u>RNNQRPS</u>GVPDRFSGSKSGTSASLAISGLR-SEDEADYY<u>CFSYAGGNTWV</u>FGGGTKLTVLG | 160 |

TABLE 1-continued 4-1BB antibodies

| Antibody | | Sequence | SEQ. ID. NO: |
|---|---|---|---|
| 2-C08 | VH-CDR1 | FSSYEMNWVRQAPG | 163 |
| | VH-CDR2 | SAISGSAGSTYYADSVKGR | 164 |
| | VH-CDR3 | ATYPKEKTLHGGRYPYYGLDL | 165 |
| | VL-CDR1 | CSGSSSNIGSNTVN | 166 |
| | VL-CDR2 | DNNKRPL | 167 |
| | VL-CDR3 | CATWDDSLSGPV | 168 |
| | VH | EVQLLESGGGLVQPGGSLRLSCAASGFTFSRYEMNWVR-QAPGKGLEWVSGINWNGGSTGYADSVKGRFTISRD-NSKNTLYLQMNSLRAEDTAMYYCARHRNPDPLDAFD-IWGQGTLVTVSS | 169 |
| | VL | QSVLTQPPSASGTPGQRVTISCTGSSSNI-GAGYDVHWYQQLPGTAPKLLIYSNNQRPSGVPDRFSG-SKSGTSASLAISGLR-SEDEADYYCASYTSISTVLFGGGTKLTVLG | 170 |
| SAP3-6 | VH | MKCSWVMFFLMAVVTGVNSEVQLQQSGAELVKP-GASVKLSCTASGFNIKDSYMYWVKQRPEQGLEWIGRI-YPANGDTKYDPKFQGKATITADTSS-NTAYLQLSSLASEDTAVYYCTRGYG-SNFFDYWGQGTTLTVSS | 161 |
| | VL | METDTLLLWVLLLWVPGSTGDIVLTQSPASLAVSLGQRT-TISCRASESVDSYGNSFMHWYQQKPGQPPKLLIYRASN-LESGIPARFSGSGSRTDFTLTINPVE-ADDVATYYCQQSNEDPFTFGGGTKLEIK | 162 |

In some embodiments, the Treg depleting antibody molecule is an anti-OX40 antibody molecule selected from the group presented in Table 2 below.

In some embodiments, the Treg depleting antibody molecule is an anti-OX40 antibody molecule selected from the group consisting of antibody molecules comprising 1-6 of the CDRs from each group selected from SEQ ID. Nos: 73-78, SEQ ID. Nos:81-86, SEQ ID. Nos:89-94, SEQ ID. Nos:97-102, SEQ ID. Nos:105-110, SEQ ID. Nos:113-118, SEQ ID. Nos:121-126, SEQ ID. Nos:129-134, SEQ ID. Nos:137-142, SEQ ID. Nos:145-150 and SEQ ID. Nos:171-176.

In some embodiments, the Treg depleting antibody molecule is an anti-OX40 antibody molecule selected from the group consisting of antibody molecules comprising the 6 CDRs from each group selected from SEQ ID. Nos: 73-78, SEQ ID. Nos:81-86, SEQ ID. Nos:89-94, SEQ ID. Nos:97-102, SEQ ID. Nos:105-110, SEQ ID. Nos:113-118, SEQ ID. Nos:121-126, SEQ ID. Nos:129-134, SEQ ID. Nos: 137-142, SEQ ID. Nos:145-150 and SEQ ID. Nos:171-176.

In some embodiments, the Treg depleting antibody molecule is an anti-OX40 antibody molecule selected from the group comprising a VH selected from the group consisting of SEQ ID. Nos: 79, 87, 95, 103, 111, 119, 127, 135, 143, 151 and 177.

In some embodiments, the Treg depleting antibody molecule is an anti-OX40 antibody molecule selected from the group consisting of antibody molecules comprising a VL selected from the group consisting of SEQ ID. Nos: 80, 88, 96, 104, 112, 120, 128, 136, 144, 152 and 178.

In some embodiments, the Treg depleting antibody molecule is an anti-OX40 antibody molecule selected from the group consisting of antibody molecules comprising a VH and a VL selected from the group consisting of SEQ ID. Nos: 79-80, 87-88, 95-96, 103-104, 111-112, 119-120, 127-128, 135-136, 143-144, 151-152 and 177-178.

In some embodiments, the immunostimulatory antibody molecule is an anti-OX40 antibody molecule selected from the group presented in Table 2 below.

In some embodiments, the immunostimulatory antibody molecule is an anti-OX40 antibody molecule selected from the group consisting of antibody molecules comprising 1-6 of the CDRs from each group selected from SEQ ID. Nos: 73-78, SEQ ID. Nos: 81-86, SEQ ID. Nos: 89-94, SEQ ID. Nos: 97-102, SEQ ID. Nos: 105-110, SEQ ID. Nos: 113-118, SEQ ID. Nos: 121-126, SEQ ID. Nos: 129-134, SEQ ID. Nos: 137-142, SEQ ID. Nos: 145-150 and SEQ ID. Nos: 171-176.

In some embodiments, the immunostimulatory antibody molecule is an anti-OX40 antibody molecule selected from the group consisting of antibody molecules comprising the 6 CDRs selected from SEQ ID. Nos: 73-78, SEQ ID. Nos: 81-86, SEQ ID. Nos: 89-94, SEQ ID. Nos: 97-102, SEQ ID. Nos: 105-110, SEQ ID. Nos: 113-118, SEQ ID. Nos: 121-126, SEQ ID. Nos: 129-134, SEQ ID. Nos: 137-142, 145-150 and SEQ ID. Nos: 171-176.

In some embodiments, the immunostimulatory antibody molecule is an anti-OX40 antibody molecule selected from the group consisting of antibody molecules comprising a VH selected from the group consisting of SEQ ID. Nos: 79, 87, 95, 103, 111, 119, 127, 135, 143, 151 and 177.

In some embodiments, the immunostimulatory antibody molecule is an anti-OX40 antibody molecule selected from the group consisting of antibody molecules comprising a VL selected from the group consisting of SEQ ID. Nos: 80, 88, 96, 104, 112, 120, 128, 136, 144, 152 and 178.

In some embodiments, the immunostimulatory antibody molecule is an anti-OX40 antibody molecule selected from the group consisting of antibody molecules comprising a VH and a VL selected from the group consisting of SEQ ID. Nos: 79-80, 87-88, 95-96, 103-104, 111-112, 119-120, 127-128, 135-136, 143-144, 151-152 and 177-178.

TABLE 2

OX40 antibodies

| Antibody | | | SEQ. ID. NO: |
|---|---|---|---|
| 1-D08 | VH-CDR1 | FSSYAMSWVRQAPG | 73 |
| | VH-CDR2 | SGINGYGDTPKDADSVKGR | 74 |
| | VH-CDR3 | ATLYCGGGGCYPDS | 75 |
| | VL-CDR1 | CTGSRSNIGAGYDVH | 76 |
| | VL-CDR2 | DYDEQPS | 77 |
| | VL-CDR3 | CAAWDDSLNGVV | 78 |
| | VH | EVQLLESGGGLVQPGGSLRLSCAASGFTFSSYAMSWVR-QAPGKGLEWVSGINGYGDTPKDADSVKGRFTISRD-NSKNTLYLQMNSLRAEDTAVYY-CATLYCGGGGCYPDSWGQGTLVTVSS | 79 |
| | VL | QSVLTQPPSASGTPGQRVTISCTGSRSNI-GAGYDVHWYQQLPGTAPKWYDYDEQPSGVPDRFSG-SKSGTSASLAISGLR-SEDEADYYCAAWDDSLNGVVFGGGTKLTVLG | 80 |
| 2-A02 | VH-CDR1 | FSGYWMTWVRQAPG | 81 |
| | VH-CDR2 | SSISSSSSYIYYADSVKGR | 82 |
| | VH-CDR3 | TSSNPFYGMDV | 83 |
| | VL-CDR1 | CSGSSSNIGNNYVS | 84 |
| | VL-CDR2 | YDDLLPS | 85 |
| | VL-CDR3 | CAAWDDSLNGGV | 86 |
| | VH | EVQLLESGGGLVQPGGSLRLSCAASGFTFSGYWMTWVR-QAPGKGLEWVSSISSSSSYIYYADSVKGRFTISRD-NSKNTLYLQMNSLRAEDTAVYYCTSSNPFYG-MDVWGQGTLVTVSS | 87 |
| | VL | QSVLTQPPSASGTPGQRVTISCSGSSS-NIGNNYVSWYQQLPGTAPKLLIYYDDLLPSGVPDRFSG-SKSGTSASLAISGLR-SEDEADYYCAAWDDSLNGGVFGGGTKLTVLG | 88 |
| 2-D07 | VH-CDR1 | FSDYYMSWVRQAPG | 89 |
| | VH-CDR2 | SSITGTAGLTYNADSVKGR | 90 |
| | VH-CDR3 | ARMDWGYGNFDY | 91 |
| | VL-CDR1 | CSGSSSNIGSYTVN | 92 |
| | VL-CDR2 | GNNNRPS | 93 |
| | VL-CDR3 | CATWDDSLSGPV | 94 |
| | VH | EVQLLESGGGLVQPGGSLRLSCAASGFTFSDYYMSWVR-QAPGKGLEWVSSITGTAGLTYNADSVKGRFTISRD-NSKNTLYLQMNSLRAEDTAVYYCARMDWGYG-NFDYVVGQGTLVTVSS | 95 |
| | VL | QSVLTQPPSASGTPGQRVTISCSGSSS-NIGSYTVNWYQQLPGTAPKLLIYGNNNRPSGVPDRFSG-SKSGTSASLAISGLRSEDEADYY-CATWDDSLSGPVFGGGTKLTVLG | 96 |
| 2-F02 | VH-CDR1 | FSDYEMNWVRQAPG | 97 |
| | VH-CDR2 | AVISYDGSNKYYADSVKGR | 98 |
| | VH-CDR3 | AANSPFDP | 99 |
| | VL-CDR1 | CTGSSSNIGAGYDVH | 100 |
| | VL-CDR2 | NDNVRPS | 101 |
| | VL-CDR3 | CAAWDANLSGWV | 102 |
| | VH | EVQLLESGGGLVQPGGSLRLSCAASGFTFSDYEMNWVR-QAPGKGLEWVAVISYDGSNKYYADSVKGRFTISRD-NSKNTLYLQMNSLRAEDTAVYYCAANSPFDPWGQGTLVTVSS | 103 |
| | VL | QSVLTQPPSASGTPGQRVTISCTGSSSNI-GAGYDVHWYQQLPGTAPKLLIYNDNVRPSGVPDRFSG-SKSGTSASLAISGLRSEDEADYYCAAW-DANLSGWVFGGGTKLTVLG | 104 |
| 2-F10 | VH-CDR1 | FSSYEMNWVRQAPG | 105 |
| | VH-CDR2 | AVISYDGSNKYYADSVKGR | 106 |
| | VH-CDR3 | AANSPFDP | 107 |
| | VL-CDR1 | CTGSSSNIGAGYDVH | 108 |
| | VL-CDR2 | SNNQRPS | 109 |
| | VL-CDR3 | CAAWDDSLSGWV | 110 |
| | VH | EVQLLESGGGLVQPGGSLRLSCAASGFTFSSYEMNWVR-QAPGKGLEWVAVISYDGSNKYYADSVKGRFTISRD-NSKNTLYLQMNSLRAEDTAMYYCAANSPFDPWGQGTLVTVSS | 111 |
| | VL | QSVLTQPPSASGTPGQRVTISCTGSSSNI-GAGYDVHWYQQLPGTAPKLFIYSNNQRPSGVPDRFSG-SKSGTSASLAISGLR-SEDEADYYCAAWDDSLSGWVFGGGTKLTVLG | 112 |

TABLE 2-continued

OX40 antibodies

| Antibody | | | SEQ. ID. NO: |
|---|---|---|---|
| 5-D11 | VH-CDR1 | FDNHWMSWVRQAPG | 113 |
| | VH-CDR2 | SSISSSSSYIYYADSVKGR | 114 |
| | VH-CDR3 | AREDWSFDL | 115 |
| | VL-CDR1 | CSGSSSNIGNNAVN | 116 |
| | VL-CDR2 | GNSNRPS | 117 |
| | VL-CDR3 | CQTFDVSQNAWV | 118 |
| | VH | EVQLLESGGGLVQPGGSLRLS-CAASGFTFDNHWMSWVRQAPGKGLEWVSSISSSSSYIY-YADSVKGRSTISRD-NSKNTLYLQMNSLRAEDTAMYYCAREDWS-FDLWGQGTLVTVSS | 119 |
| | VL | QSVLTQPPSASGTPGQRVTISCSGSSS-NIGNNAVNWYQQLPGTAPKLLIYGNSNRPSGVPDRFSG-SKSGTSASLAISGLR-SEDEADYYCQTFDVSQNAWVFGGGTKLTVLG | 120 |
| 6-D12 | VH-CDR1 | FSNSDMNWVRQAPG | 121 |
| | VH-CDR2 | SAISNSGDGTYYADSVKGR | 122 |
| | VH-CDR3 | REKTVVGAAFDI | 123 |
| | VL-CDR1 | CTGSSSNIGAGYDVH | 124 |
| | VL-CDR2 | SQNLRPS | 125 |
| | VL-CDR3 | CQSYDSSLSGSV | 126 |
| | VH | EVQLLESGGGLVQPGGSLRLSCAASGFTFSNSDMNWVR-QAPGKGLEWVSAISNSGDGTYYADSVKGRFTISRD-NSKNTLYLQMNSLRAEDTAVYYCAREKTWGAAFD-IWGQGTLVTVSS | 127 |
| | VL | QSVLTQPPSASGTPGQRVTISCTGSSSNI-GAGYDVHWYQQLPGTAPKLLIYSQNLRPSGVPDRFSG-SKSGTSASLAISGLR-SEDEADYYCQSYDSSLSGSVFGGGTKLTVLG | 128 |
| 6-F03 | VH-CDR1 | FSDYTMNWVRQAPG | 129 |
| | VH-CDR2 | SAISGSGGSTYYPDSVKGR | 130 |
| | VH-CDR3 | ARGGGYWPFDP | 131 |
| | VL-CDR1 | CSGSSSTIGNNAIN | 132 |
| | VL-CDR2 | RDNQRPS | 133 |
| | VL-CDR3 | CQSYDSSLRVVV | 134 |
| | VH | EVQLLESGGGLVQPGGSLRLSCAASGFTFSDYTMNWVR-QAPGKGLEWVSAISGSGGSTYYPDSVKGRFTISRD-NSKNTLYLQMNSLRAEDTAVYYCARGG-GYWPFDPWGQGTLVTVSS | 135 |
| | VL | QSVLTQPPSASGTPGQRVTISCSGSSSTIGNNAIN-WYQQLPGTAPKLLIYRDNQRPSGVPDRFSG-SKSGTSASLAISGLR-SEDEADYYCQSYDSSLRVVVFGGGTKLTVLG | 136 |
| 6-F04 | VH-CDR1 | FSSYAMSWVRQAPG | 137 |
| | VH-CDR2 | SSISSSSSYIYYADSVKGR | 138 |
| | VH-CDR3 | VRGTSLDAFDI | 139 |
| | VL-CDR1 | CSGSSSNIGNTYVS | 140 |
| | VL-CDR2 | YDDLLPS | 141 |
| | VL-CDR3 | CAAWDDSLSGVV | 142 |
| | VH | EVQLLESGGGLVQPGGSLRLSCAASGFTFSSYAMSWVR-QAPGKGLEWVSSISSSSSYIYYADSVKGRFTISRD-NSKNTLYLQMNSLRAEDTAVYYCVRGTSLDAFD-IWGQGTLVTVSS | 143 |
| | VL | QSVLTQPPSASGTPGQRVTISCSGSSSNIGN-TYVSWYQQLPGTAPKLLIYYDDLLPSGVPDRFSG-SKSGTSASLAISGLR-SEDEADYYCAAWDDSLSGVVFGGGTKLTVLG | 144 |
| 7-A07 | VH-CDR1 | FSDYYMSWIRQAPG | 145 |
| | VH-CDR2 | SSISSSSSYISYADSMKGR | 146 |
| | VH-CDR3 | ATSEAAAADYFDY | 147 |
| | VL-CDR1 | CTGSSSNIGAGYDVH | 148 |
| | VL-CDR2 | DNNKRPS | 149 |
| | VL-CDR3 | CAAWDDSLNGPV | 150 |
| | VH | EVQLLESGGGLVQPGGSLRLS-CAASGFTFSDYYMSWIRQAPGKGLEWVSSISSSSSYIS-YADSMKGRFTISRDNSKNTLYLQMNSLRAEDTAVYY-CATSEAAAADYFDYWGQGTLVTVSS | 151 |
| | VL | QSVLTQPPSASGTPGQRVTISCTGSSSNI-GAGYDVHWYQQLPGTAPKLLIYDNNKRPSGVPDRFSG-SKSGTSASLAISGLR-SEDEADYYCAAWDDSLNGPVFGGGTKLTVLG | 152 |

TABLE 2-continued

OX40 antibodies

| Antibody | | | SEQ. ID. NO: |
|---|---|---|---|
| 1-G06 | VH-CDR1 | SSYAMSWVRQAPG | 171 |
| | VH-CDR2 | AHTNEDGSDKKYVDSVKGR | 172 |
| | VH-CDR3 | ARDGSGYSSGWYFDY | 173 |
| | VL-CDR1 | CTGTTSNLGAGYDVH | 174 |
| | VL-CDR2 | SNNQRPSGVPDRFS | 175 |
| | VL-CDR3 | CQSYDSSLSALV | 176 |
| | VH | EVQLLESGGGLVQPGGSLRLSCAASGFTFSSYAMSWVR-QAPGKGLEWVAHTNEDGSDKKYVDSVKGRFTISRD-NSKNTLYLQMNSLRAEDTAVYYCARDGSGY-SSGWYFDYWGQGTLVTVSS | 177 |
| | VL | QSVLTQPPSASGTPGQRVTISCTGTTSNL-GAGYDVHWYQQLPGTAPKLLIYSNNQRPSGVPDRFSG-SKSGTSASLAISGLRSEDEADYYCQSYDSSLSAL-VFGGGTKLTVLG | 178 |

In some embodiments, the immunostimulatory antibody is an anti-PD1 antibody, preferably a human anti-PD1 antibody. The anti-PD1 antibody may be selected from the group consisting of nivolumab and pembrolizumab.

In some embodiments, the immunostimulatory antibody is an anti-PD1 antibody, preferably a human anti-PD1 antibody. The anti-PD1 antibody may be selected from the group consisting of nivolumab and pembrolizumab.

In some embodiments, the immunostimulatory antibody is an anti-PDL1 antibody, preferably a human anti-PDL1 antibody. The anti-PDL1 antibody may be atezolizumab.

In some embodiments, the immunostimulatory antibody is an anti-CTLA-4 antibody, preferably a human anti-CTLA-4 antibody. The anti-CTLA-4 antibody may be selected from the group consisting of ipilimumab and tremilimumab.

The Treg depleting antibody is administered to the subject, such as a human, prior to administration of the immunostimulatory antibody. This means that the Treg depleting antibody is administered to the tumour first in order to achieve the Treg depleting effect. Once the Treg depleting effect is manifested, the immunostimulatory antibody is administered. This sequential administration may be achieved by temporal separation of the two antibodies. Alternatively, or in combination with the first option, the sequential administration may also be achieved by spatial separation of the two antibodies, by administration of the Treg depleting antibody in a way, such as intratumoural, so that it reaches the tumour prior to the immunostimulatory antibody, which is then administerd in a way, such as systemically, so that it reaches the tumour after the Treg depleting antibody.

It would be known to the person skilled in medicine, that medicines can be modified with different additives, for example to change the rate in which the medicine is absorbed by the body; and can be modified in different forms, for example to allow for a particular administration route to the body.

Accordingly, we include that the composition, and/or antibody, and/or agent, and/or medicament of the invention may be combined with an excipient and/or a pharmaceutically acceptable carrier and/or a pharmaceutically acceptable diluent and/or an adjuvant.

We also include that the composition, and/or antibody, and/or agent, and/or medicament of the invention may be suitable for parenteral administration including aqueous and/or non-aqueous sterile injection solutions which may contain anti-oxidants, and/or buffers, and/or bacteriostats, and/or solutes which render the formulation isotonic with the blood of the intended recipient; and/or aqueous and/or non-aqueous sterile suspensions which may include suspending agents and/or thickening agents. The composition, and/or antibody, and/or agent, and/or medicament of the invention may be presented in unit-dose or multi-dose containers, for example sealed ampoules and vials, and may be stored in a freeze-dried (i.e. lyophilised) condition requiring only the addition of the sterile liquid carrier, for example water for injections, immediately prior to use.

Extemporaneous injection solutions and suspensions may be prepared from sterile powders, and/or granules, and/or tablets of the kind previously described.

For parenteral administration to human patients, the daily dosage level of the Treg depleting antibody and/or the immunostimulatory antibody will usually be from 1 mg/kg bodyweight of the patient to 20 mg/kg, or in some cases even up to 100 mg/kg administered in single or divided doses. Lower doses may be used in special circumstances, for example in combination with prolonged administration. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Typically, the composition and/or medicament of the invention will contain the Treg depleting antibody and/or the immunostimulatory antibody at a concentration of between approximately 2 mg/ml and 150 mg/ml or between approximately 2 mg/ml and 200 mg/ml. In a preferred embodiment, the medicaments and/or compositions of the invention will contain the Treg depleting antibody and/or the immunostimulatory antibody at a concentration of 10 mg/ml.

Generally, in humans, oral or parenteral administration of the composition, and/or antibody, and/or agent, and/or medicament of the invention is the preferred route, being the most convenient. For veterinary use, the composition, and/or antibody, and/or agent and/or medicament of the invention are administered as a suitably acceptable formulation in accordance with normal veterinary practice and the veterinary surgeon will determine the dosing regimen and route of administration which will be most appropriate for a particular animal. Thus, the present invention provides a pharmaceutical formulation comprising an amount of an antibody and/or agent of the invention effective to treat various conditions (as described above and further below). Preferably, the composition, and/or antibody, and/or agent, and/or medicament is adapted for delivery by a route selected from the group comprising: intravenous; intramuscular; subcutaneous.

The present invention also includes composition, and/or antibody, and/or agent, and/or medicament comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others. Pharmaceutically acceptable base addition salts may also be used to produce pharmaceutically acceptable salt forms of the agents according to the present invention. The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

The combination of a Treg depleting antibody molecule and immunostimulatory antibody molecule, wherein the Treg depleting antibody molecule is administered to a subject prior to administration of the immunostimulatory antibody molecule to the subject can be used use in the treatment of cancer.

We include that the subject could be mammalian or non-mammalian. Preferably, the mammalian subject is a human or is a non-mammalian, such as a horse, or a cow, or a sheep, or a pig, or a camel, or a dog, or a cat. Most preferably, the mammalian subject is a human.

By "exhibit", we include that the subject displays a cancer symptom and/or a cancer diagnostic marker, and/or the cancer symptom and/or a cancer diagnostic marker can be measured, and/or assessed, and/or quantified.

It would be readily apparent to the person skilled in medicine what the cancer symptoms and cancer diagnostic markers would be and how to measure and/or assess and/or quantify whether there is a reduction or increase in the severity of the cancer symptoms, or a reduction or increase in the cancer diagnostic markers; as well as how those cancer symptoms and/or cancer diagnostic markers could be used to form a prognosis for the cancer.

Cancer treatments are often administered as a course of treatment, which is to say that the therapeutic agent is administered over a period of time. The length of time of the course of treatment will depend on a number of factors, which could include the type of therapeutic agent being administered, the type of cancer being treated, the severity of the cancer being treated, and the age and health of the subject, amongst others reasons.

By "during the treatment", we include that the subject is currently receiving a course of treatment, and/or receiving a therapeutic agent, and/or receiving a course of a therapeutic agent.

In some embodiments the cancer to be treated in accordance with the present invention is a solid tumour.

In some embodiments, the cancer is selected from the group consisting of sarcomas, carcinomas and lymphomas.

In some embodiments, the cancer is selected from the group consisting of squamous cell carcinoma (SCC), thymoma, neuroblastoma or ovarian cancer.

Each one of the above described cancers is well-known, and the symptoms and cancer diagnostic markers are well described, as are the therapeutic agents used to treat those cancers. Accordingly, the symptoms, cancer diagnostic markers, and therapeutic agents used to treat the above mentioned cancer types would be known to those skilled in medicine.

Clinical definitions of the diagnosis, prognosis and progression of a large number of cancers rely on certain classifications known as staging. Those staging systems act to collate a number of different cancer diagnostic markers and cancer symptoms to provide a summary of the diagnosis, and/or prognosis, and/or progression of the cancer. It would be known to the person skilled in oncology how to assess the diagnosis, and/or prognosis, and/or progression of the cancer using a staging system, and which cancer diagnostic markers and cancer symptoms should be used to do so.

By "cancer staging", we include the Rai staging, which includes stage 0, stage I, stage II, stage III and stage IV, and/or the Binet staging, which includes stage A, stage B and stage C, and/or the Ann Arbour staging, which includes stage I, stage II, stage III and stage IV.

It is known that cancer can cause abnormalities in the morphology of cells. These abnormalities often reproducibly occur in certain cancers, which means that examining these changes in morphology (otherwise known as histological examination) can be used in the diagnosis or prognosis of cancer. Techniques for visualizing samples to examine the morphology of cells, and preparing samples for visualization, are well known in the art; for example, light microscopy or confocal microscopy.

By "histological examination", we include the presence of small, mature lymphocyte, and/or the presence of small, mature lymphocytes with a narrow border of cytoplasm, the presence of small, mature lymphocytes with a dense nucleus lacking discernible nucleoli, and/or the presence of small, mature lymphocytes with a narrow border of cytoplasm, and with a dense nucleus lacking discernible nucleoli, and/or the presence of atypical cells, and/or cleaved cells, and/or prolymphocytes.

It is well known that cancer is a result of mutations in the DNA of the cell, which can lead to the cell avoiding cell death or uncontrollably proliferating. Therefore, examining these mutations (also known as cytogenetic examination) can be a useful tool for assessing the diagnosis and/or prognosis of a cancer. An example of this is the deletion of the chromosomal location 13q14.1 which is characteristic of chronic lymphocytic leukaemia. Techniques for examining mutations in cells are well known in the art; for example, fluorescence in situ hybridization (FISH).

By "cytogenetic examination", we include the examination of the DNA in a cell, and, in particular the chromosomes. Cytogenetic examination can be used to identify changes in DNA which may be associated with the presence of a refractory cancer and/or relapsed cancer. Such may include: deletions in the long arm of chromosome 13, and/or the deletion of chromosomal location 13q14.1, and/or trisomy of chromosome 12, and/or deletions in the long arm of chromosome 12, and/or deletions in the long arm of chromosome 11, and/or the deletion of 11q, and/or deletions in the long arm of chromosome 6, and/or the deletion of 6q, and/or deletions in the short arm of chromosome 17, and/or the deletion of 17p, and/or the t(11:14) translocation, and/or the (q13:q32) translocation, and/or antigen gene receptor rearrangements, and/or BCL2 rearrangements, and/or BCL6 rearrangements, and/or t(14:18) translocations, and/or t(11:14) translocations, and/or (q13:q32) translocations, and/or (3:v) translocations, and/or (8:14) translocations, and/or (8:v) translocations, and/or t(11:14) and (q13:q32) translocations.

It is known that subjects with cancer exhibit certain physical symptoms, which are often as a result of the burden of the cancer on the body. Those symptoms often reoccur in the same cancer, and so can be characteristic of the diagnosis, and/or prognosis, and/or progression of the disease. A person skilled in medicine would understand which physical symptoms are associated with which cancers, and how assessing those physical systems can correlate to the diagnosis, and/or prognosis, and/or progression of the disease. By "physical symptoms", we include hepatomegaly, and/or splenomegaly.

BRIEF DESCRIPTION OF THE DRAWINGS

In the examples below, reference is made to the following figures:

FIG. 1A: Groups of BALB/c mice were challenged with $5 \times 10^5$ CT26 s.c. on day 0. When tumours were palpable mice received anti-4-1BB (LOB12.0) mIgG1, mIgG2a or PBS control i.v. followed by 3 further administrations i.p. every other day (200 μg final dose). FIG. 1B: Groups of A/J mice were challenged with $2 \times 10^6$ NXS2 cells s.c. and received 200 μg anti-4-1 BB mAb or isotype control mAb i.p. when tumour was palpable. A second dose of 200 μg was given 3 days later. In both experimental models tumour growth was monitored and mice culled when mean tumour area exceeded 225 mm². Data are expressed as tumour area (mm²) on the days after tumour challenge as indicated; each line represents an individual mouse. Panels on the right show percentage survival to the humane end-point. Data represent examples of at least 2 independent experiments where n=5 mice per group.

FIG. 2A: Splenocytes from Foxp3-GFP mice either sorted to remove GFP+ cells ($-T_{reg}$) or not ($+T_{reg}$) were incubated with 0.1 μg/ml anti-CD3 and the indicated concentrations of either anti-4-1 BB (LOB12.0) mIgG1 or mIgG2a as indicated. Incorporation of [$^3$H]-thymidine was measured during the last 16 hours of a 72 hour culture. FIG. 2B Splenocytes from C57BL/6 mice were similarly incubated with 0.1 μg/ml anti-CD3 and the indicated concentrations of anti-4-1BB mIgG1, mIgG2a or a 1:1 mix of the two prior to assessment of [$^3$H]-thymidine incorporation. Data in FIG. 2A and FIG. 2B show mean (+/−SEM) counts per minute of triplicate wells. FIG. 2C: Groups of mice received 5 mg OVA and 200 μg anti-4-1 BB mIgG1 or mIgG2a i.p. on day 0. SIINFEKL-specific T-cell responses in peripheral blood were quantified by flow cytometry and expressed as a % of total CD8+ cells. Data are from three separate experiments, and show time course of response (mean±SEM, 6 mice per group) and peak of response (mean and individual responses, 9 mice per group, *p=0.023). FIG. 2D: Groups of A/J mice were challenged with $2 \times 10^6$ NXS2 cells s.c. on day 0 and received 200 μg anti-4-1BB mAb or isotype control mAb i.p. and control (SIINFEKL; left panel) or TH (FET-FEAKI; right panel) peptide on day 3. A second dose of mAb (200 μg) was given on day 6. Data in FIG. 2B and FIG. 2C represent examples of at least 2 experiments where n=5 mice per group.

FIG. 3A: Immunofluorescence microscopy image showing 4-1BB expressing intratumoural Foxp3+ Treg in CT26 tumour (left panel). Scale bar=50 μM. Flow cytometry histograms demonstrating 4-1BB expression on T cell subsets from TILs and splenocytes (right panels). 4-1BB expression (black line) on CD4+ Foxp3+ (inset top panels), CD4+ Foxp3− (inset middle panels) and CD8+ T cells (inset bottom panels), against isotype control (grey line). Cells were isolated from mice bearing CT26 tumour. FIG. 3B: Samples of freshly excised ovarian tumours, ascites and blood were obtained from patients at surgery and compared to healthy PBMC. Tumour samples were minced and digested before separation with a density gradient. Matched peripheral blood was obtained and peripheral blood mononuclear cells were separated by centrifugation. 4-1BB expression was assessed on CD4+ CD25+CD127− Treg cells, CD4+ non-Treg cells and CD8+ effector T cells by flow cytometry. Top panels show representative histograms with 4-1BB expression in tumour tissue (solid black), blood (dashed grey) and ascites (dashed black) from the same patient. Isotype control depicted in solid grey. Lower panel shows 4-1BB expression on T cell subsets from different tissue samples. Data points represent individual patients/donors with n=1 for healthy PBMCs, n=20 for ascites, n=9 for tumour and n=5 for patient blood. FIG. 3C: Samples of freshly excised cutaneous squamous cell carcinoma (SCC) and normal skin were obtained from patients at surgery. Samples were minced and digested before separation with a density gradient. Matched peripheral blood was obtained and peripheral blood mononuclear cells were separated by centrifugation. Cells were stained for 4-1BB and staining detected by flow cytometry. Top panels show representative histograms with 4-1BB staining shown as open histograms; tumour tissue (solid black), blood (dashed grey), normal skin (dashed black) and isotype control (solid grey). Lower panel shows 4-1BB expression on T cell subsets from different tissue samples. Data points represent 10 individual patients.

FIG. 4A: Groups of 3-4 WT, FcγRIIB KO or γ chain KO BALB/c mice received were challenged with 5×104 CT26 cells s.c. on day 0. When tumours were palpable mice received anti-4-1 BB mIgG1, mIgG2a or PBS control i.v. followed by 3 further administrations i.p. every other day (200 µg final dose). Mice were sacrificed on day 13 and spleen and tumour analysed by flow cytometry. Data show the frequency of Foxp3+ cells within the CD4+ population in the tumour (left panel) or in matched spleens (right panel). Data are representative of two independent experiments. FIG. 4B: Mice were treated as in (A) and CD8+, Ki67+ T cells enumerated and plotted as fold change compared to control. FIG. 4C: Groups of WT, γ chain KO, or FcγR null mice (γ chain KO×FcγRIIB KO), γ chain KO or FcγRIIB KO BALB/c mice were challenged with 5×104 CT26 cells and treated with anti-4-1 BB mAb as in (A). Tumour growth was monitored and mice culled when mean tumour area exceeded 225 mm2. Data are expressed as tumour area (mm2) on the days after tumour challenge as indicated, each line represents an individual mouse. Panels on the right show percentage survival to the humane endpoint. Data represent examples of at least 2 experiments where n=5 mice per group. FIG. 4D: CFSE labelled target murine splenic T cells opsonised with anti-4-1 BB mIgG1, mIgG2a or control mAb were co-cultured with wild type (solid bars) or FcgRIIB KO (open bars) mBMDM and then assessed for phagocytosis. (E) (left panel) CFSE labelled target human T cells opsonised with anti-human 4-1 BB hIgG1 mAb clones SAP3-6, BI15-B02 (also denoted 005-B102) or control were co-cultured with hMDM and then assessed for ADCP. (right hand panel) Level of phagocytosis plotted in relation to 4-1BB expression level as determined by flow cytometry. In all cases phagocytosis is plotted as % of double positive macrophages.

FIG. 5A: Groups of age and sex matched BALB/c mice were challenged with 5×104 CT26 s.c. on day 0. When tumours were palpable mice received anti-4-1BB (LOB12.0) mIgG1, mIgG2a, concurrent mIgG1 and mIgG2a or PBS control i.v. followed by 3 further administrations i.p. every other day (200 µg final dose). For scheduled administration mIgG2a was given i.v. and then mIgG1 given i.p. 4 days later. Tumour growth was monitored and mice culled when mean tumour area exceeded 225 mm$^2$. Data are expressed as the average tumour area (mm2) on the days after tumour challenge as indicated. Data presented is combined from two independent experiments where n=10 mice per group. FIG. 5B: Mice were challenged with CT26 tumour and then given monotherapy as in FIG. 5A or scheduled combinations of anti-4-1 BB mIgG1 or mIgG2a and/or anti-PD-1 rIgG1 (WT) or its deglycosylated form. For combinations anti-4-1 BB mAb were administered i.v. when tumours were first palpable and then anti-PD-1 given i.p. 4 days later. Tumour growth was monitored and data plotted as in FIG. 5A. Data represent examples of at least 2 independent experiments where n=4 or 5 mice per group.

FIG. 6A: nrCE-SDS profiles of anti-4-1 BB (LOB12.0) mIgG2a, mIgG2a/h2 and "skewed" mIgG2a/h2B. FIG. 6B: Splenocytes from C57Bl//6 mice were incubated with 0.01 µg/ml anti-CD3 and the indicated concentrations of either anti-4-1 BB mIgG1, mIgG2a or mIgG2a/h2B as indicated. Incorporation of [3H]-thymidine was measured during the last 16 hours of a 72 hour culture. FIG. 6C: CFSE labelled target murine splenic T cells opsonised with anti-4-1BB mIgG2a, mIgG2a/h2B or control mAb were co-cultured with wild type mBMDM and then assessed for phagocytosis. Phagocytosis is plotted as % of double positive macrophages. FIG. 6D: Groups of age and sex matched C57Bl/6 mice were challenged with 5×105 EG7 s.c. on day 0. On days 3, 5 and 7 mice received 200 µg mAb or PBS control i.p. as indicated. On day 20 tumours were harvested and TIL enumerated by flow cytometry. n=4 mice per group. (E) Mice were set up as in (D) and tumour growth was monitored and mice culled when mean tumour area exceeded 400 mm2. Data represent examples of at least 2 independent experiments where n=5 mice per group.

FIG. 7A: Surface plasmon resonance analysis of anti-4-1 BB (clone LOB12.0) mIgG1, mIgG2a and the parental rIgG2a binding to mouse FcγRI, IIB, III and IV. Recombinant, soluble FcγR protein (0, 6, 23, 94, 375, 1500 nM) was passed over 4-1-BB mAb immobilized at 5000 RU. Sensorgrams are shown. FIG. 7B: A human cell line stably transfected with a construct encoding the extracellular and transmembrane region of murine 4-1BB was incubated with anti-4-1 BB of mIgG1, mIgG2a isotype or with the parental rIgG2a mAb at a range of concentrations prior to staining with a PE-labelled secondary antibody. Data show mean fluorescence intensity at each concentration as a percentage of maximum. FIG. 7C: Rat anti-4-1 BB was mixed with mouse mIgG1 or mIgG2a anti-4-1BB mAb at the concentrations indicated, prior to incubation with a murine 4-1BB transfected cell line. Rat mAb binding was detected with an anti-rat secondary antibody and data are expressed as mean fluorescence intensity of the rat anti-4-1 BB antibody relative to the concentration of competitive mouse anti-4-1 BB.

FIG. 9A: Groups of 3 wild type or FcγRIIB−/− mice received 2×10$^5$ OT-I cells i.v., followed 24 hours later (day 0) by i.p. injection of 0.5 mg OVA and 200 µg mIgG1 or mIgG2a anti-4-1BB. Control mice received OVA alone. Blood samples were taken to measure circulating SIINFEKL tetramer+ CD8+ cells over the course of the response, expressed as a % (mean±SEM) of total CD8+ cells. Data are representative of 2 experiments. FIG. 9B: Groups of 5 C57BL/6 mice were injected with 2.5×10$^5$ B16/BL6 cells i.d. on day 0 prior to receiving 1×10$^6$ irradiated FVAX cells i.d. on the opposite flank on days 3, 6 and 9. Concurrent with FVAX injection mice received either PBS, 100 µg anti-CTLA-4 (clone 9D9) or anti-CTLA-4 and 300 µg anti-4-1 BB antibodies as indicated i.p. Percentage survival to the humane end point is shown.

FIG. 10A: Surface plasmon resonance analysis of anti-PD-1 (clone EW1-9) rIgG1 (solid black) and rIgG1 deglycosylated (solid grey) binding to mouse FcγRI, IIB, III and IV. PD-1 mAb (500 nM) was passed over recombinant FcγR-his protein (1000 RU) (R&D Systems) captured onto a CM5 chip with an anti-histidine mAb (GE Healthcare). Sensorgrams are shown with 0 nM curve subtracted. FIG. 10B: Analysis demonstrating that anti-PD-1 mAb bind to PD-1 and block PD-L1 binding. Anti-PD-1 rIgG1 (solid black), rIgG1 deglycosylated (solid grey) or buffer (dashed black) was passed over recombinant PD-1-his (R&D Systems) (2000 RU) captured onto a CM5 chip with an anti-histidine mAb. At the timepoint indicated by the arrow recombinant PD-L1-Fc (R&D Systems) was passed over to demonstrate binding to PD-1 and blockade by anti-PD-1.

FIG. 13 shows ligand blocking.

FIG. 21 shows a table summarizing the characteristics of some of the antibodies described herein.

EXAMPLES

Specific, non-limiting examples which embody certain aspects of the invention will now be described.

Examples Relating to Sequential Administration

Results
Therapeutic Activity of Anti-4-1BB mAb is Determined by Isotype

Figure 1:
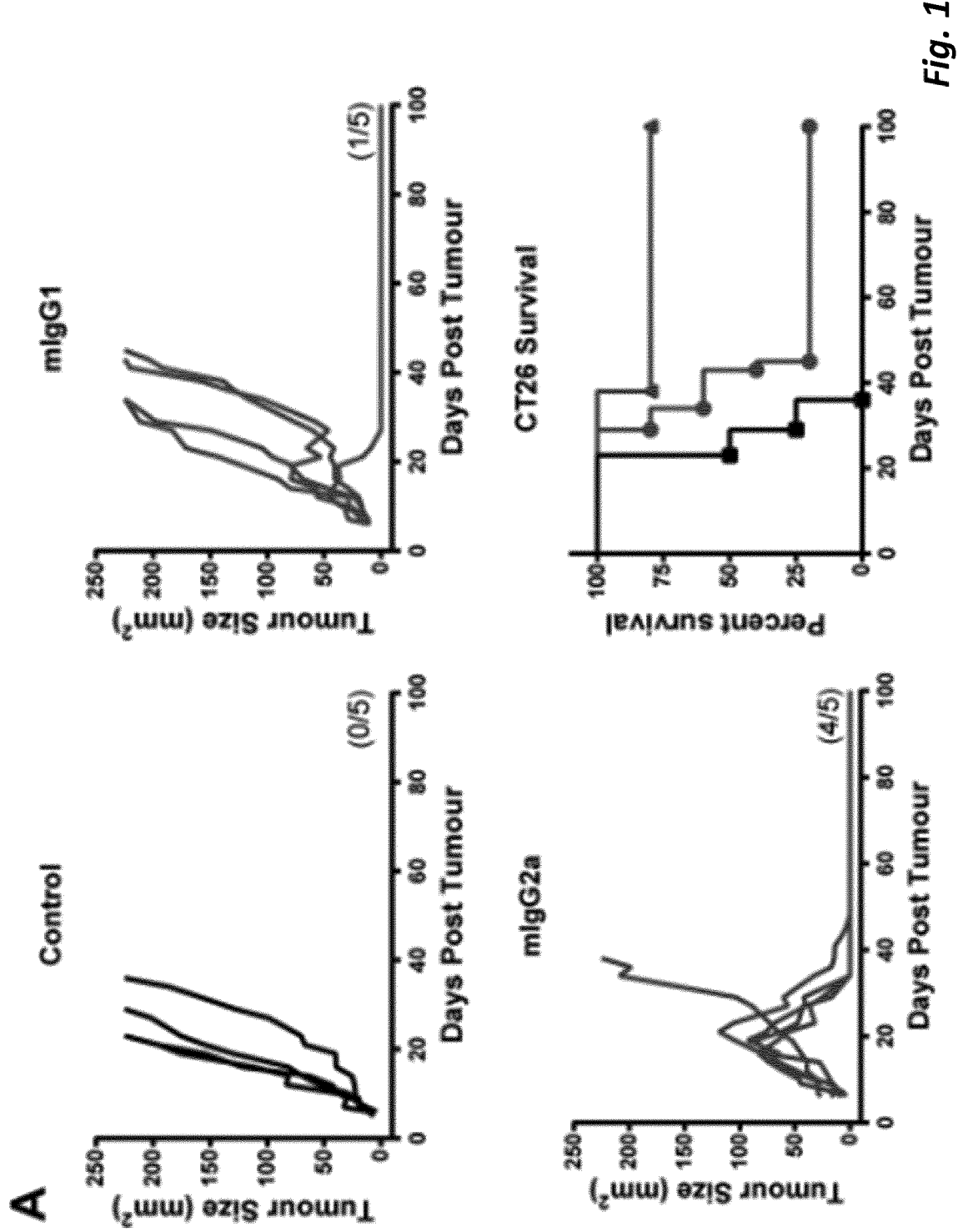
FIG. 1. Anti-4-1BB mIgG2a mAb, but not mIgG1, confer survival benefit in multiple cancer models.
Figure 7:
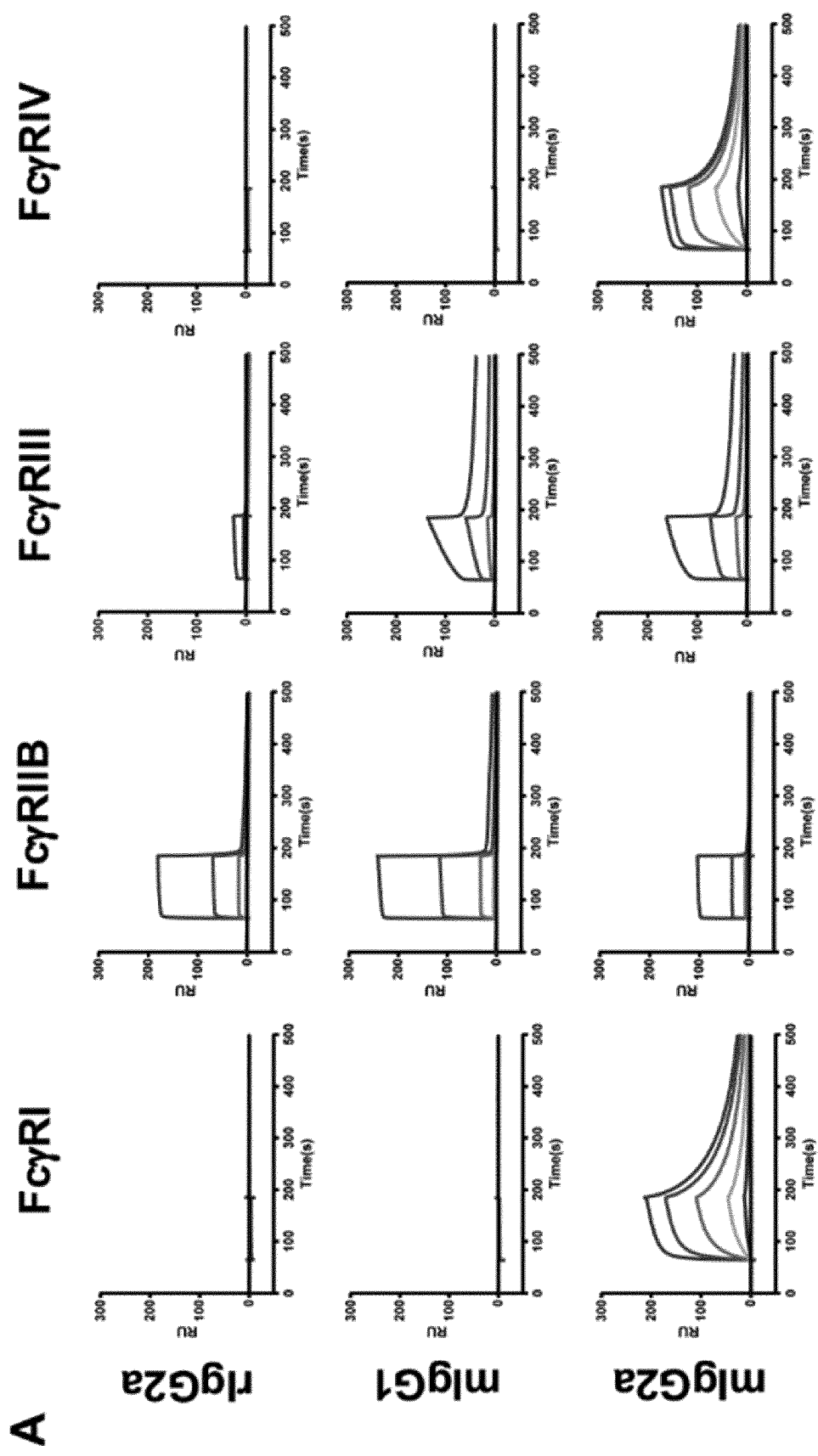
FIG. 7. Anti-4-1BB mAb characterisation.
Figure 8:
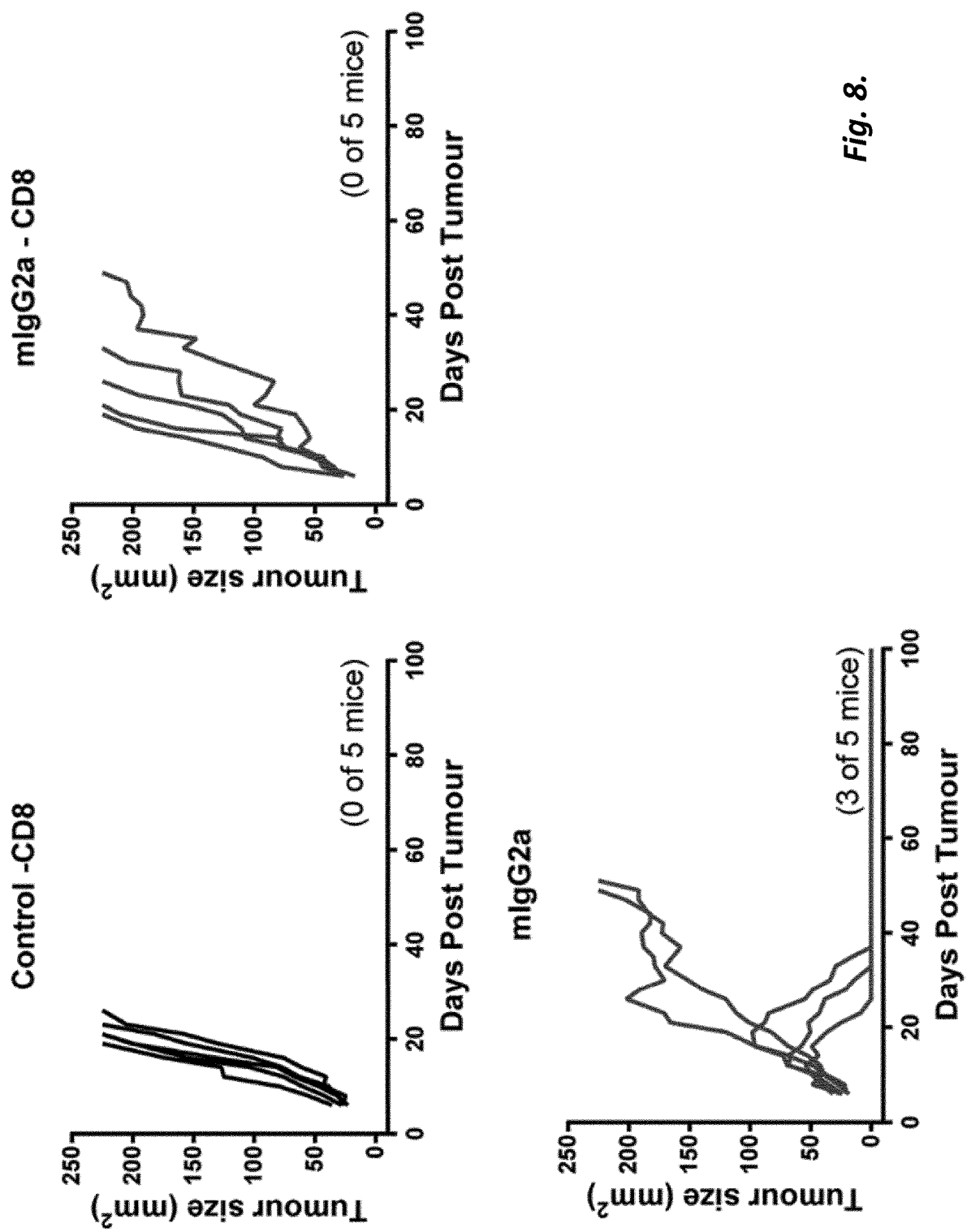
FIG. 8. Anti-tumour efficacy of anti-4-1BB mIgG2a mAb is dependent upon CD8+ T cells. Groups of BALB/c mice were treated, or not, with 500 µg of a CD8-depleting antibody on days −1, 1 and 4 relative to challenge with 5×10$^4$ CT26 cells s.c. on day 0. Anti-41BB mIgG2a mAb was administered on day 6 i.v., and on days 8, 10 and 12 i.p, to a final total dose of 200 µg. Tumour sizes were recorded and mice culled when mean tumour diameter reached 15 mm. Data show tumour area (mm$^2$) on the days indicated after tumour challenge with each line representing an individual mouse. (n=5/group)

We and others have previously established the dependence of immunostimulatory mAb activity targeting TNFR superfamily members on cross-linking provided by the inhibitory FcγRIIB. To establish if this requirement similarly applied to anti-4-1 BB we generated mIgG1 and mIgG2a chimeric versions of the rIgG2a anti-4-1 BB mAb (LOB12.0 generated in-house (16)) as previously described for other mAb specificities (17-19). The nucleotide sequences encoding LOB12.0 mIgG1 heavy chain is shown in SEQ. ID. NO: 179, and the corresponding amino acid sequence is shown in SEQ ID NO: 180. The nucleotide sequences encoding LOB12.0 mIgG2a heavy chain is shown in SEQ. ID. NO: 181, and the corresponding amino acid sequence is shown in SEQ ID NO: 182. Analysis by surface plasmon resonance and flow cytometry established that these mAb possessed an expected mFcγR binding profile, with mIgG2a having a high activatory to inhibitory FcγR ratio (A:I) and conversely mIgG1 a low A:I (FIG. 7A, (19, 20)); both mAb retained equivalent 4-1 BB specificity and binding (FIGS. 7B and 7C). We then assessed the therapeutic potential of these mouse anti-4-1 BB mAb in three different established solid tumour models using the CT26 colon carcinoma (FIG. 1A) and NXS2 neuroblastoma (FIG. 1B). In marked contrast to our studies with anti-CD40 (18, 19, 21) and published reports with other agonistic anti-TNFR superfamily mAb targeting DR5 (22, 23), for anti-4-1 BB, high A:I ratio mIgG2a mAb gave considerable therapeutic benefit (80% long term survival in all models) while the low A:I ratio mIgG1 version was largely ineffective (0-20% survival). Notably, although it was the mIgG2a mAb which was protective in these settings its therapeutic effect was still dependent upon CD8+ T cells (FIG. 8) and led to long term productive anti-tumour immunity, as determined by tumour rechallenge experiments. These results suggest that the protective effect of mIgG2a anti-4-1BB is mediated through an adaptive anti-tumoural immune response, but that this mAb utilises molecular mechanisms occurring in an FcγRIIB-independent manner, in contrast to anti-CD40 mAb.

Immunostimulatory Activity of Anti-4-1 BB is Optimal with Mouse IgG1 Isotype

Figure 2:
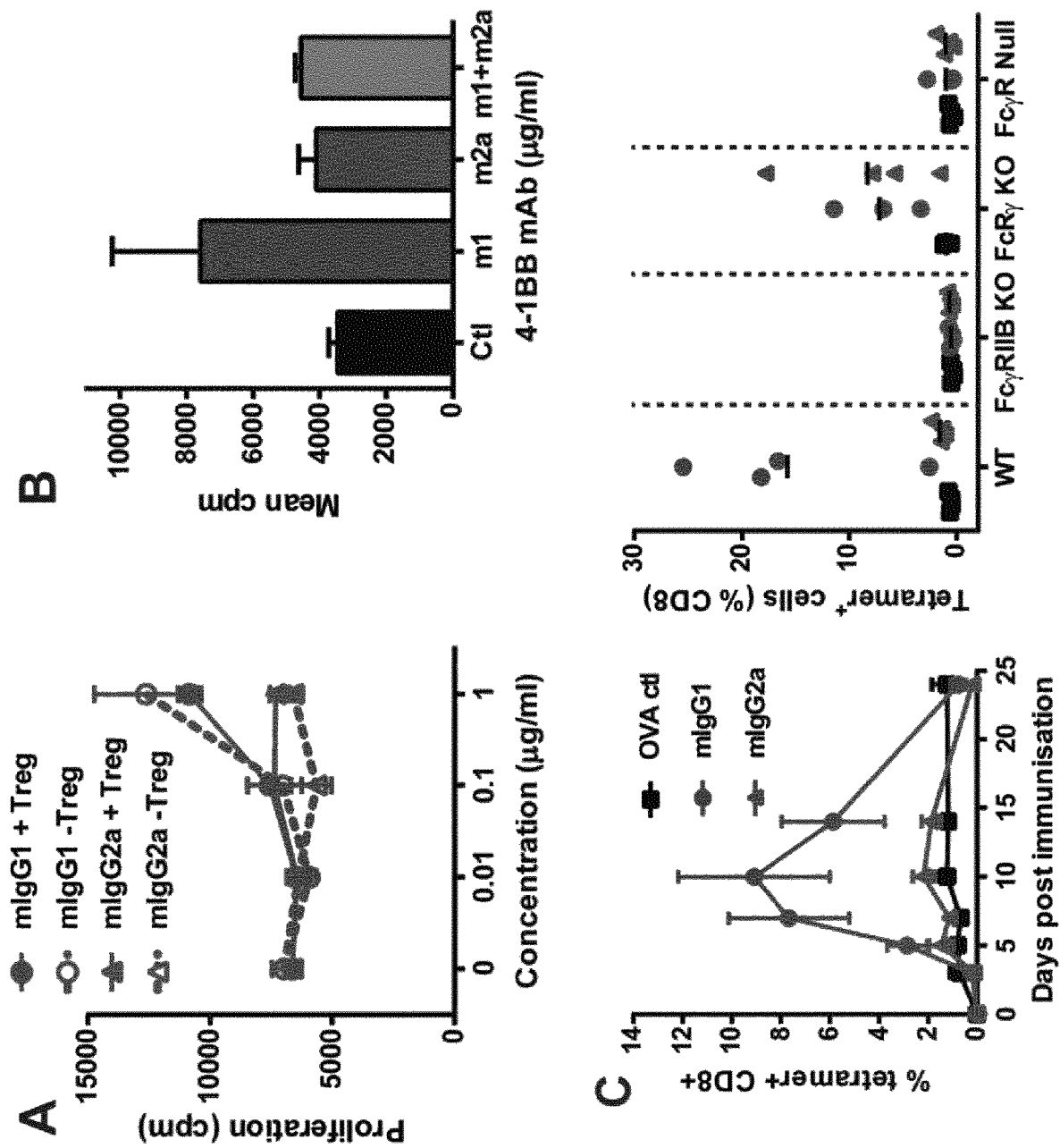
FIG. 2. Anti-4-1BB mIgG1 exerts agonist activity in vitro and in vivo.
Figure 9:
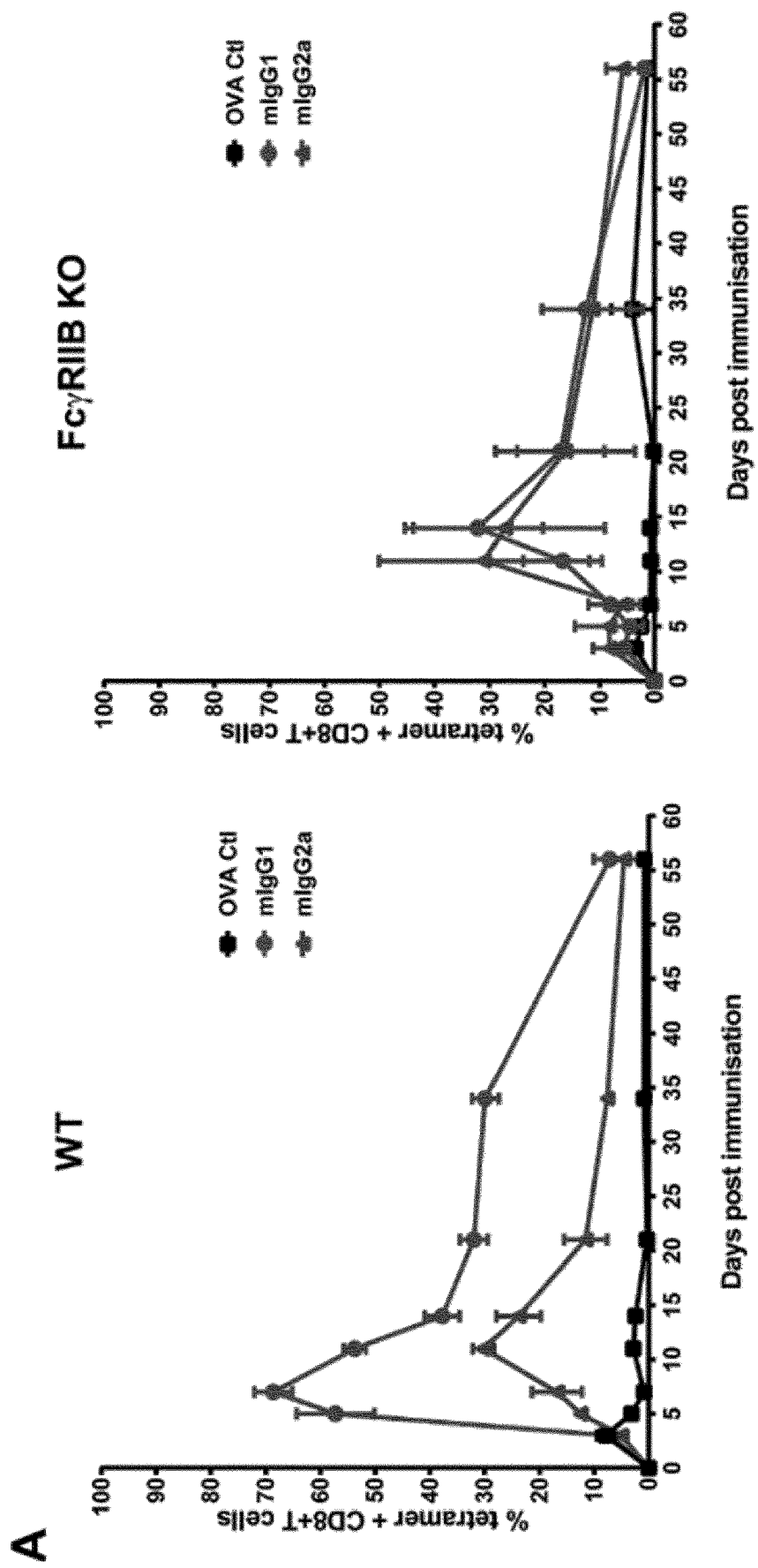
FIG. 9. Primary in vivo expansion of OT-I cells in response to OVA and anti-4-1BB mAb.

Given the results obtained in our tumour models and previous studies demonstrating a critical role for CD8+ T cells in mediating the effects of anti-4-1 BB mAb, we sought to establish the isotype-dependence of anti-4-1 BB mAb activity on T cell populations in vitro and in vivo. Using an in vitro T cell co-stimulation assay (FIG. 2A) only mIgG1, but not mIgG2a, (same antibodies as used above) demonstrated agonistic activity. This is in keeping with other published results (18, 19). The costimulatory activity of mIgG1 was independent of Treg cells in the T cell culture assay, suggesting that this anti-4-1BB mAb mediates its effects through targeting 4-1BB on effector T cells. Finally, the costimulatory activity of mIgG1 was abolished by the addition of mIgG2a, demonstrating that both mAb variants bind with similar avidity and compete for binding to 4-1BB on effector T cells (FIG. 2B). These in vitro results were confirmed using an in vivo immunisation model with the model antigen OVA in both an endogenous (FIG. 2C) and an OT1 T cell transfer setting (FIG. 8A).ln this context the superior agonistic activity of mIgG1 was dependent upon the inhibitory FcγRIIB (FIG. 2C, FIG. 9A) as previously shown for anti-CD40 mAb (18, 19, 24, 25). Finally, in two immunisation models (NXS2 peptide and B16-sFlt3L-Ig; FIG. 2D and FIG. 9B, respectively) the mIgG1 and mIgG2a isotype antibodies were equally therapeutic (FIG. 2D and FIG. 9B). Of note, the efficacy of mIgG1, but not IgG2a, was abolished in the absence of vaccination, confirming that mIgG1, but not mIgG2a, is operating through a mechanism dependent on immune activation, and likely FcγRIIB cross-linking (FIG. 2D).

4-1BB is Expressed on Intra-Tumoural Treg Cells in Mouse Tumour Models and Human Cancer Patients Having established that anti-4-1 BB mIgG2a is more active than mIgG1 in treating mice with established tumours, but in these mice mIgG2a lacks the ability to deliver co-stimulatory activity, we looked for alternative mechanisms that could explain its immunomodulatory effects. 4-1BB mRNA and protein are preferentially expressed in Treg cells compared to resting effector T cells (14, 26, 27), its expression is further upregulated following activation of Treg cells (27, 28) and very recently has been shown to be upregulated, at least at the transcriptional level, in intratumoral Treg in human solid cancers (29, 30). We therefore examined the possibility that anti-4-1 BB mIgG2a, which possesses a high A:I FcγR binding profile could potentiate an anti-tumour response via deletion of Treg cells. We began by confirming the presence of 4-1BB on Treg cells in two murine tumour models CT26 (FIG. 3A) and NXS2 and found that 4-1 BB was expressed on a substantial proportion of tumour-infiltrating Tregs and only a small minority of effector T cells. Furthermore, only a small fraction of splenic Treg cells expressed 4-1BB. In order to confirm that these observations were potentially translatable to humans at the protein level, we determined by flow cytometry whether 4-1BB was present on intratumoural Tregs in patients with ovarian cancer and squamous cell carcinoma. It can be seen in FIG. 3B and FIG. 3C that 4-1 BB was found on CD4+Foxp3+ Treg cells but not on effector CD4+ or CD8+ T cells in tumours and that 4-1BB was expressed at lower levels on Tregs isolated from healthy PBMC, matched blood, ascites or normal skin.

The Role of FcγR in Mediating the Anti-Tumour Activity of Anti-4-1BB mAb

Figure 4:
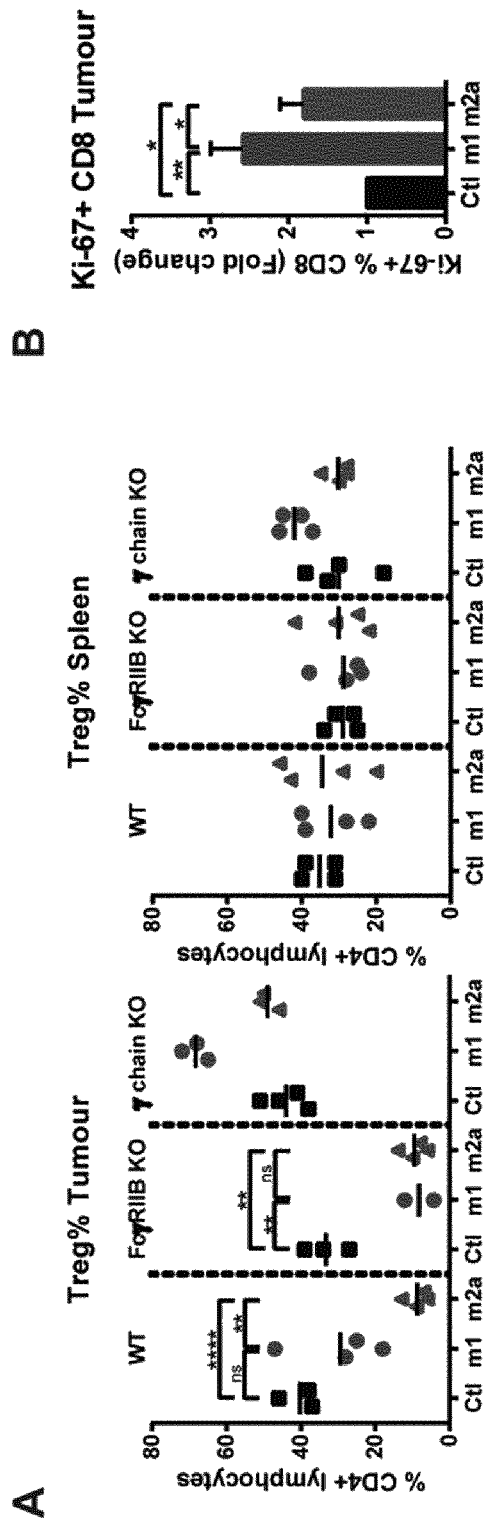
FIG. 4. The primary mechanism of anti-4-1 BB mAb therapy in solid tumours is dependent on antibody isotype and FcγR availability.

Having established that intratumoural Treg express 4-1BB we used the CT26 tumour model to determine the potential role for and relative depleting capacity of anti-4-1 BB mAb. Our data demonstrate that in wild-type mice the mIgG2a mAb efficiently deleted intra-tumoural Tregs, whilst the mIgG1 variant was ineffective (same antibodies as used above (FIG. 4A). This depletion effect was restricted to the tumour and dependent upon expression of the common γ chain, a crucial component of activatory FcγR complexes. Furthermore, in FcγRIIB knockout mice the depleting activity of the mIgG1 mAb was enhanced to similar levels as to that of the mIgG2a, demonstrating that the depletion efficiency of these mAb is intimately linked to their FcγR A:I ratio and that depletion potency can be manipulated through changes in FcγR expression. We next sought to determine if we could observe activation of tumour infiltrating CD8 T cells in these mice and observed that despite the lack of efficacy of the mIgG1 mAb in WT tumour bearing mice administration of anti-4-1BB mIgG1 mAb led to a clear and significant increase in proliferation of CD8 T cells as monitored by Ki-67 positivity (FIG. 4B). While the mIgG2a isotype also induced an increase in CD8 activation this was significantly less than the mIgG1. These data likely demonstrate the dominant role of Treg in the CT26 tumour model and suggest that inducing CD8 responses with mIgG1 in wild-type mice without removing Treg suppression is insufficient to induce a productive anti-tumour response.

As anti-4-1BB mIgG2a was efficient in mediating depletion of intra-tumoural Treg cells in a manner dependent on the expression of activatory FcγR, we reasoned that the absence of activatory FcγR would be detrimental for the therapeutic effects of this mAb. Surprisingly, however, in the CT26 tumour model (FIG. 4C), anti-4-1 BB mIgG2a retained anti-tumour activity in the absence of activatory FcγR, suggesting that Treg cell depletion may not fully account for its therapeutic activity. In contrast to the minimal effects on anti-4-1 BB mIgG2a efficacy, there was a substantial improvement in the ability of anti-4-1 BB mIgG1 to promote anti-tumour immunity in the absence of activatory FcγR (2/5 in CT26). Given the FcγR binding profiles demonstrated for mIgG1 and mIgG2a mAb (FIG. 7), these findings suggest that in the absence of competitive binding of mAb to activatory FcγR, there is productive engagement of FcγRIIB by both mIgG1 and mIgG2a, thus allowing optimal cross-linking of mAb to deliver costimulation. This notion is further supported by the observed T cell activation of mIgG2a in the FcRg KO animals in the OVA model (FIG. 2C). In keeping with the enhanced Treg depleting activity of mIgG1 in FcγRIIB KO mice (FIG. 4A) when therapies were carried out in FcγRIIB KO mice the mIgG1 isotype mAb demonstrated enhanced and equivalent activity to mIgG2a. These results coupled with the observation that in the absence of all FcγR, neither mAb produced any therapeutic activity (FIG. 4C) support the importance of efficient, non-competing FcγR engagement for optimal in vivo activity.

We next sought to formally demonstrate the depleting capacity of anti-4-1 BB mAb using both mouse and human targets and effectors in vitro. Using WT mouse bone marrow derived macrophages and 4-1BB expressing T cell targets we observed that mIgG2a induced effective phagocytosis of target cells and the mIgG1 mAb was ineffective (FIG. 4D). In agreement with our in vivo depletion results (FIG. 4B) and therapeutic responses (FIG. 4C), when FcγRIIB KO macrophages were used as effectors a significant increase in mIgG1 mediated phagocytosis was observed in line with levels obtained with mIgG2a and WT effectors. We then confirmed the translational potential of our findings in a fully human system using human targets and monocyte derived macrophage effectors. In this system we found that two different huIgG1 anti-human 4-1BB clones (SAP3-6 and 005-B02) could mediate effective phagocytic clearance (FIG. 4E). Finally, we sought to confirm that it was the level of 4-1BB expression rather than the cell type per se that dictated the efficacy of depletion. We did this using both human (FIG. 4E) and mouse (data not shown) in vitro generated macrophages and target cells with varying levels of 4-1BB expression and found a direct correlation between 4-1BB expression and the efficiency of target cell depletion. This supports the notion that it is the high level of 4-1 BB expression on Treg in the tumour microenvironment that makes them a good target and that lower expressing CD8 cells are likely spared.

Figure 5:
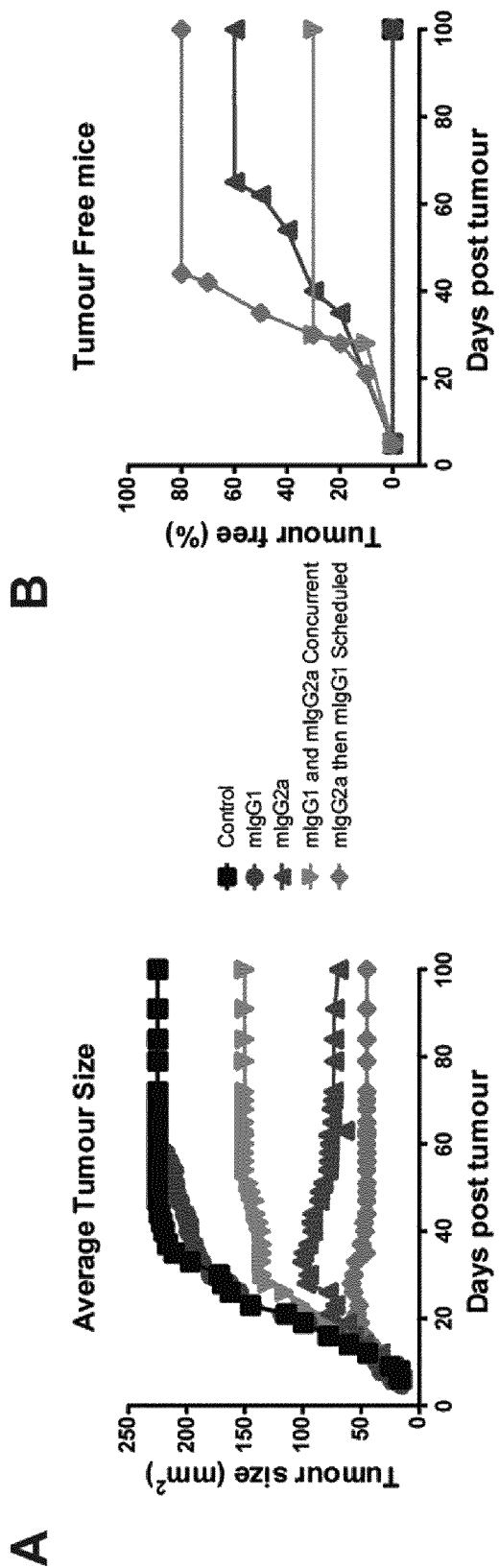
FIG. 5. Scheduled administration of disparate anti-4-1 BB or scheduled combination with anti-PD-1 mAb enhances anti-tumour activity.

Scheduled Administration of Treg Depleting and Immunomostimulatory mAb Leads to Enhanced Anti-Cancer Therapy Our results demonstrating that the therapeutic activity of isotype variants of anti-4-BB mAb occurs via different mechanisms indicated a potential for combined use to enhance therapeutic effects. However, since depletion of Treg cells (mIgG2a) and delivery of costimulation (mIgG1) both relied on engagement of FcγRs, and appeared to do so in a competitive manner, we speculated that sequential rather than concurrent administration might be optimal. We therefore compared the therapeutic effect following concurrent and sequential administration of anti-4-1BB mIgG2a and mIgG1 mAb. (same antibodies as used above) As previously observed the mIgG2a, but not mIgG1, variant was active as single agent. Concurrent administration of mIgG2a and mIgG1 anti-4-1 BB mAb resulted in reduced therapeutic efficacy as indicated by increased tumour size (FIG. 5A) and reduced number of tumour free mice (FIG. 5B) compared to mIgG2a single agent treatment. In marked contrast, sequential delivery of first mIgG2a, to delete Treg cells, followed by agonistic mIgG1 to provide costimulation, improved both tumour growth inhibition and enhance the number of tumour free mice compared with single agent treatment with either antibody variant alone (FIGS. 5A and B). These findings demonstrated that therapeutic efficacy of FcγR-dependent immunomodulatory mAb can be optimised by sequential administration. Importantly, our findings also indicated that Treg depletion may have broad utility to improve on immune-stimulatory antibodies beyond anti-4-1 BB, especially when used in an FcgR-non competing manner.

Figure 10:
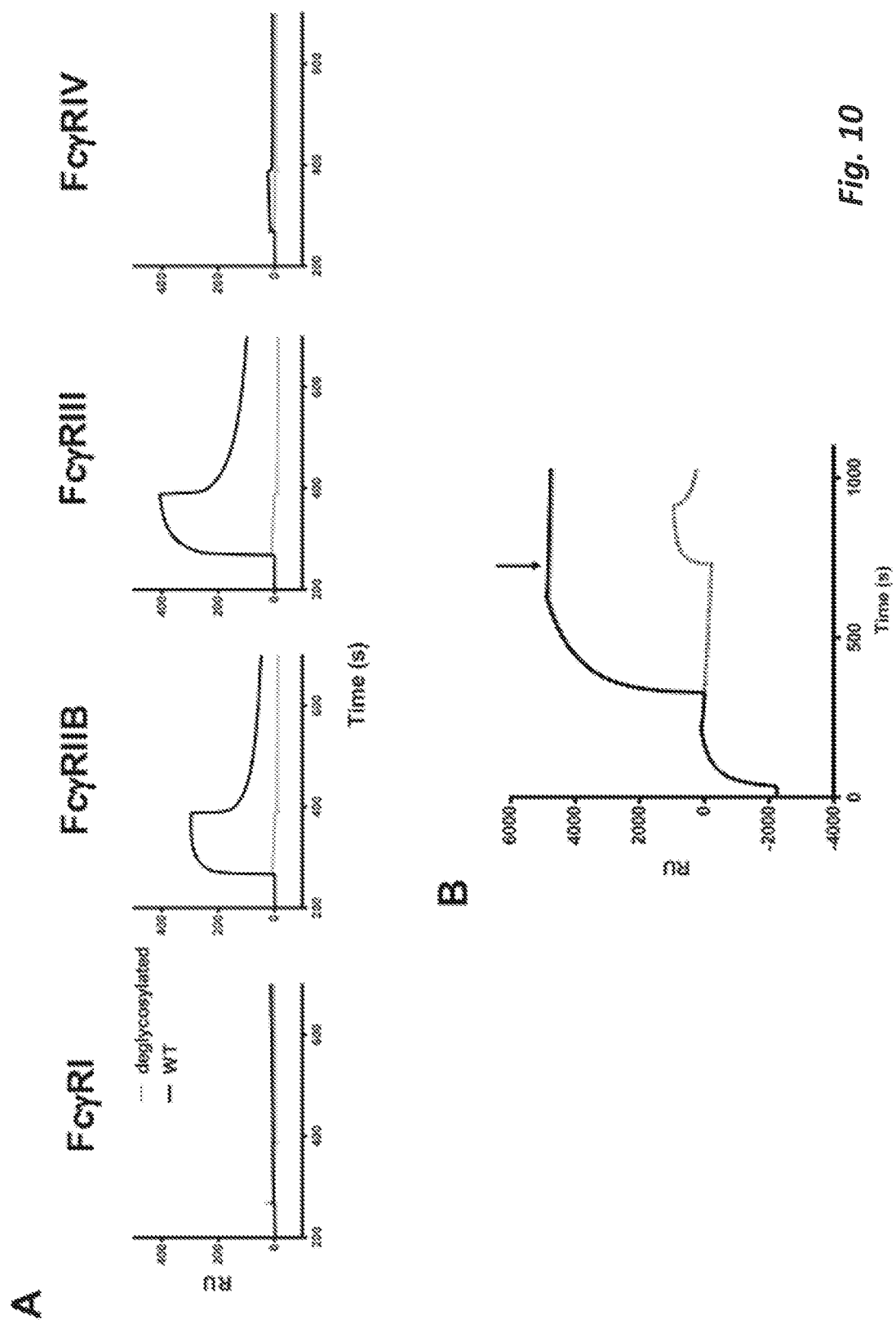
FIG. 10. Anti-PD-1 mAb characterisation.

Next, we therefore investigated the therapeutic potential of combining Treg depleting anti-4-1 BB with clinically validated immune agonist anti-PD1. We reduced the dosing of mAb to obtain suboptimal monotherapy and then combined isotype optimal anti-4-1BB mIgG2a sequentially with an FcγR null binding deglycosylated (31) variant anti-PD-1 blocking antibody (FIGS. 10A and 10B) mimicking the lack of/poor FcγR-engagement of clinically validated anti-PD-1 antibodies nivolumab and pembrolizumab. This combination produced a significant increase in therapy leading to 80% long term responders compared with 20-25% with monotherapies (FIG. 5C). Notably, the combination of suboptimal isotypes of mAb did not lead to any enhancement of responses demonstrating that for optimal combination therapies it is vital to understand the isotype and scheduling requirement of each component of any combination.

Figure 6:
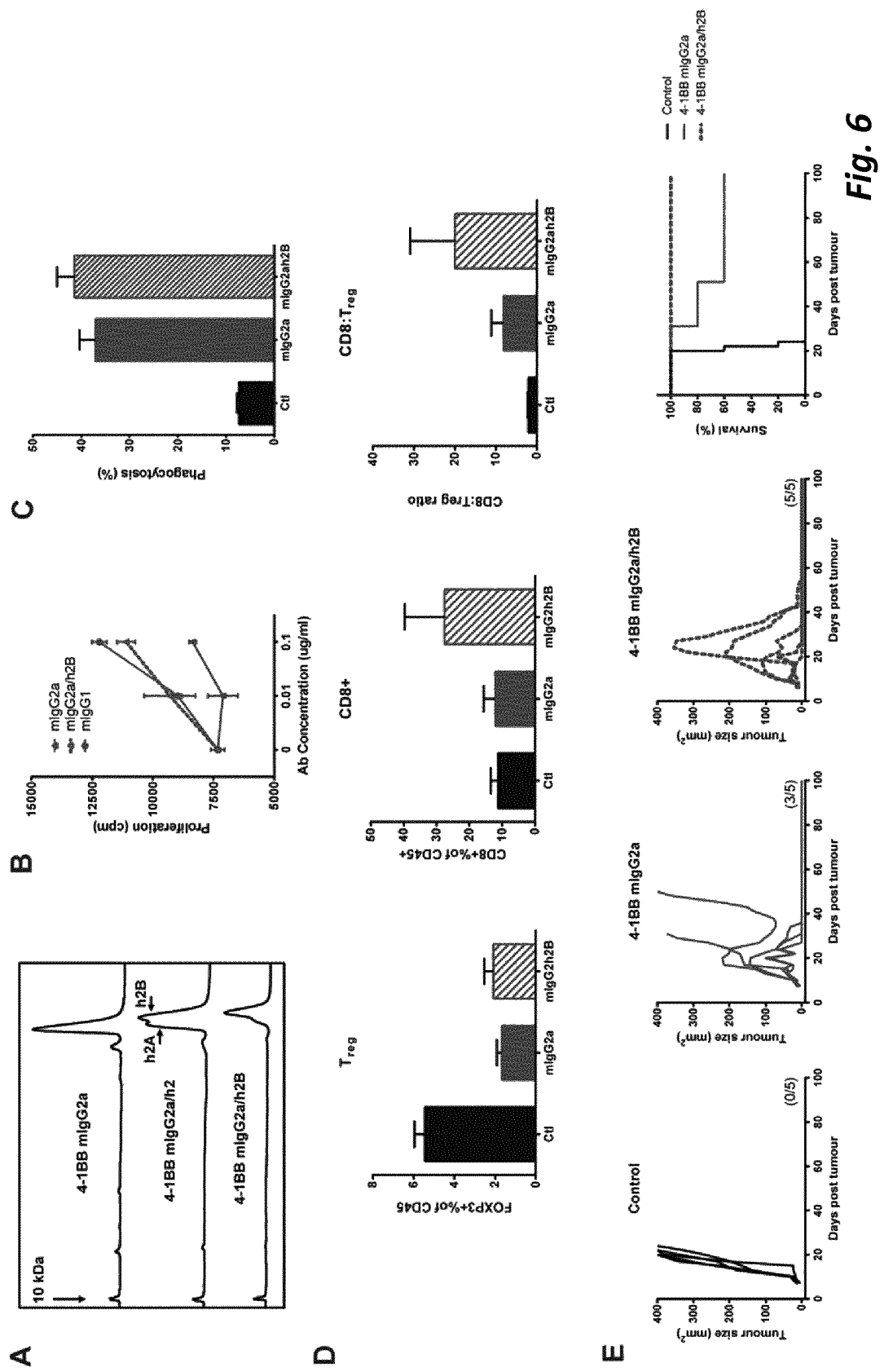
FIG. 6. Fc engineered anti-4-1 BB mIgG2a/h2B possesses dual activity and delivers augmented cancer therapy.
Figure 11:
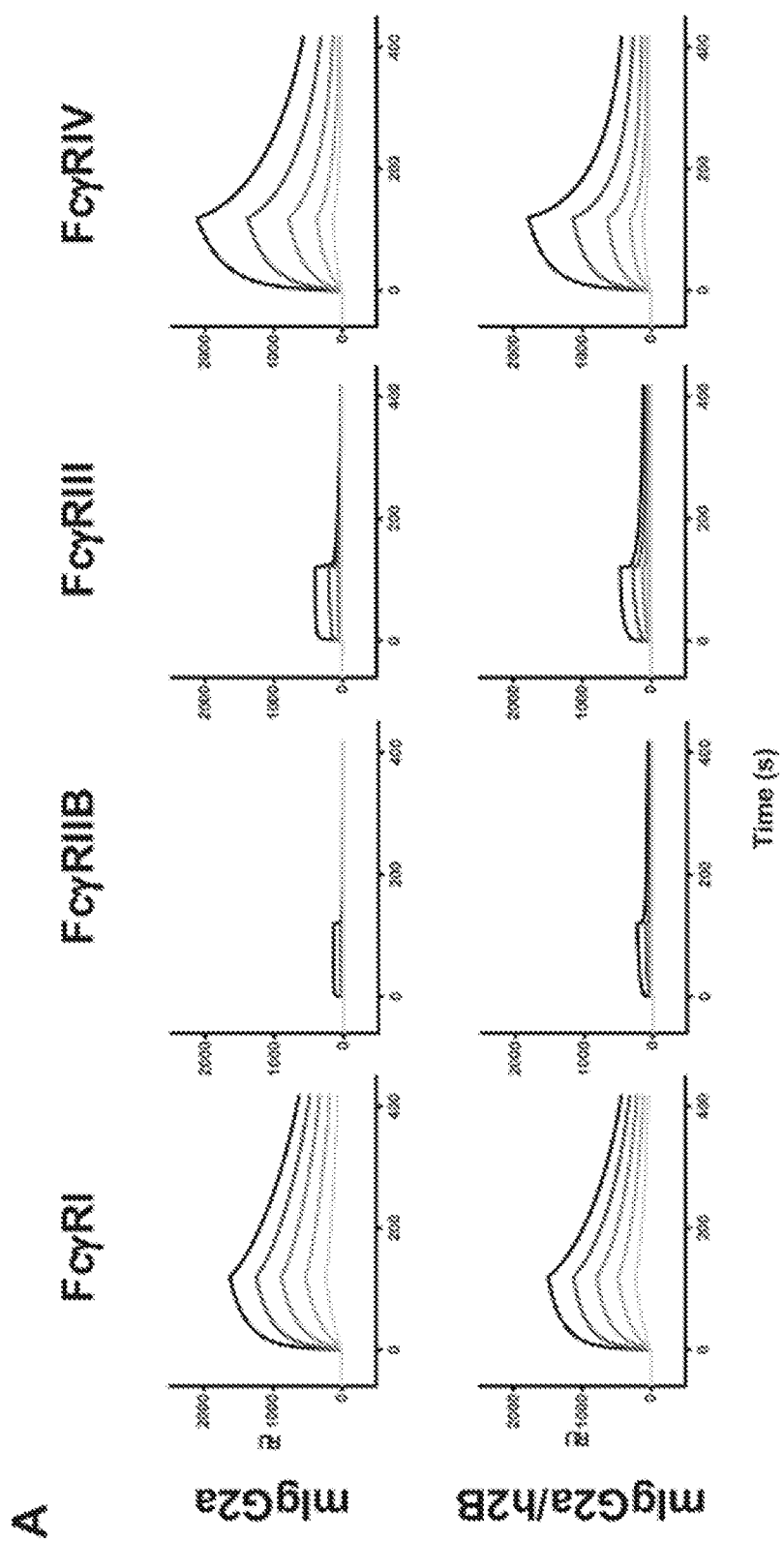
FIG. 11. Anti-4-1BB mIgG2a/h2B FcγR binding. Surface plasmon resonance analysis of anti-4-1BB (clone LOB12.0) mIgG2a and mIgG2a/h2B binding to mouse FcγRI, IIB, III and IV. Recombinant, soluble FcγR protein (0, 6, 23, 94, 375, 1500 nM) was passed over 4-1BB mAb immobilized at 5000 RU. Sensorgrams are shown.
Figure 12:
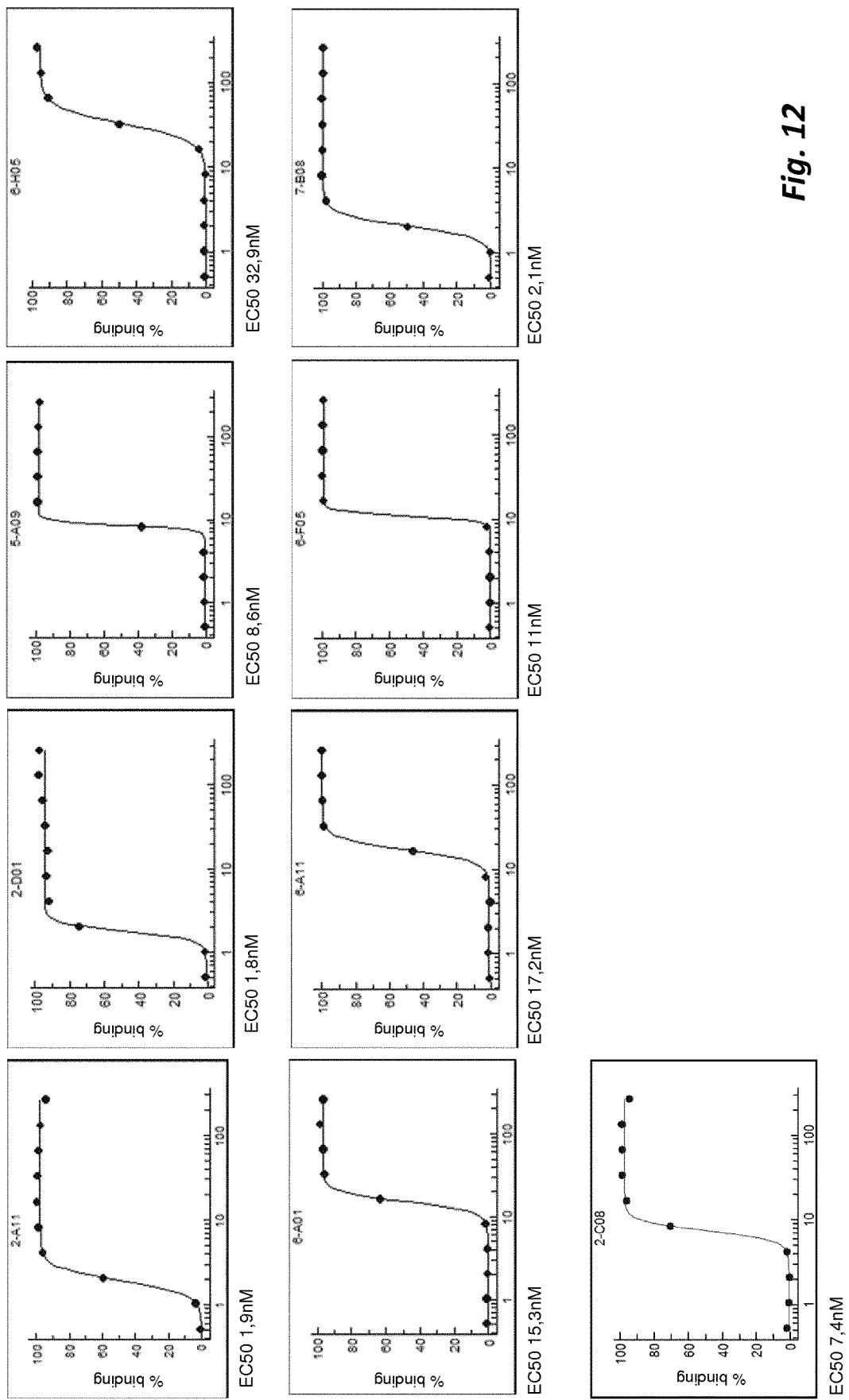
FIG. 12 shows binding titration cuves for HDLM2 cells.
Figure 14:
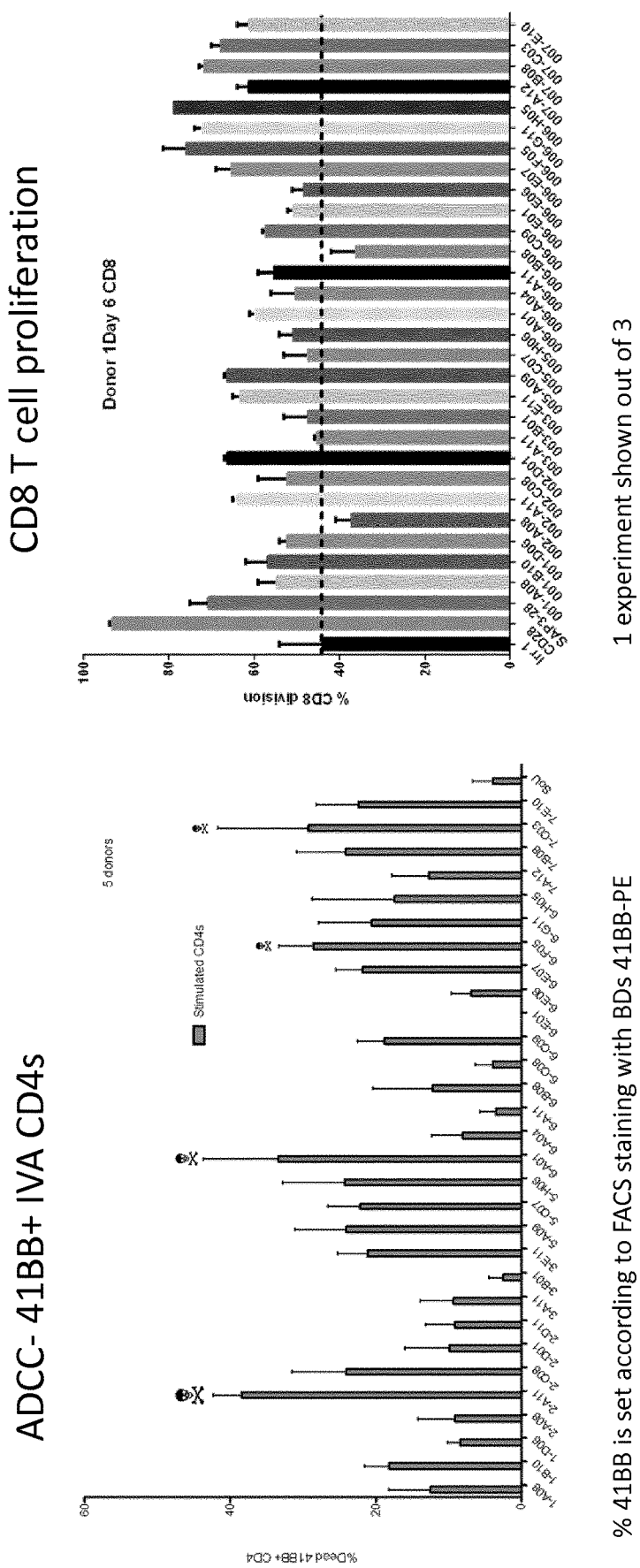
FIG. 14 shows the results of in vitro assays with ADCC for 4-1BB+ IVA CD4s in the left panel and CD8 T cell proliferation in the right panel.
Figure 15:
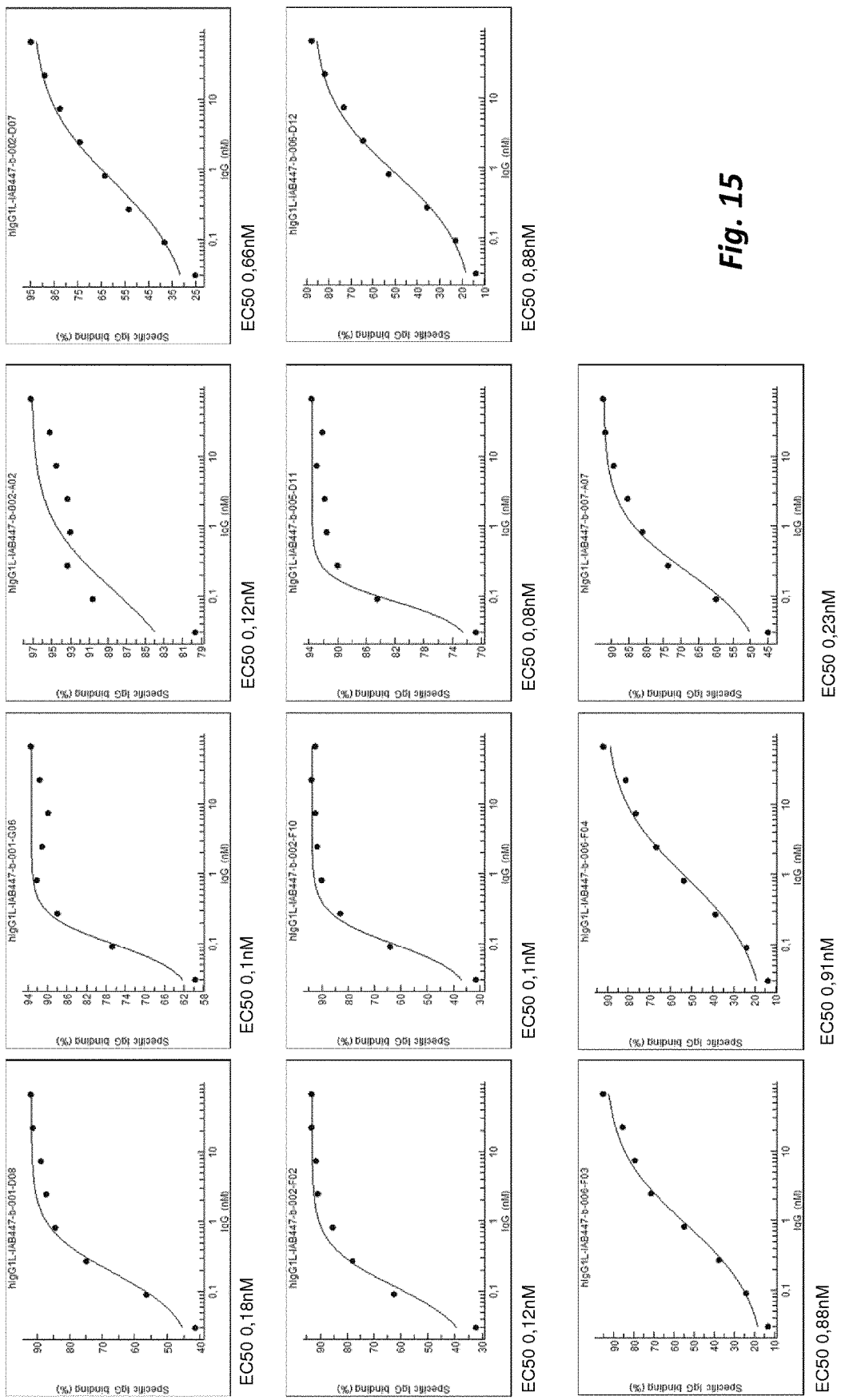
FIG. 15 shows binding to in vitro activated human CD4+ cells.
Figure 16:
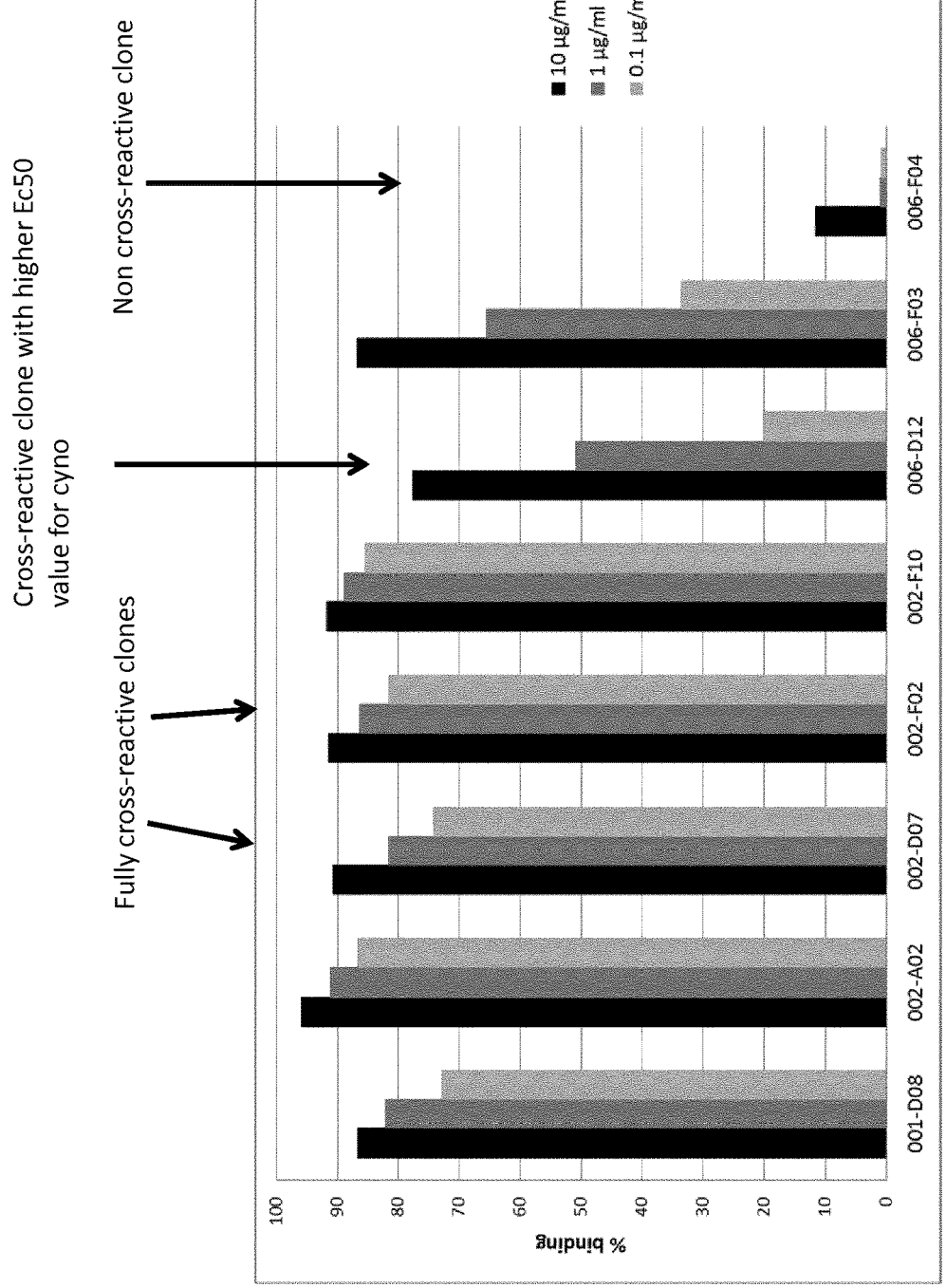
FIG. 16 shows cyon cross-reactivity on activated CD4+ T cells.
Figure 17:
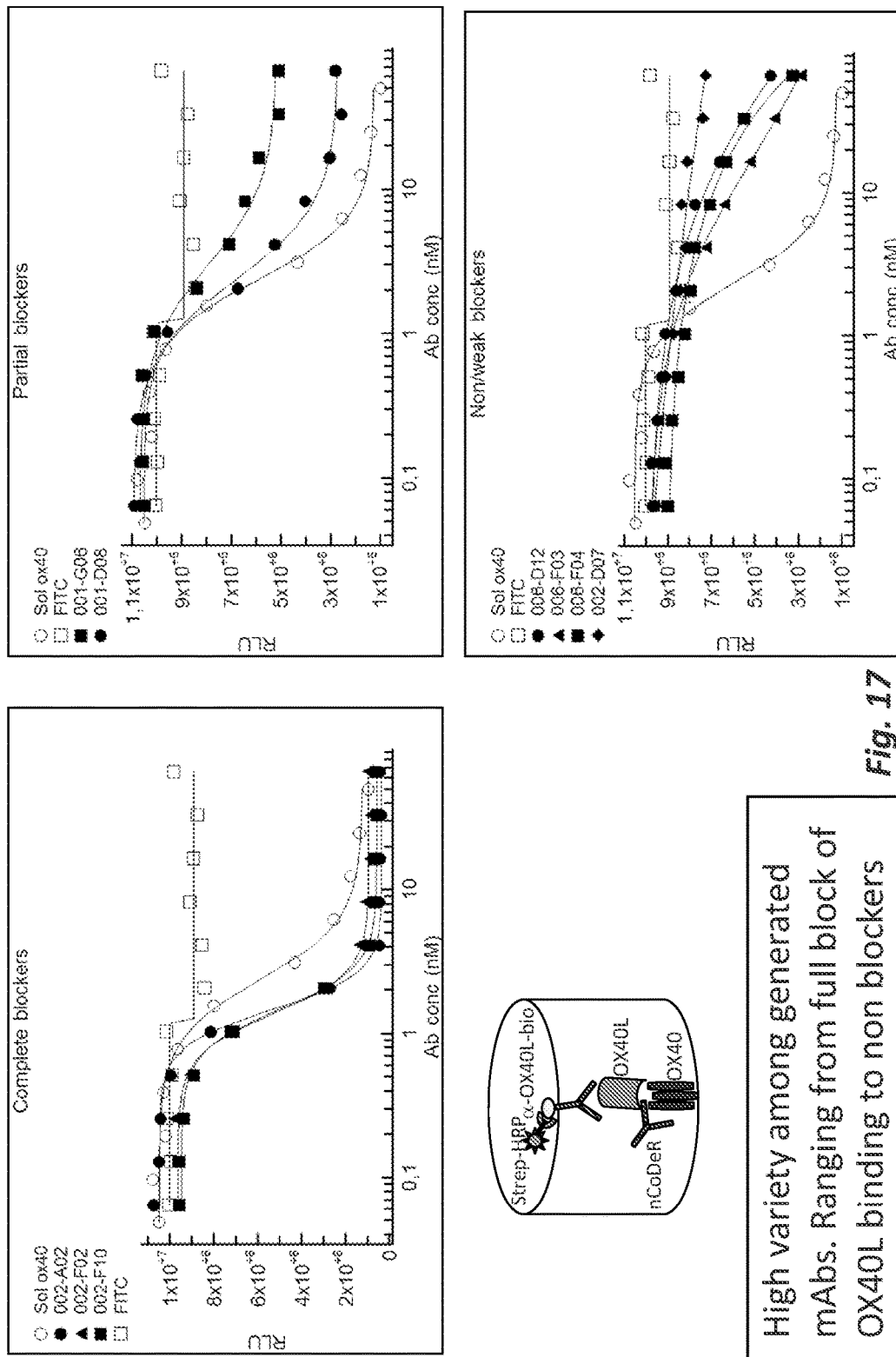
FIG. 17 shows ligand blocking.
Figure 18:
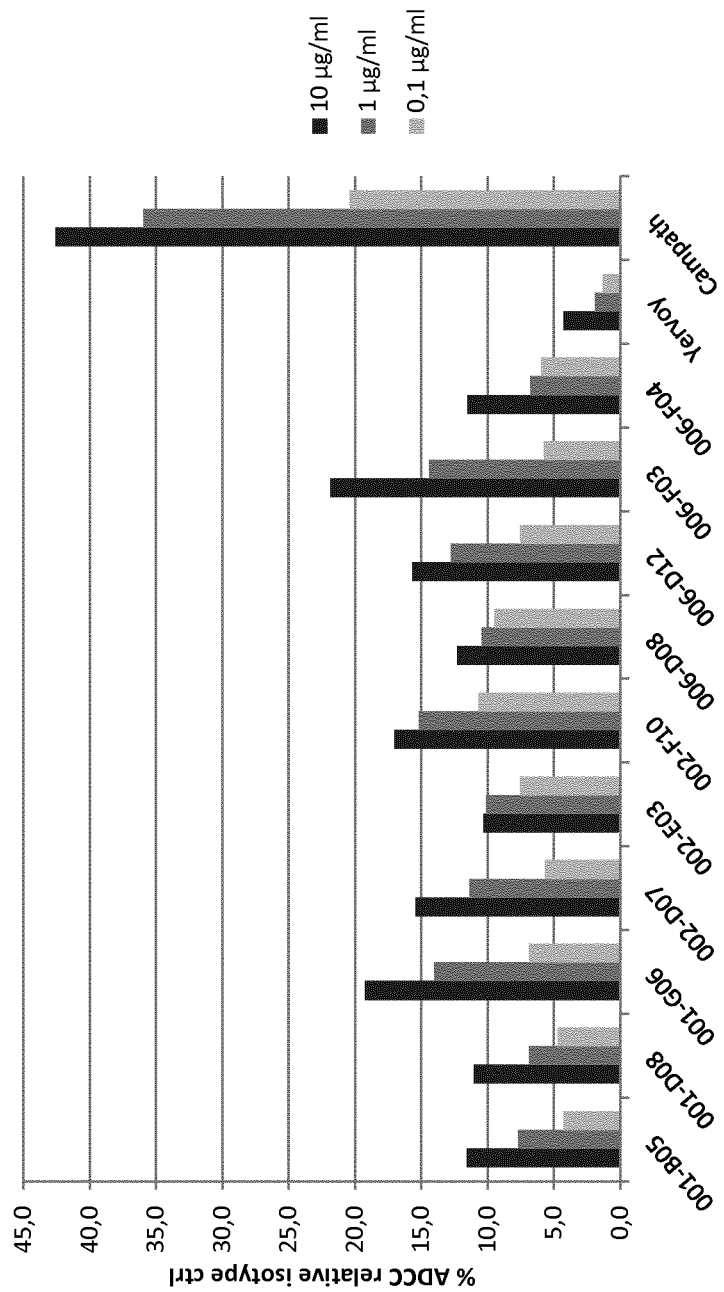
FIG. 18 shows ADCC on T cells and demonstrates that several mAbs induce significant ADCC on OX40 expressing CD4+ T cells. Figure show mean of 5 experiments. Campath is used as positive ctrl and Yervoy as comparator.
Figure 19:
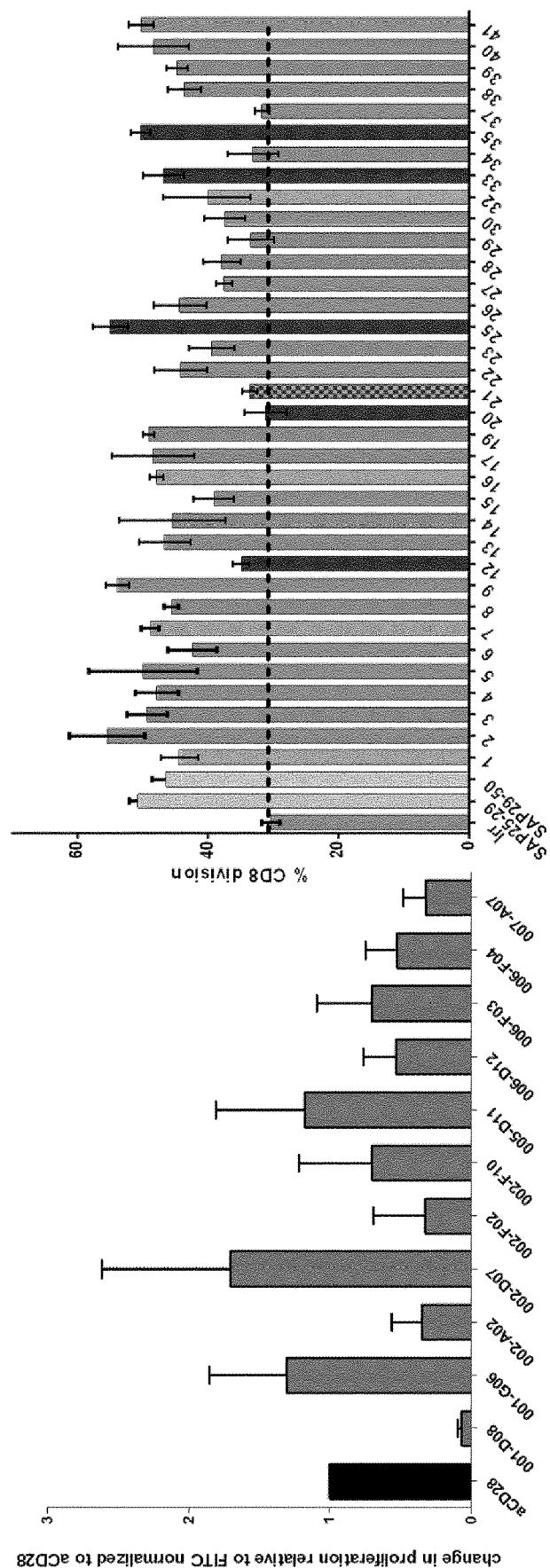
FIG. 19 shows results from proliferation assays in vitro.
Figure 20:
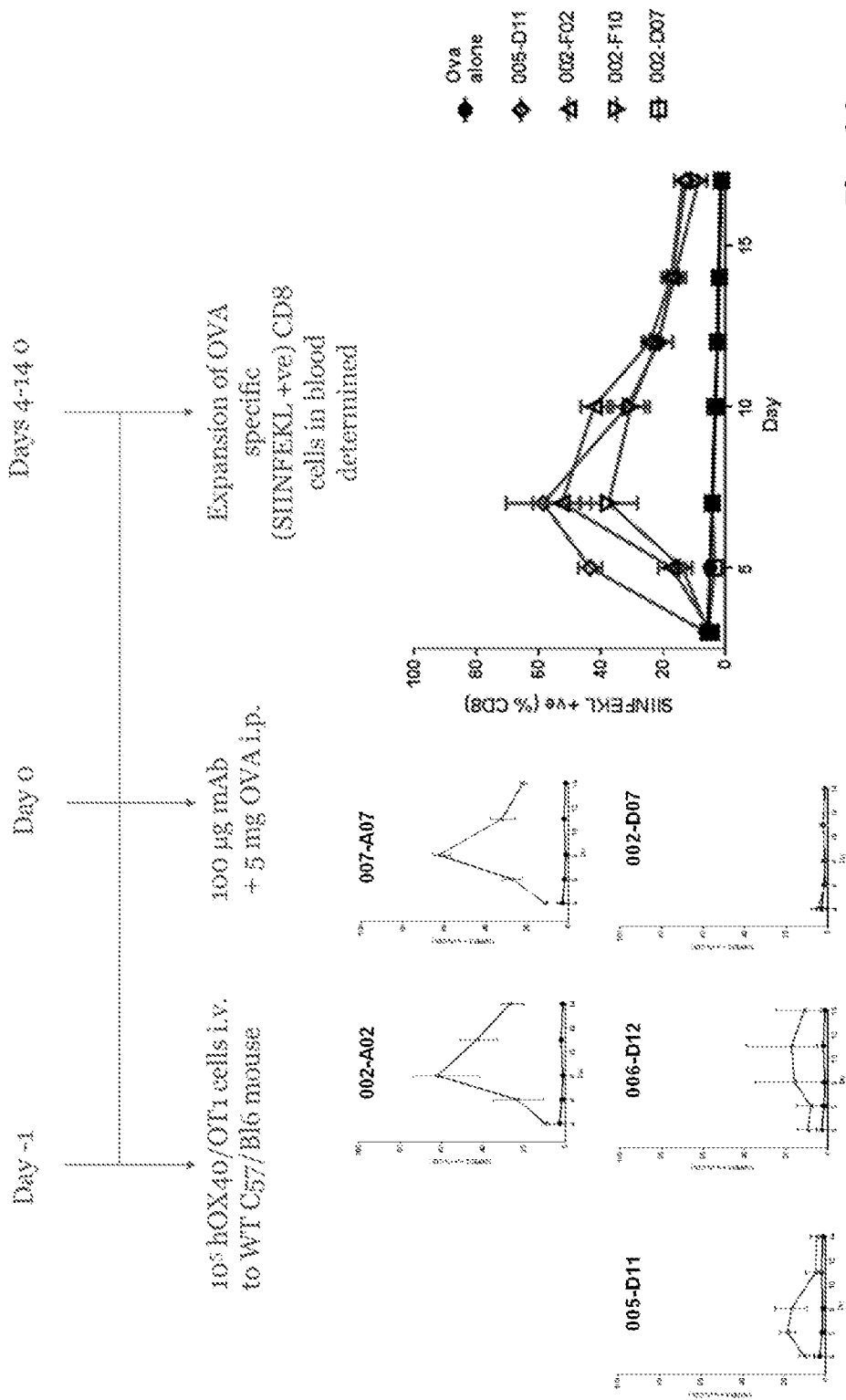
FIG. 20 demonstrates agonistic activity in vivo using h OX40 KI/OT1 transfer model for different antibodies.
Figure 22:
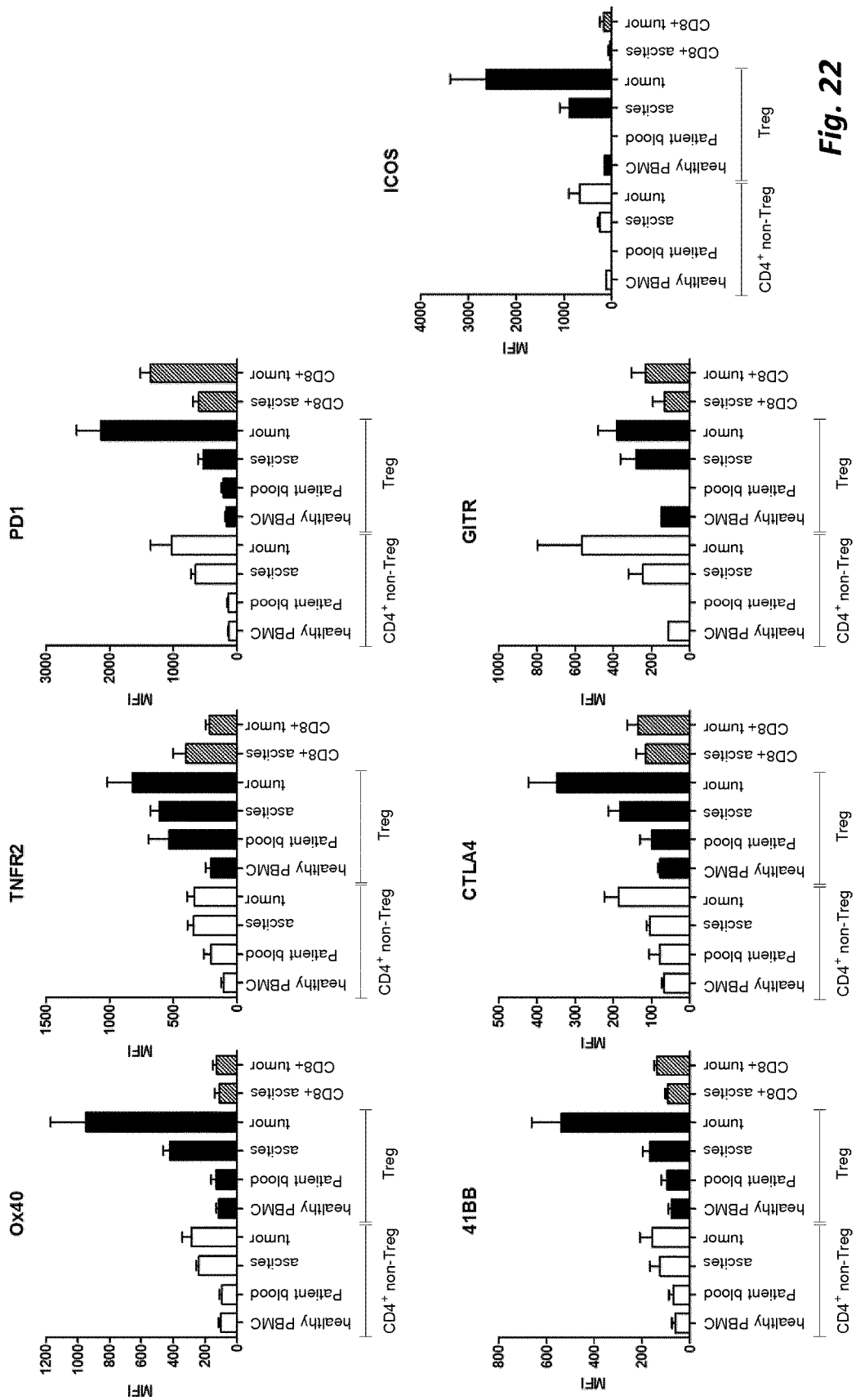
FIG. 22 shows Treg cells and effector cells from different compartments in human and demonstrates that Tregs in tumor tissue and/or in close vicinity of tumor tissue has clearly distinct potential target expression profiles compared to peripheral Tregs.
Figure 23:
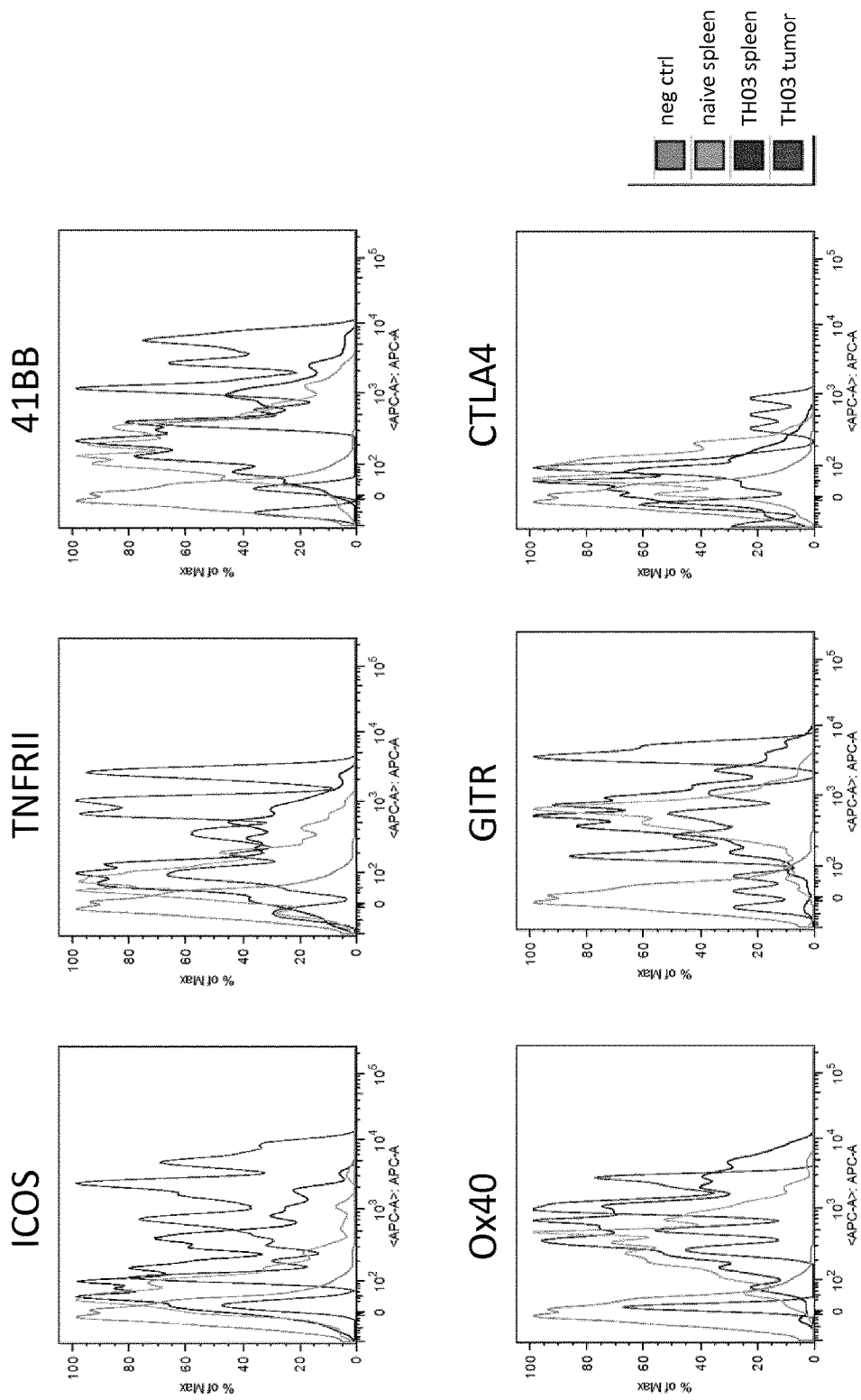
FIG. 23 shows receptor expression on Treg cells from different organs in mouse.
Figure 24:
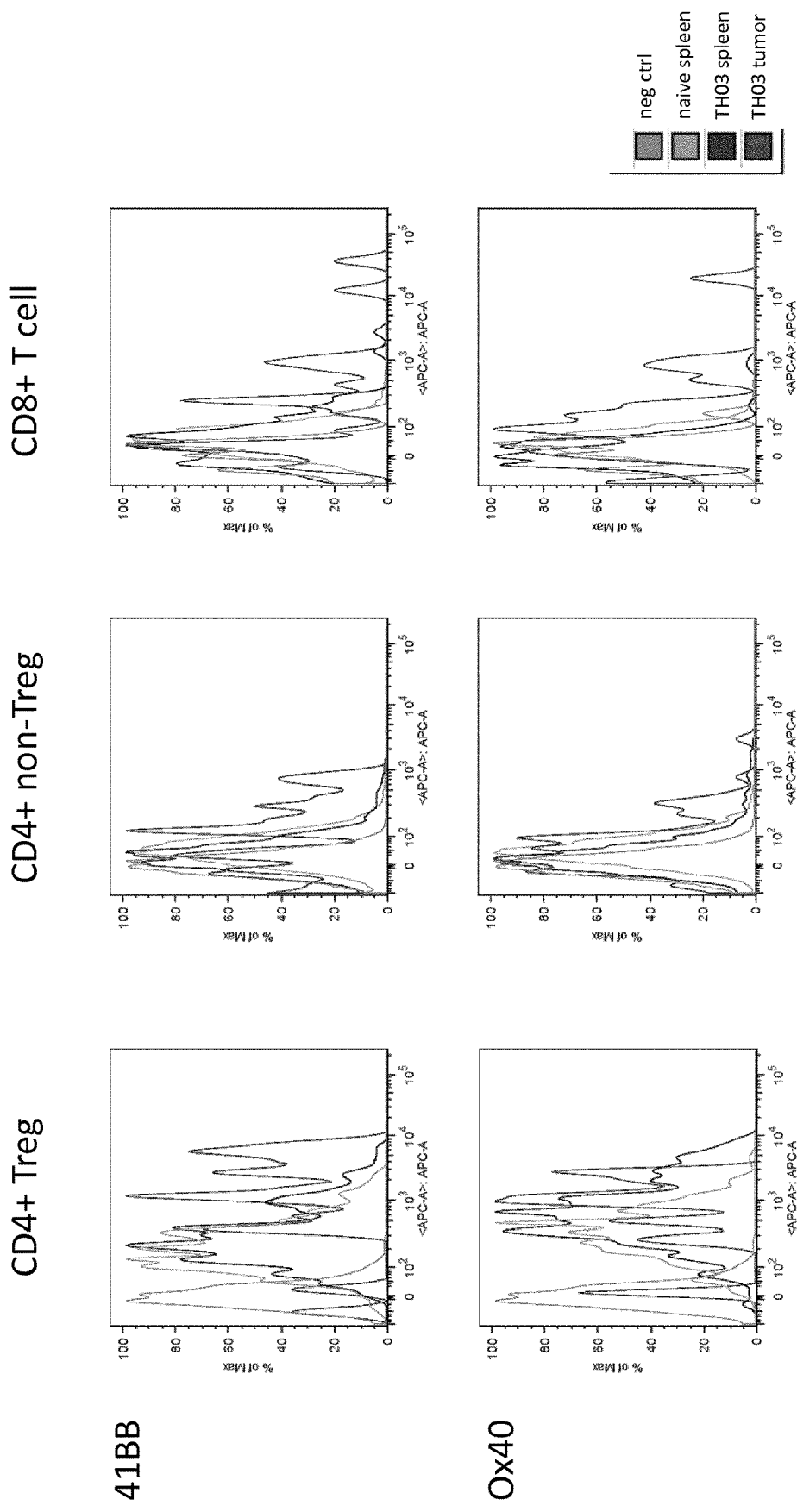
FIG. 24 shows receptor expression on Treg cells compared to other cell types in mouse.

Anti-4-1BB mIgG2a/h2B Engineered to Possess Dual Activity Delivers Augmented Cancer Therapy Having demonstrated that better responses can be achieved through optimal combination of Treg depletion and agonism/release of immune suppression than through either mechanism alone we sought to demonstrate that it is possible to deliver these multiple mechanisms through the engineering of a single mAb. Given our observations that mAb mediated Treg depletion and immunostimulatory agonism have differential and competing FcγR requirements we sought to capitalise on our previous finding that the human IgG2 hinge region is able to provide anti-TNFR superfamily member mAb with FcγR independent agonistic properties (25). Here, we cloned the human IgG2 region into the murine mIgG2a constant regions of anti-4-1 BB as detailed previously (25) and then skewed the hinge to the agonism enhanced 'B' form to make anti-4-1 BB mIgG2a/h2B (FIG. 6A). The nucleotide sequences encoding LOB12.0 mKappa is shown in SEQ. ID. NO: 183, and the corresponding amino acid sequence is shown in SEQ ID NO: 184. The nucleotide sequences encoding LOB12.0 HuIgGhinge2.mIgG2aFc (mIgG2a/h2B) is shown in SEQ. ID. NO: 185, and the corresponding amino acid sequence is shown in SEQ ID NO: 186. The nucleotide sequences encoding LOB12 human kappa is shown in SEQ. ID. NO: 187, and the corresponding amino acid sequence is shown in SEQ ID NO: 188. When tested in vitro for T cell proliferation mIgG2a/h2B had significantly enhanced agonistic activity compared to mIgG2a parent (FIG. 6B), despite an unchanged FcγR binding profile (FIG. 11). Despite this enhanced agonistic activity the engineered mAb also retained strong phagocytic potential in vitro using BMDM and 4-1BB expressing target cells (FIG. 6C) demonstrating that we had generated a reagent with both agonistic and depleting potential without competing FcγR requirements. Finally, we compared this mAb with the parental mIgG2a in the EG7 tumour model and found that the dual activity mIgG2a/h2B had equally potent Treg depleting capacity to the parental mIgG2a but now also possessed marked CD8 stimulating capability leading to an enhanced CD8/Treg ratio (FIG. 6D). This enhanced dual activity mAb also demonstrated greater therapeutic potential curing 100% of mice treated compared to 60% with the standard mIgG2a (FIG. 6E). These data demonstrate for the first time that a single mAb can be engineered to optimally mediate depletion and agonism and through this enhanced dual activity deliver better therapy.

Discussion

It has been established in a variety of in vitro and in vivo models that anti-TNFR superfamily mAb require efficient cross-linking to induce their agonistic effects and for most mAb this is best provided by inhibitory FcγR engagement (8, 9, 18, 19, 23, 32, 33). Despite these findings, it is not clear whether such agonistic engagement is the main mechanism of action that contributes to the therapeutic activity of these mAb in a solid tumour setting. We have investigated this question using mIgG2a and mIgG1 isotype anti-4-1BB mAb, which have a high and low activatory:inhibitory FcγR ratio, and consequently good depleting and agonistic potential, respectively (10).

We found using two different solid tumour models in different wild type strains of mice that mIgG2a mAb produced substantial therapeutic effects whereas mIgG1 was largely ineffective (FIG. 1A, FIG. 1B). These results are in marked contrast to the agonistic activity of these mAb on CD8+ T cells, where mIgG1 was more effective (FIG. 2A, FIG. 2B and FIG. 9A). Notably in contrast to previous publications with anti-CD40 mAb, anti-4-1 BB mIgG2a is not without T cell agonistic activity in vivo, suggesting that 4-1BB may possess a lower crosslinking threshold for signalling than CD40 (18, 19). The mIgG2a dependent therapeutic activity displayed in these different tumour models suggested that therapy was likely mediated by an effector cell dependent depletion effect. None of the tumours used were 4-1 BB positive meaning this could not be a direct tumour targeting effect as seen for anti-CD20 mAb (34).

Figure 3:
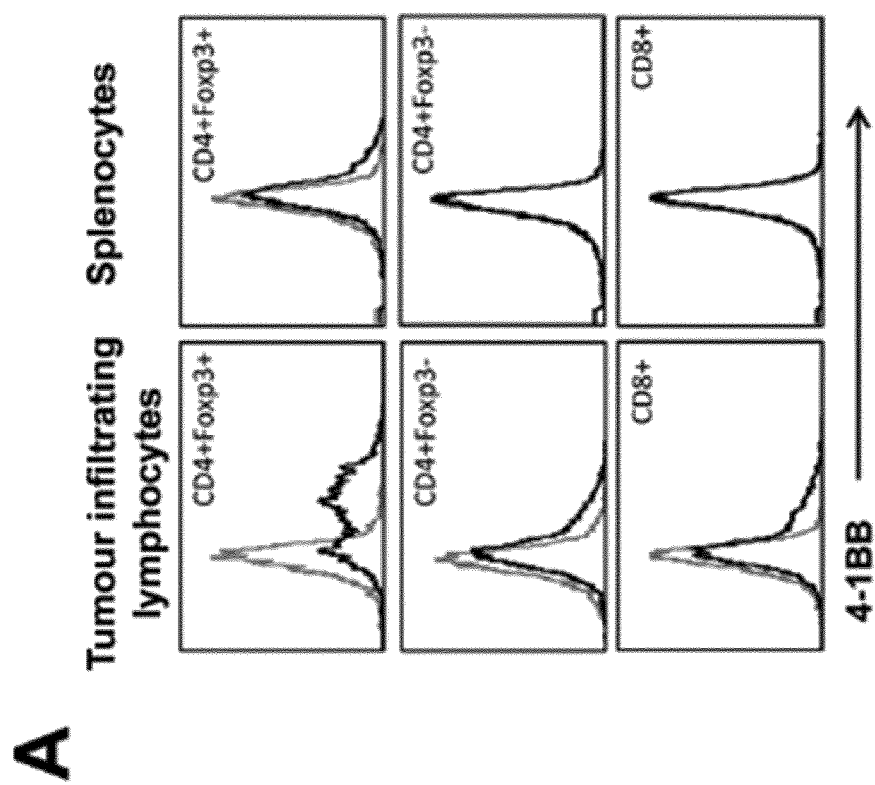
FIG. 3. Mouse and human tumour resident Treg cells preferentially express 4-1BB.

Given the recent findings that mAb targeting CTLA-4, OX40 and GITR are able to mediate therapy through intra-tumoural $T_{reg}$ depletion (5-7) we examined 4-1BB expression in these models and found that 4-1 BB was upregulated specifically on intra-tumoural Treg cells (FIG. 3A). Importantly for the potential translation of these findings to humans we found that 4-1BB demonstrated restricted expression on intratumoural Treg cells in patients with both ovarian cancer and squamous cell carcinoma (FIG. 3B and FIG. 3C, respectively) supporting the therapeutic potential of this mechanistic approach in patients. Furthermore, mIgG2a depleted this suppressive population in an activatory FcγR dependant manner, whilst mIgG1 had little effect (FIG. 4A). In keeping with the requirement for a high activatory to inhibitory FcR engagement for productive depletion, when these experiments were carried out in FcγRIIB KO mice mIgG1 became comparable to mIgG2a for its depleting capacity both in vivo (FIG. 4A) and in vitro (FIG. 4D).

Although Treg depletion was the most effective mechanism of action for 4-1 BB Ab in these models, we postulated that in the absence of competition for binding with activatory FcγR these mAb may produce a therapeutic effect through their agonistic function. We tested this potential using the CT26 model and found that in the absence of activatory FcγR, mIgG1 mAb did indeed become therapeutic (FIG. 4C). It was also notable, and in keeping with our contention that 4-1BB has a relatively low threshold for cross-linking in vivo, that in the absence of activatory FcγR mIgG2a also retained activity. In agreement with the enhanced Treg depleting activity of mIgG1 in FcγRIIB KO mice (FIG. 4A and FIG. 4C) when therapies we carried out in FcγRIIB KO mice the mIgG1 isotype mAb demonstrated enhanced and equivalent activity to mIgG2a. Furthermore, neither mAb was able to protect mice in the absence of FcγR (FIG. 4C) demonstrating both agonistic and depletion mechanisms to be FcγR dependent.

The fact that anti-4-1 BB mAb could be therapeutic using two separate mechanisms, given the provision of the appropriate FcγR, suggests that both mechanisms could be engaged if mAb were administered sequentially. Indeed this was found to be the case when mIgG2a was given first to delete Treg cells and then mIgG1 given to deliver an agonistic signal (FIG. 5A and FIG. 5B). Importantly, if the mAb were administered simultaneously then little therapeutic effect was evident. These observations support the hypothesis that simultaneous engagement of these two FcγR dependent mechanisms through the engagement of a single antigen may not be possible but that temporal, as shown here, or potentially spatial (intratumour versus systemic) separation of these mAb may facilitate their combined efficacy.

In order to further demonstrate the likely isotype and scheduling requirements for anti-4-1BB mAb in patients, where clinical results suggest combination approaches are likely to be required, we investigated different mAb combinations with anti-PD-1. In this setting we found that isotype optimal versions of both anti-4-1BB and anti-PD-1 produced a significant combination effect leading to cures in 80% of mice treated in marked contrast to monotherapies 20-25% cures and isotype suboptimal combination.

In the clinic there has been much interest in targeting 4-1BB using agonistic antibodies. However, our data show that only around 1% of CD8+ or CD4+ T cells at a tumour site express 4-1BB. Furthermore, recent findings indicate that only around 10% of CD3+CD8+ cells infiltrating the tumour site in patients with melanoma express 4-1BB, although these are enriched for tumour-reactive clones (35). Thus, our current finding that anti-4-1 BB can be used to deplete Tregs to release an immunotherapeutic response suggests that this strategy may be particularly appealing in patients. Clinical studies with other putative Treg-depleting immunotherapeutics (e.g. anti-OX40 and anti-CTLA-4) look promising (5, 36, 37) and further confirm the potential of a Treg depleting anti-4-1 BB mAb in patients.

Currently two fully humanised anti-4-1 BB mAbs are in development; urelumab (BMS-663513), an IgG4 antibody manufactured by Bristol-Myers Squibb, and PF-05082566, a fully humanised IgG2 produced by Pfizer. Thus far PF-05082566 has proven safe causing only grade 1 toxicities in patients (38) whereas urelumab caused adverse effects in 15% of patients including increased liver enzymes, pruritis and diarrhea (39). Despite their promising safety profiles, neither urelumab or PF-05082566 are predicted to strongly bind FcγRIIB calling into question whether either antibody will prove effective in patients (40). Recent data from our group show that a human IgG2 antibody targeting 4-1BB can act as a superagonist independent of FcγRs and it remains possible that PF-05082566 might act in a similar manner (25). Herein presented data, showing improved efficacy of Treg deleting compared with immune agonist variant anti-4-1 BB antibodies, and selective intratumoral 4-1BB expression on Treg compared with CD8 effector cells, support development of human therapeutic anti-4-1BB IgG1 isotype antibodies selected for capacity for Treg depletion (40). It was recently demonstrated that such Treg deleting antibodies may synergize to boost responses, and help overcome resistance, to checkpoint blockade (50).

Our findings to this point support the contention that immunomodulatory mAb can harness multiple mechanisms of action for therapy and we considered the possibility of whether a single antibody could be engineered to carry out both depletion and agonism optimally. Given our data demonstrating the competing FcγR requirements for these mechanisms in vitro and in vivo it seemed unlikely that engineering a mAb to possess enhanced activatory and inhibitory FcγR engagement would work given that any one mAb can only engage a single FcγR at a time. Given these potential limitations we generated a mIgG2a mAb with optimal depleting capacity to incorporate the hIgG2 hinge region which we skewed to the agonism optimal 'B' form. We hypothesised that this mAb would be able to perform both functions and found this to be the case both in vitro (FIGS. 6B and C) and in vivo (FIG. 6D) and that this led to enhance therapy in a solid tumour model (FIG. 6E). These results have direct implications for the administration of existing and in-development immunomodulatory mAb and for the design and development of future reagents and strategies for their use.

Sequences

```
SEQ ID NO: 179 - nucleotide sequence encoding
LOB12.0 mIgG1 heavy chain.
AAGCTTCAGGACCTCACCATGGAGATCTGGCTCAGCTTGGTTTTCCTTGTC

CTTTTCATAAAAGGTGTCCAGTGTGAGGTGCAGCTGGTGGAGTCTGGTGGA

GGCTTAGTGCAGCCTGGAAGGTCCCTGAAACTCTCCTGTGCAGCCTCAGGA

TTCACTTTCAGTAACTTTGGCATGGCCTGGGTCTGCCAGGCTCCAACGACG

GGGCTGGAGTGGGTCGCAACCATTAGTTATGATGGTACTGACAGTTACTAT

CGAGACTCCGTGAAGGACCGATTCACTATCTCCAGAGATAATGCAAAAAGC

ACCCTATACCTGCAAATGGACAGTCTGAGGTCTGAGGACACGGCCGCTTAT

TACTGTGTAAGACATGAGGATGTATACTACGGAATGGGGTACTTTGATCAC

TGGGGCCAAGGAGTACTAGTCACAGTCTCCTCAGCCAAAACGACACCCCCA

TCTGTCTATCCACTGGCCCCTGGATCTGCTGCCCAAACTAACTCCATGGTG

ACCCTGGGATGCCTGGTCAAGGGCTATTTCCCTGAGCCAGTGACAGTGACC

TGGAACTCTGGTTCCCTGTCCAGCGGTGTGCACACCTTCCCAGCTGTCCTG

CAGTCTGACCTCTACACTCTGAGCAGCTCAGTGACTGTCCCCTCCAGCACC

TGGCCCAGCGAGACCGTCACCTGCAACGTTGCCCACCCGGCCAGCAGCACC

AAGGTGGACAAGAAAATTGTGCCCAGGGATTGTGGTTGTAAGCCTTGCATA

TGTACAGTCCCAGAAGTATCATCTGTCTTCATCTTCCCCCCAAAGCCCAAG

GATGTGCTCACCATTACTCTGACTCCTAAGGTCACGTGTGTTGTGGTAGAC

ATCAGCAAGGATGATCCCGAGGTCCAGTTCAGCTGGTTTGTAGATGATGTG

GAGGTGCACACAGCTCAGACGCAACCCCGGGAGGAGCAGTTCAACAGCACT

TTCCGCTCAGTCAGTGAACTTCCCATCATGCACCAGGACTGGCTCAATGGC

AAGGAGTTCAAATGCAGGGTCAACAGTGCAGCTTTCCCTGCCCCCATCGAG

AAAACCATCTCCAAAACCAAAGGCAGACCGAAGGCTCCACAGGTGTACACC

ATTCCACCTCCCAAGGAGCAGATGGCCAAGGATAAAGTCAGTCTGACCTGC

ATGATAACAGACTTCTTCCCTGAAGACATTACTGTGGAGTGGCAGTGGAAT

GGGCAGCCAGCGGAGAACTACAAGAACACTCAGCCCATCATGGACACAGAT

GGCTCTTACTTCGTCTACAGCAAGCTCAATGTGCAGAAGAGCAACTGGGAG

GCAGGAAATACTTTCACCTGCTCTGTGTTACATGAGGGCCTGCACAACCAC

CATACTGAGAAGAGCCTCTCCCACTCTCCTGGTAAATGAGAATTC
```

SEQ ID NO: 180 - amino acid sequence of LOB12.0
mIgG1 heavy chain. The underlined sequence denotes
leader sequence.
MEIWLSLVFLVLFIKGVQCEVQLVESGGGLVQPGRSLKLSCAASGFTFSNE

GMAWVCQAPTTGLEWVATISYDGTDSYYRDSVKDRFTISRDNAKSTLYLQM

DSLRSEDTAAYYCVRHEDVYYGMGYFDHWGQGVLVTVSSAKTTPPSVYPLA

PGSAAQTNSMVTLGCLVKGYFPEPVTVTWNSGSLSSGVHTFPAVLQSDLYT

LSSSVTVPSSTWPSETVTCNVAHPASSTKVDKKIVPRDCGCKPCICTVPEV

SSVFIFPPKPKDVLTITLTPKVTCVVVDISKDDPEVQFSWFVDDVEVHTAQ

TQPREEQFNSTFRSVSELPIMHQDWLNGKEFKCRVNSAAFPAPIEKTISKT

KGRPKAPQVYTIPPPKEQMAKDKVSLTCMITDFFPEDITVEWQWNGQPAEN

YKNTQPIMDTDGSYFVYSKLNVQKSNWEAGNTFTCSVLHEGLHNHHTEKSL

SHSPGK

SEQ ID NO: 181 - nucleotide sequence encoding
LOB12.0 mIgG2a heavy chain.
AAGCTTCAGGACCTCACCATGGAGATCTGGCTCAGCTTGGTTTTCCTTGTC

CTTTTCATAAAAGGTGTCCAGTGTGAGGTGCAGCTGGTGGAGTCTGGTGGA

GGCTTAGTGCAGCCTGGAAGGTCCCTGAAACTCTCCTGTGCAGCCTCAGGA

TTCACTTTCAGTAACTTTGGCATGGCCTGGGTCTGCCAGGCTCCAACGACG

GGGCTGGAGTGGGTCGCAACCATTAGTTATGATGGTACTGACAGTTACTAT

CGAGACTCCGTGAAGGACCGATTCACTATCTCCAGAGATAATGCAAAAAGC

ACCCTATACCTGCAAATGGACAGTCTGAGGTCTGAGGACACGGCCGCTTAT

TACTGTGTAAGACATGAGGATGTATACTACGGAATGGGGTACTTTGATCAC

TGGGGCCAAGGAGTACTAGTCACAGTCTCCTCAGCCAAAACGACAGCCCCA

TCGGTCTATCCACTGGCCCCTGTGTGTGGAGATACAACTGGCTCCTCGGTG

ACTCTAGGATGCCTGGTCAAGGGTTATTTCCCTGAGCCAGTGACCTTGACC

TGGAACTCTGGATCCCTGTCCAGTGGTGTGCACACCTTCCCAGCTGTCCTG

CAGTCTGACCTCTACACCCTCAGCAGCTCAGTGACTGTAACCTCGAGCACC

TGGCCCAGCCAGTCCATCACCTGCAATGTGGCCCACCCGGCAAGCAGCACC

AAGGTGGACAAGAAAATTGAGCCCAGAGGGCCCACAATCAAGCCCTGTCCT

CCATGCAAATGCCCAGCACCTAACCTCTTGGGTGGACCATCCGTCTTCATC

TTCCCTCcaaagatcaaggatgtactcatgatctccctgagccccatagtc acatgtgtggtggtggatgtgagcgaggatgacccagatgtccagatcagC tggtttgtgaacaacgtggaagtaCaCacAGCTCAGACACAAACCCATAGA GAGGATtaCaACAGTACTCTCCGGGTGGTCAGTGCCCTCCCCATCCAGCAC

CAGGACTGGATGAGTGGCAAGGAGTTCAAATGCAAGGTCAACAACAAAGAC

CTCCCAGCGCCCATCGAGAGAACCATCTCAAAACCCAAAGGGTCAGTAAGA

GCTCCACAGGTATATGTCTTGCCTCCACCAGAAGAAGAGATGACTAAGAAA

CAGGTCACTCTGACCTGCATGGTCACAGACTTCATGCCTGAAGACATTTAC

GTGGAGTGGACCAACAACGGGAAAACAGAGCTAAACTACAAGAACACTGAA

CCAGTCCTGGACTCTGATGGTTCTTACTTCATGTACAGCAAGCTGAGAGTG

GAAAAGAAGAACTGGGTGGAAAGAAATAGCTACTCCTGTTCAGTGGTCCAC

GAGGGTCTGCACAATCACCACACGACTAAGAGCttcTCCcggaCTCCgGGT

AAATGAGAATTC

SEQ ID NO: 182 - amino acid sequence of LOB12.0
mIgG2a heavy chain. The under-lined sequence
denotes leader sequence.
MEIWLSLVFLVLFIKGVQCEVQLVESGGGLVQPGRSLKLSCAASGFTFSNE

GMAWVCQAPTTGLEWVATISYDGTDSYYRDSVKDRFTISRDNAKSTLYLQM

DSLRSEDTAAYYCVRHEDVYYGMGYFDHWGQGVLVTVSSAKTTAPSVYPLA

PVCGDTTGSSVTLGCLVKGYFPEPVTLTWNSGSLSSGVHTFPAVLQSDLYT

LSSSVTVTSSTWPSQSITCNVAHPASSTKVDKKIEPRGPTIKPCPPCKCPA

PNLLGGPSVFIFPPKIKDVLMISLSPIVTCVVVDVSEDDPDVQISWFVNNV

EVHTAQTQTHREDYNSTLRVVSALPIQHQDWMSGKEFKCKVNNKDLPAPIE

RTISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLHNH

HTTKSFSRTPGK

SEQ ID NO: 183 - nucleotide sequence encoding
LOB12.0 mKappa.
AAGCTTCAGGACCTCACCATGGCTGCACTACAACTCTTAGGGCTGCTGCTG

CTCTGGCTCCCAGCCATGAGATGTGACATCCAGATGACCCAGTCTCCTTCA

TTCCTGTCTGCATCTGTGGGAGACAGAGTCACTCTCAACTGCAAAGCAAGT

CAGAATATTAACAAGTACTTAGACTGGTATCAGCAAAAGCTGGGTGAAGCT

CCCAAACTCCTGATGTATAATACAAACAGTTTGCATACGGCAATCCCGTCA

AGGTTCAGTGGCAGTGGATCTGGTTCTGATTTCACACTTACCATAAGCAGC

CTGCAGCCTGAAGATGTTGCCACATATTTCTGCTTTCAGCATAGCAGTGGG

TGGACGTTCGGTGGAGGCACCAAGCTGGAATTGAAACGTACGgatgctgca ccaactgtatccatcttcccaccatccagtgagcagttaacatctggaggt gcctcagtcgtgtgcttcttgaacaacttctaccccaaagacatcaatgtc aagtggaagattgatggcagtgaacgacaaaatggcgtcctgaacagttgg actgatcaggacagcaaagacagcacctacagcatgagcagcaccctcacg ttgaccaaggacgagtatgaacgacataacagctatacctgtgaggccact cacaagacatcaacttcacccattgtcaagagcttcaacaggaatgagtgt taggaattc SEQ ID NO: 184 - amino acid sequence of LOB12.0
mKappa. The underlined sequence denotes leader
sequence.
MAALQLLGLLLLWLPAMRCDIQMTQSPSFLSASVGDRVTLNCKASQNINKY

LDWYQQKLGEAPKLLMYNTNSLHTAIPSRFSGSGSGSDFTLTISSLQPEDV

ATYFCFQHSSGWTFGGGTKLELKRTDAAPTVSIFPPSSEQLTSGGASVVCF

LNNFYPKDINVKWKIDGSERQNGVLNSWTDQDSKDSTYSMSSTLTLTKDEY

ERHNSYTCEATHKTSTSPIVKSFNRNEC

SEQ ID NO: 185 - nucleotide sequence encoding
LOB12.0 HuIgGhinge2.mIgG2aFc (mIgG2a/h2B).
AAGCTTCAGGACCTCACCATGGAGATCTGGCTCAGCTTGGTTTTCCTTGTC

CTTTTCATAAAAGGTGTCCAGTGTGAGGTGCAGCTGGTGGAGTCTGGTGGA

GGCTTAGTGCAGCCTGGAAGGTCCCTGAAACTCTCCTGTGCAGCCTCAGGA

TTCACTTTCAGTAACTTTGGCATGGCCTGGGTCTGCCAGGCTCCAACGACG

GGGCTGGAGTGGGTCGCAACCATTAGTTATGATGGTACTGACAGTTACTAT

CGAGACTCCGTGAAGGACCGATTCACTATCTCCAGAGATAATGCAAAAAGC

ACCCTATACCTGCAAATGGACAGTCTGAGGTCTGAGGACACGGCCGCTTAT

TACTGTGTAAGACATGAGGATGTATACTACGGAATGGGGTACTTTGATCAC

TGGGGCCAAGGAGTACTAGTcaccgtctcctcagcctccACCAAGGGCCCA

TCGGTCTTCCCCCTGGCGCCCTGCTCCAGGAGCACCTCCGAGAGCACAGCG

GCCCTGGGCTGCCTGGTCAAGGACTACTTCCCCGAACCGGTGACGGTGTCG

TGGAACTCAGGCGCTCTGACCAGCGGCGTGCACACCTTCCCAGCTGTCCTA

CAGTCCTCAGGACTCTACTCCCTCAGCAGCGTGGTGACCGTGCCCTCCAGC

AACTTCGGCACCCAGACCTACACCTGCAACGTAGATCACAAGCCCAGCAAC

ACCAAGGTGGACAAGacagttGAGCGCAAATGTTGTGTCGAGTGCCCACCG

TGCCCAGCACCTAACCTCTTGGGTGGACCATCCGTCTTCATCTTCCCTCca aagatcaaggatgtactcatgatctccctgagcccatagtcacatgtgtg gtggtggatgtgagcgaggatgacccagatgtccagatcagctggtttgtg aacaacgtggaagtaCaCacAGCTCAGACACAAACCCATAGAGAGGATtaC aACAGTACTCTCCGGGTGGTCAGTGCCCTCCCCATCCAGCACCAGGACTGG

ATGAGTGGCAAGGAGTTCAAATGCAAGGTCAACAACAAAGACCTCCCAGCG

CCCATCGAGAGAACCATCTCAAAACCCAAAGGGTCAGTAAGAGCTCCACAG

GTATATGTCTTGCCTCCACCAGAAGAAGAGATGACTAAGAAACAGGTCACT

CTGACCTGCATGGTCACAGACTTCATGCCTGAAGACATTTACGTGGAGTGG

ACCAACAACGGGAAAACAGAGCTAAACTACAAGAACACTGAACCAGTCCTG

GACTCTGATGGTTCTTACTTCATGTACAGCAAGCTGAGAGTGGAAAAGAAG

AACTGGGTGGAAAGAAATAGCTACTCCTGTTCAGTGGTCCACGAGGGTCTG

CACAATCACCACACGACTAAGAGCTtcTCCcggaCTCCgGGTAAATGAGAA

TTC

SEQ ID NO: 186 - amino acid sequence of LOB12.0
HuIgGhinge2.mIgG2aFc (mIgG2a/h2B). The underlined
sequence denotes leader sequence.
<u>MEIWLSLVFLVLFIKGVQC</u>EVQLVESGGGLVQPGRSLKLSCAASGFTFSNE

GMAWVCQAPTTGLEWVATISYDGTDSYYRDSVKDRFTISRDNAKSTLYLQM

DSLRSEDTAAYYCVRHEDVYYGMGYFDHWGQGVLVTVSSASTKGPSVFPLA

PCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPNL

LGGPSVFIFPPKIKDVLMISLSPIVTCVVVDVSEDDPDVQISWFVNNVEVH

TAQTQTHREDYNSTLRVVSALPIQHQDWMSGKEFKCKVNNKDLPAPIERTI

SKPKGSVPAPQVYVLPPPEEEMTKKQVTLTCMVTDFMPEDIYVEWTNNGKT

ELNYKNTEPVLDSDGSYFMYSKLRVEKKNWVERNSYSCSVVHEGLHNHHTT

KSFSRTPGK

SEQ ID NO: 187 - nucleotide sequence encoding LOB12
human kappa.
AAGCTTCAGGACCTCACCATGGCTGCACTACAACTCTTAGGGCTGCTGCTG

CTCTGGCTCCCAGCCATGAGATGTGACATCCAGATGACCCAGTCTCCTTCA

TTCCTGTCTGCATCTGTGGGAGACAGAGTCACTCTCAACTGCAAAGCAAGT

CAGAATATTAACAAGTACTTAGACTGGTATCAGCAAAAGCTGGGTGAAGCT

CCCAAACTCCTGATGTATAATACAAACAGTTTGCATACGGCAATCCCGTCA

AGGTTCAGTGGCAGTGGATCTGGTTCTGATTTCACACTTACCATAAGCAGC

CTGCAGCCTGAAGATGTTGCCACATATTTCTGCTTTCAGCATAGCAGTGGG

TGGACGTTCGGTGGAGGCACCAAGCTGGAATTGAAACGTACggtgGCTGCA

CCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGTC

ACAGAGCAGGACAGCAAGGACAGCACCTACAGCCTCAGCAGCACCCTGACG

CTGAGCAAAGCAGACTACGAGAAACAAAGTCTACGCCTGCGAAGTCACC

CATCAGGGCCTGAGCTCGCCCGTCACAAAGAGCTTCAACAGGGGAGAGTGT

TGAgaattc

SEQ ID NO: 188 - amino acid sequence of LOB12 human
kappa. The underlined sequence denotes leader
sequence.
<u>MAALQLLGLLLLWLPAMRC</u>DIQMTQSPSFLSASVGDRVTLNCKASQNINKY

LDWYQQKLGEAPKLLMYNTNSLHTAIPSRFSGSGSGSDFTLTISSLQPEDV

ATYFCFQHSSGWTFGGGTKLELKRTVAAPSVFIFPPSDEQLKSGTASVVCL

LNNFYPREAKVQWKVDNALQSGNSQESVTEQDSKDSTYSLSSTLTLSKADY

EKHKVYACEVTHQGLSSPVTKSFNRGEC

Methods

Animals and Cells.

Mice were bred and maintained in local facilities. Genetically altered strains used were OT1 TCR transgenic C57BL/6 mice (from Dr. Matthias Merkenschlager, Imperial College, London, U.K.), Foxp3-GFP, γ chain KO, FcγRIIB KO and FcγR null (γ chain KO×FcγRIIB KO). Mice were obtained by crossbreeding with genotypes confirmed by polymerase chain reaction (PCR) and/or flow cytometry. The CT26 colon carcinoma (16), NXS2 neuroblastoma (41), B16 Flt3vax melanoma (42) and EG7 thymoma (43) models have all been described previously.

Immunotherapy.

CT26—Groups of age and sex matched WT, γ chain KO, FcγRIIB KO or FcγR null (γ chain KO×FcγRIIB KO) BALB/c mice were challenged with $5 \times 10^4$ CT26 s.c. on day 0. When tumours were palpable mice received mAb or PBS control i.v. followed by 3 further administrations i.p. every other day (200 μg final dose unless otherwise indicated). Where CD8+ T cells were depleted, 0.5 mg of anti-CD8 (YTS169) was administered i.p. on days −1, +1, and +4 as previously described (44) prior to administration of tumour and mAb. NXS2—Groups of age and sex matched A/J mice were challenged with $2 \times 10^6$ NXS2 cells s.c. on day 0 and received antibody/peptide vaccine as specified in individual experiments. All antibodies were given i.p. in PBS. Tyrosine Hydroxylase (FETFEAKI) and control (SIINFEKL or FEANGNLI) peptides in PBS were emulsified in equal volumes of incomplete Freund's adjuvant (IFA) before intradermal injection. Tumor sizes in all models were regularly monitored by caliper and mice culled when cross-sectional area exceeded 225 mm$^2$. EG7—Groups of age and sex matched C57BL/6 were challenged with $5\times10^1$ EG7 cells s.c on day 0. On days 3, 5 and 7 mice received 200 μg mAb or PBS control i.p. as indicated. Survival period to the humane end point were plotted using the Kaplan-Meier method with analysis for significance by the log-rank test using GraphPad Prism 6.0 for Windows (GraphPad Software Inc, La Jolla, Calif.).

Antibodies and Reagents.

Anti-41BB (clone LOB12.0) mAb mIgG1, mIgG2a and mIgG2a huIgG2 hinge (mIgG2a/h2B) isotypes were constructed as previously described (18, 25; antibodies as described above). Anti-CD8 (YTS169) was produced in house. Anti-mouse PD-1 (EW1-9) mAb rIgG1 was raised using conventional hybridoma technology after immunisation of Wistar rats with recombinant mouse PD-1 (Leu25-Gln167) Fc fusion protein (RnD Systems). Spleens from immunised rats or mice were fused with NS-1 myeloma cells and plates screened by ELISA and flow cytometry. mAbs were initially screened and cells in positive wells were cloned twice and expanded in culture for IgG production. Antibodies were produced from hybridoma or CHOK1 cells and purified on Protein A with purity assessed by electrophoresis (Beckman EP system; Beckman Coulter, Buckinghamshire, UK) and lack of aggregation by SEC HPLC. All preparations were endotoxin low (<1 ng endotoxin/mg) as determined using the Endosafe-PTS portable test system (Charles River Laboratories, L'Arbresle, FR). Anti-CTLA-4 (9D9) was purchased from Bio X Cell. Anti-PD-1 de-gly was produced by treating EW1-9 with 0.05 U of PNGaseF/μg of antibody. N-Glycosidase F (PNGaseF) was obtained from Promega (V483A). Samples were kept at 37° C. overnight. De-glycosylation was confirmed either by EP or SPR analysis. Purification of antibody from enzyme was achieved through size exclusion chromatography using Sephadex™200. Peptides (SIINFEKL, FETFEAKI and FEANGNLI) were obtained from Peptide Protein Research Ltd.

In Vitro T Cell Proliferation.

Spleens from Foxp3-GFP mice were sorted to exclude GFP+ cells (−Treg cells; 99% of Treg cells removed) or null sorted and plated at $1\times10^5$ cells/well with 0.1 μg/ml anti-CD3 and a range of anti-4-1 BB mAb concentrations as indicated. 1 μCi/well [$^3$H]-thymidine was added 56 hours later and plates harvested after a further 16 hours culture.

Endogenous OVA-Specific Immune Responses.

Mice were immunised on Day 0 with 5 mg OVA (Sigma) and 200 μg mAb as specified in the description of the figures. The endogenous OVA specific CD8+ T cell expansion in peripheral blood was monitored over time and analysed by flow cytometry as described previously (18).

Lymphocyte Isolation.

Mouse—Mice challenged with CT26 or EG7 had their tumours excised and digested with 0.5 Wu/ml Liberase DL (Roche) and 50 μg/ml DNaseI (Roche) for 20 mins at 37° C. Cells were then passed through a 100 μm cell strainer and used for assays directly or tumour infiltrating lymphocytes were isolated using percoll gradient of 40% and 70%. Human—Ascitic fluid was assessed as single cell suspension that had been isolated. Ovarian tumour samples were obtained from patients undergoing surgery at the Department of Obstetrics and Gynaecology at Skånes University Hospital. The material was cut into small pieces and incubated in R10 with DNase I (Sigma) and Liberase™ (Roche Diagnostics) for 20 min at 37° C. Remaining tissue was mechanically dissociated and, together with the cell suspension, passed through a 70 μm cell strainer. Samples of freshly excised cutaneous squamous cell carcinoma (cSCC) and normal skin were obtained from patients undergoing surgery at the Dermatology Department, University Hospital Southampton NHS Foundation Trust, as approved by the South Central Hampshire B National Research Ethics Service Committee (reference number 07/H0504/187). Samples were minced and treated with 1 mg/ml collagenase IA (Sigma) and 10 μg/ml DNAse I (Sigma) in RPMI medium (Gibco) at 37° C. for 1.5 hours before straining through a 70 μm cell filter (BD) and centrifugation (600×g, 20 minutes) over an Optiprep (Axis-Shield) density gradient. Matched peripheral blood samples were obtained and peripheral blood mononuclear cells were separated by centrifugation over Lymphoprep (Axis-Shield) at 600×g for 30 minutes.

Flow cytometry.

Mouse—Cell surface staining: Isolated lymphocytes were washed and incubated with antibody in the dark for 30 minutes on ice in PBS+1% BSA (Sigma) and the cells washed once with PBS/1% BSA. After staining, samples were fixed using Erythrolyse Red Blood cell lysis buffer (AbD SeroTec). Samples were washed once with PBS/1% BSA, and run on either a BD FACSCanto II or FACSCalibur and the data analysed using FCS Express. Intracellular staining: After surface staining cells were fixed and stained intracellularly using the anti-Mouse/Rat Foxp3 Staining Set (BD Biosciences). Antibodies were anti-CD4 eF450 (GK1.5), anti-CD8-APC-eF780 (53-6.7), anti-Foxp3 APC (FJK-16), anti-4-1-BB (17-B5) (all eBioscience), anti-Ki67 APC (B56) (BD Biosciences) or isotype controls. Human—Before staining with relevant antibodies, cells from ovarian cancer patients were incubated for 10 min with 10 mg/ml KIOVIG (Baxalta). Cell viability: Cells were stained with either fixable eFluor780 Live/Dead stain (eBioscience) or aqua live/dead viability stain (Invitrogen) at 4° C. in PBS. Cell surface staining: antibodies were incubated with cells in the dark for 30 minutes at 4° C. in PBS+1% BSA (Sigma)+10% FCS (Gibco). Intracellular staining was with a Foxp3 staining buffer set (eBioscience). Cells were analysed by flow cytometry using a BD FACSAria or BD FACSVerse. Fluorophore conjugated antibodies against the following cell markers were used: Ovarian-CD4-BV510 (RPA-T4), CD25-BV421 (M-A251), anti-CD127-FITC (HIL-7R-M21), CD8-APC (RPA-T8), 41BB-PE (4B4-1), mouse IgG2a isotype, K control-PE (G155-178; all from BD Biosciences); SCC-CD3-APC-Cy7, CD4-FITC or PerCP Cy5.5, CD8-PE Cy7 (all Biolegend), 4-1BB-PE and Foxp3-APC (both eBioscience).

Antibody Dependent Cellular Phagocytosis.

ADCP assays were performed as described previously with mouse (17, 45) or human macrophages (18, 46). Briefly, bone marrow derived macrophages (BMDM) were generated from the femurs of C57BL/6 mice and cultured in complete RPMI containing 20% L929 supernatant. Alternatively, human monocyte derived macrophages (hMDMs) were generated from PBMCs and cultured in complete RPMI containing M-CSF (in house). Target cells were CFSE-stained (5 μM) then opsonised with antibody before being co-cultured with macrophages for ~1 h. Macrophages were stained with CD16-APC or F4/80-APC and samples assessed for the percentage of double positive (CFSE/APC) macrophages by flow cytometry.

Statistical Analyses.

Unpaired Students t-test analyses of data were performed or for tumour therapy experiments the survival periods to the humane end point were plotted using the Kaplan-Meier method with analysis for significance by the log-rank test. All statistical analyses were carried out using GraphPad Prism 6.0 for Windows (GraphPad Software Inc, La Jolla, Ca). Significance was accepted when $p<0.05$.

Surface Plasmon Resonance.

Analyses of anti-41BB mAb and soluble FcγR interactions were assayed using a Biacore T100 (GE Healthcare Life Sciences, Buckinghamshire, UK). Antibodies or BSA as a control were immobilized at 5000 resonance units [RU]) to the flow cells of CM5 sensor chips (GE Healthcare Life Sciences, Buckinghamshire, UK) by standard amine coupling according to the manufacturer's instructions. Soluble FcγR (R&D Systems, Abingdon, U.K.) were injected through the flow cells at 1500, 375, 94, 23, 6, and 0 nM in HBS-EP+ running buffer (GE Healthcare Life Sciences, Buckinghamshire, UK) at a flow rate of 30 μl/min. Soluble Fc receptor was injected for 2 min, and dissociation was monitored for 5 min. Background binding to the control flow cell was subtracted automatically. Affinity constants were derived from the data by equilibrium binding analysis as indicated using Biacore Bioevaluation software (GE Healthcare Life Sciences, Buckinghamshire, UK).

In Vitro Binding Assays.

Karpas-299 cells stably transduced with a tail-less form of murine 4-1BB (pTL) (47) were incubated with the concentrations of anti-4-1 BB mAb indicated at 4° C. for 20 mins prior to washing and staining with a PE-labelled anti-mouse or PE-labelled anti-rat secondary antibody (both Jackson labs). No staining was observed to Karpas-299 cells stably expressing an empty vector control (data not shown). For the competitive binding assay, 0.1 μg/ml parental rat anti-4-1 BB mAb was mixed with graded concentrations of either mIgG1 or mIgG2a versions of anti-4-1 BB as indicated prior to incubation with Karpas-299 pTL cells. Cells were washed and stained with an APC-conjugated and mouse-adsorbed donkey anti-rat secondary antibody; the secondary antibody did not bind to either mIgG1 or mIgG2a. Flow cytometric analysis was performed using a BD FACS Canto II and FACS Diva software.

OVA-Specific Immune Responses.

Splenocytes from OTI transgenic mice were harvested and washed. Approximately $2 \times 10^5$ OVA-specific CD8 T cells were then transferred into recipient mice by tail vein injection. The following day mice were immunised with OVA (Sigma) as described for individual experiments. OTI expansion in peripheral blood was analysed by flow cytometry as described previously (18). Results at the peak of the response are shown (4-5 days post immunisation).

Tumour Challenge.

B16-sFlt3L-Ig (FVAX)—Groups of C57BL/6 mice were challenged with $2.5 \times 10^4$ B16/BL6 cells intra-dermally on day 0. On days 3, 6 and 9 mice received $1 \times 10^6$ irradiated FVAX cells i.d. on the opposite flank and either PBS, 100 μg anti-CTLA-4 (clone 9D9) or anti-CTLA-4 and 300 μg anti-4-1 BB antibodies as indicated i.p. also on day 3, 6 and 9 based on our previously published protocol (48).

Examples Relating to Specific 4-1BB Antibodies and Specific OX40 Antibodies

Material and Methods

Animals and Cells

Mice were bred and maintained in local facilities in accordance with home office guidelines. Ten to twelve week-old female BALB/c and C57 bl6 mice were supplied by Taconic (Bomholt, Denmark) and maintained in local animal facilities. For the xenograft studies with primary tumor cells, 6-8 week-old female BALB/c and C57 bl6 mice were grafted with syngeneic tumor cell lines CT26 and TH03, respectively.

Clinical Samples

Ethical approval for the use of clinical samples was obtained by the Ethics Committee of Skåne University Hospital. Informed consent was provided in accordance with the Declaration of Helsinki. Samples were obtained through the Department of Gynocology and Department of Oncology at Skane University Hospital, Lund. Ascitic fluid was assessed as single cell suspensions that had been isolated. Tumor material was cut into small pieces and incubated in R10 with DNase I (Sigma Aldrich) and Liberase™ (Roche Diagnostics) for 20 min at 37° C. Remaining tissue was mechanically crashed and, together with the cell suspension, passed through a 70 μm cell strainer. Cells isolated from ascitic fluid and tumors were stained. Data acquisition was performed using FACSVerse and data analyzed using FlowJo.

Cell Culture

Cell culture was performed in supplemented RPMI (RPMI containing 2 mM glutamine, 1 mM pyruvate, 100 IU/ml penicillin and streptomycin and 10% FBS (GIBCO by Life Technologies). Human peripheral CD4+ T-cells were purified by negative selection using MACS CD4 T-cell isolation kit (Miltenyi Biotec, UK).

Antibodies and Reagents

The following antibodies and reagents were used: purified anti-CD3 (UCHT1; R&D Systems); purified anti-CD28 (CD28.2; BioLegend); KIOVIG (Baxalta, Lessines, Belgium); Fixable Viability Dye eFluor780 (eBioscience, San Diego, Calif.). Cell Trace CFSE (dissolved in DMSO) and Propidium Iodide were from Life Technologies (Carlsbad, Calif.). Following reagents were used to stain human lymphocytes: CD4-BV510 (RPA-T4), CD25-BV421 (M-A251), anti-CD127-FITC (HIL-7R-M21), Ox40-PE (ACT35), 41BB-PE (4B4-1), ICOS-PE (DX29), GITR-PE (621), PD-1-PE (MIH4), CTLA-4-PE (BNI3), CD4-APC (RPA-T4), CD8-APC (RPA-T8), mouse IgG1, κ isotype control-PE (MOPC-21), mouse IgG2a isotype, κ control-PE (G155-178), mouse IgG2b isotype, κ control-PE (27-53; all from BD Biosciences); TNFRII-PE (FAB226P; R&D Systems). Following reagents were used to stain mouse lymphocytes: CD4-BV510 (RM4-5), CD25-BV421 (7D4), CD8-Alexa 488 (53-6.7; BD), Ox40, 41BB, TNFRII, ICOS, GITR, PD-1, CTLA-4, FITC negative control (scFv, in-house generated BioInvent).

Flow Cytometry

Flow cytometry was performed according to standard procedures. Dead cells (identified as propidium iodide[+] or using Fixable Viability Dye eFluor780) and cell aggregates were excluded from all analyses. Fluorescently conjugated mAb were purchased from BD Biosciences, eBiosciences, BioLegend or made in-house. Data acquisition was performed on a FACSVerse (BD Biosciences, Franklin Lakes, N.J.) and analyzed with FlowJo software (Tree Star, Ashland, Oreg.). For Genexpression analysis cells were sorted using a FACSAria (BD Biosciences). Staining with in-house generated scFv was detected with in-house Alexa 647 labeled, deglycosolated anti-His Tag antibody (AD1.1.10, R&D Systems). CFSE-labeling of T cells was performed according to manufacturer's instructions.

Antibody Dependent Cellular Cytotoxicity (ADCC)

ADCC assays were performed in two ways: a) ADCC assays were performed using an NK-92 cell line stably transfected to express the CD16-158V allele together with GFP (purchased from Conkwest, San Diego, Calif.) 24. CD4+ target T cells were isolated from peripheral blood of healthy donors using CD4+ T cell isolation kit (Miltenyi Biotec). Cells were stimulated for 2 d with CD3/CD28 dynabeads (Life Technologies, Thermo Fisher) and 50 ng/ml rh IL-2 (R&D Systems) at 37° C. Target cells were pre-incubated with mAB at 0.1-10 µg/ml for 30 min at 4° C. prior to mixing with NK cells. The cells were incubated for 4 h in RPMI 1640+GlutaMAX medium (Invitrogen) containing 10 mM HEPES buffer, 1 mM sodium Pyruvate and 10% FBS low IgG at a 2:1 effector:target cell ratio. Lysis was determined by flow cytometry. Briefly, at the end of the incubation, the cell suspension was stained with BV510-conjugated anti-CD4 together with 10 nM SYTOX Red dead cell stain (Invitrogen) or Fixable Viability Dye eFluor780 (eBioscience) for 20 min in the dark at 4° C. and the cells were then analyzed using a FACSVerse (BD Biosciences). b) Target cells were labelled with calcein AM, followed by the addition of diluting concentrations of Ab. Target cells were cocultured with human PBMCs at a 50:1 E:T ratio for 4 h at 37° C. The plate was centrifuged at 400 3 g for 5 min to pellet the cells, and the supernatant was transferred to a white 96-well plate. Calcein release was measured using a Varioskan (Thermo Scientific) using an excitation wavelength of 485 nm and emission wavelength, 530 nm. The percentage of maximal release was calculated as follows: % max release=(sample/triton treated)*100.

Antibody Dependent Cellular Phagocytosis (ADCP)

Target cells were labelled with 5 mM CFSE for 10 min at room temperature before washing in complete media. CFSE-labelled targets were then opsonized with diluting concentrations of Ab before coculturing at a 1:5 E:T ratio with BMDMs in 96-well plates for 1 h at 37° C. BMDMs were then labelled with anti-F4/80-allophycocyanin for 15 min at room temperature and washed with PBS twice. Plates were kept on ice, wells were scraped to collect BMDMs, and phagocytosis was assessed by flow cytometry using a FACSCalibur (BD) to determine the percentage of F4/80+ CFSE+ cells within the F4/80+ cell population.

T-Cell Proliferation Assay

The agonistic activity of antibodies was tested using two protocols: a) Antibodies were cross-linked with F(ab')2 goat anti-human IgG, Fcg fragment specific or F(ab')2 goat anti-mouse IgG, Fcg fragment specific in a molar ratio IgG:F(ab')2=1.5:1 for 1 h at RT. 1×105 MACS-purified human CD4+ T-cells were CFSE-labelled and stimulated with platebound anti-CD3 (0.5 µg/ml) and 4 µg/ml of soluble, cross-linked IgG for 3 days at 37° C. before analysis. b) Cell culture was in RPMI 1640 media (Gibco™) supplemented with 10% foetal calf serum, glutamine (2 mM), pyruvate (1 mM), penicillin, and streptomycin (100 IU/mL) at 37° C. in 5% CO2. Fresh PBMCs were labelled with 2 mM carboxyfluorescein succinimidyl ester (CFSE). PBMCs were then cultured in a 24-well plate at 1×107 cells/mL as described by Römer et al (51) for 48 hours prior to mAb stimulation assays. For PBMC stimulation, round-bottomed 96-well plates were wet-coated with 0.01 µg/mL of OKT3 antibody (in-house) in PBS for 4 hours after which excess antibody was discarded and the plates were washed with PBS. 1×105 PBMCs/well were transferred to the plates and stimulated with 5 µg/mL of test mAb (anti-4-1 BB, anti-OX40 mAb). On day 4 or day 5 post-stimulation, cells were labelled with anti-CD8-APC (BioLegend), and anti-CD4-PE (in-house) and proliferation was assessed by CFSE dilution on a FACSCalibur (BD Biosciences).

Ligand Blocking ELISA

Human receptors (hox40, R&D Systems; h41BB, in-house produced) were coated to 96-well plates (Lumitrac 600 LIA plate, Greiner) at 1 pmole/well. After washing, mAbs (10 µg/ml-0.01 µg/ml) were allowed to bind for 1 hour. Ligands were added at 5 nM (hox40-L, h41BB-L; R&D Systems) and the plates were further incubated for 15 minutes. After washing, bound ligand was detected with biotinylated antibodies (anti-hox40-L, anti-h41BB-L; R&D Systems) followed by Streptavidin-HRP (Jackson ImmunoResearch) with intermediate washing. Super Signal ELISA Pico (Thermo Scientific) was used as substrate and the plates were analyzed using Tecan Ultra Microplate reader.

Microarray Analysis

CD4+CD25+ target cells and CD4+CD25-non-target cells were sorted from lymph nodes of tumor-bearing mice (CT26 and TH03). CD3-non-target cells were sorted from spleens of healthy C57/B16 and Balb/c mice. CD8+ T cells were isolated from spleens of healthy Balb/c mice. RNA from all the samples was prepared with RNA isolation Midi kit from Macherey-Nagel (Dueren, Germany) according to manufactures' instructions. Isolated RNA was amplified and prepared for hybridization to the Affymetrix Mouse Gene 2.0 ST Array at Swegene Centre for Integrative Biology at Lund University (SCIBLU), Sweden. Data analysis was performed at SCIBLU according to standard methods.

The results of the above assays and the characteristics of the antibodies studied are shown in FIGS. 12-24.

Embodiments

In the following an itemized listing of different embodiments of the invention is presented:

1. A Treg depleting antibody molecule for use in the treatment of cancer wherein the Treg depleting antibody molecule is administered sequentially with an immunostimulatory antibody molecule with the Treg depleting antibody molecule being administered prior to administration of the immunostimulatory antibody molecule.

2. A Treg depleting antibody for use according to embodiment 1, wherein said immunostimulatory antibody molecule is a CD8 activating and/or CD8 boosting antibody molecule.

3. A Treg depleting antibody molecule for use according to embodiment 1 or 2, wherein the cancer is a solid tumour.

4. A Treg depleting antibody molecule for use according to embodiment 3, wherein the solid tumour is selected from the group consisting of sarcomas, carcinomas, lymphomas and ovarian cancer.

5. A Treg depleting antibody molecule for use according to embodiment 3, wherein the solid tumour is squamous cell carcinoma (SCC), thymoma, neuroblastoma or ovarian cancer 6. A Treg depleting antibody molecule for use according any one of the embodiments 1-5, wherein said Treg depleting antibody molecule and/or said immunostimulatory antibody molecule is selected from the group consisting of a full-size antibody, a Fab, a Fv, an scFv, a Fab', and a $(Fab')_2$.

7. A Treg depleting antibody molecule for use according any one of the embodiments 1-6, wherein said Treg depleting antibody molecule and/or said immunostimulatory antibody molecule is a human or humanized antibody.

8. A Treg depleting antibody molecule for use according to any one of the embodiments 1-7, wherein said Treg depleting antibody molecule is a human IgG1 antibody.

9. A Treg depleting antibody molecule for use according to any one of the embodiments 1-8, wherein said Treg depleting antibody molecule is a human IgG1 antibody molecule engineered for improved binding to at least one activatory FcγR.

10. A Treg depleting antibody molecule for use according to any one of the embodiments 1-9, wherein said Treg depleting antibody molecule is selected from antibody molecules binding specifically to a target belonging to the tumour necrosis factor receptor superfamily (TNFRSF).

11. A Treg depleting antibody molecule for use according to embodiment 10, wherein said Treg depleting antibody molecule is an antibody molecule that binds specifically to a target selected from the group consisting of 4-1BB, OX40, and TNFR2.

12. A Treg depleting antibody molecule for use according to any one of the embodiments 1-9, wherein said Treg depleting antibody molecule is an antibody molecule that binds specifically to a target selected from GITR, ICOS, CTLA-4 and CD25.

13. A Treg depleting antibody molecule for use according to embodiment 11, wherein said Treg depleting antibody molecule is an anti-4-1BB monoclonal antibody molecule.

14. A Treg depleting antibody for use according to embodiment 13, wherein the Treg depleting antibody molecule is selected from the group consisting of antibody molecules comprising 1-6 of the CDRs selected from SEQ. ID. NOs: 1-6; 1-6 of the CDRs selected from SEQ. ID. NOs: 9-14; 1-6 of the CDRs selected from SEQ. ID. NOs: 17-22; 1-6 of the CDRs selected from SEQ. ID. NOs: 25-30; 1-6 of the CDRs selected from SEQ. ID. NOs: 33-38; 1-6 of the CDRs selected from SEQ. ID. NOs: 41-46; 1-6 of the CDRs selected from SEQ. ID. NOs: 49-54; 1-6 of the CDRs selected from SEQ. ID. NOs: 57-62; 1-6 of the CDRs selected from SEQ. ID. NOs: 65-70; 1-6 of the CDRs selected from SEQ. ID. NOs: 153-158; and 1-6 of the CDRs selected from SEQ. ID. NOs: 163-168.

15. A Treg depleting antibody for use according to embodiment 14, wherein the Treg depleting antibody molecule is selected from the group consisting of antibody molecule comprising SEQ. ID. NOs: 1-6, SEQ. ID. NOs: 9-14, SEQ. ID. NOs: 17-22, SEQ. ID. NOs: 25-30, SEQ. ID. NOs: 33-38, SEQ. ID. NOs: 41-46, SEQ. ID. NOs: 49-54, SEQ. ID. NOs: 57-62, SEQ. ID. NOs: 65-70, SEQ. ID. NOs: 153-158, and SEQ. ID. NOs: 163-168.

16. A Treg depleting antibody for use according to embodiment 14 or 15, wherein the Treg depleting antibody molecule is selected from the group consisting of antibody molecules comprising a variable heavy chain selected from the group consisting of SEQ. ID. NOs: 7, 15, 23, 31, 39, 47, 55, 63, 71, 159, and 169.

17. A Treg depleting antibody for use according to any one of the embodiments 14-16, wherein the Treg depleting antibody molecule is selected from the group consisting of antibody molecule comprising a variable light chain selected from the group consisting of SEQ. ID. NOs: 8, 16, 24, 32, 40, 48, 56, 64, 72, 160, and 170.

18. A Treg depleting antibody for use according to any one of the embodiments 14-17, wherein the Treg depleting antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; and SEQ. ID. NOs: 47 and 48; SEQ. ID. NOs: 55 and 56; SEQ. ID. NOs: 63 and 64, SEQ. ID. NOs: 71 and 72; SEQ. ID. NOs: 159 and 160; and SEQ. ID. NOs: 169 and 170.

19. A Treg depleting antibody molecule for use according to embodiment 11, wherein said Treg depleting antibody is a human anti-OX40 monoclonal antibody molecule.

20. A Treg depleting antibody for use according to embodiment 19, wherein the Treg depleting antibody molecule is selected from the group consisting of antibody molecule comprising one or more of the CDRs selected from SEQ. ID. NOs: 73-78, 81-86, 89-94, 97-102 105-110, 113-118, 121-126, 129-134, 137-142, 145-150, and 171-176.

21. A Treg depleting antibody for use according to embodiment 20, wherein the Treg depleting antibody molecule is selected from the group consisting of antibody molecules comprising SEQ. ID. NOs: SEQ. ID. NOs: 73-78, SEQ. ID. NOs: 81-86, SEQ. ID. NOs: 89-94, SEQ. ID. NOs: 97-102, SEQ. ID. NOs: 105-110, SEQ. ID. NOs: 113-118, SEQ. ID. NOs: 121-126, SEQ. ID. NOs: 129-134, SEQ. ID. NOs: 137-142, SEQ. ID. NOs: 145-150 and SEQ. ID. NOs: 177-178.

22. A Treg depleting antibody for use according to embodiment 20 or 21, wherein the Treg depleting antibody molecule is selected from the group consisting of antibody molecules comprising a variable heavy chain selected from the group consisting of SEQ. ID. NOs: 79, 87, 95, 103, 111, 119, 127, 135, 143, 151, and 177.

23. A Treg depleting antibody for use according to any one of the embodiments 20-22, wherein the Treg depleting antibody molecule is selected from the group consisting of antibody molecules comprising a variable light chain selected from the group consisting of SEQ. ID. NOs: 80, 88, 96, 104, 112, 120, 128, 136, 144, 152 and 178.

24. A Treg depleting antibody for use according to any one of the embodiments 20-23, wherein the Treg depleting antibody molecule is selected from the group consisting of antibody molecules comprising SEQ. ID. NOs: 79 and 80; SEQ. ID. NOs: 87 and 88; SEQ. ID. NOs: 95 and 96; SEQ. ID. NOs: 103 and 104; SEQ. ID. NOs: 111 and 112; SEQ. ID. NOs: 119 and 120; SEQ. ID. NOs: 127 and 128; SEQ. ID. NOs: 135 and 136; SEQ. ID. NOs: 143 and 144; SEQ. ID. NOs: 151 and 152; and SEQ. ID. NOs: 177 and 178.

25. A Treg depleting antibody molecule for use according to any one of the embodiments 1-9, wherein said Treg depleting antibody molecule is selected from antibody molecules binding specifically to a target selected from the group consisting of ICOS, GITR, CTLA-4, CD25, and neuropilin-1.

26. A Treg depleting antibody for use according to any one of the embodiments 1-25, wherein the immunostimulatory antibody molecule is a human IgG2 antibody or a human IgG4 antibody molecule.

27. A Treg depleting antibody for use according to embodiment 26, wherein the immunostimulatory antibody molecule is a human IgG2b antibody molecule.

28. A Treg depleting antibody molecule for use according to any one of the embodiments 1-27, wherein the immunostimulatory antibody molecule is engineered for enhanced binding to human FcγRIIB over activatory Fc gamma receptors.

29. A Treg depleting antibody molecule for use according to any one of the embodiments 1-28, wherein the immunostimulatory antibody molecule is an antibody that binds specifically to a target selected from the group consisting of 4-1BB, OX40, ICOS, GITR, CTLA-4 CD25, PD-1 and PDL1.

30. A Treg depleting antibody molecule for use according to embodiment 29, wherein the immunostimulatory antibody molecule is an anti-4-1BB antibody molecule.

31. A Treg depleting antibody molecule for use according to embodiment 30, wherein the immunostimulatory antibody molecule is selected from the group consisting of antibody molecules comprising one or more of the CDRs selected from SEQ. ID. NOs: 1-6, 9-14, 17-22, 25-30, 33-38, 41-46, 49-54, 57-62, 65-70, 153-158 and 163-168.

32. A Treg depleting antibody for use according to embodiment 31, wherein the immunostimulatory antibody molecule is selected from the group consisting of antibody molecule comprising SEQ. ID. NOs: 1-6, SEQ. ID. NOs: 9-14, SEQ. ID. NOs: 17-22, SEQ. ID. NOs: 25-30, SEQ. ID. NOs: 33-38, SEQ. ID. NOs: 41-46, SEQ. ID. NOs: 49-54, SEQ. ID. NOs: 57-62, SEQ. ID. NOs: 65-70, SEQ. ID. NOs: 153-158 and SEQ. ID. NOs: 163-168.

33. A Treg depleting antibody for use according to embodiment 31 or 32, wherein the immunostimulatory antibody molecule is selected from the group consisting of antibody molecules comprising a variable heavy chain selected from the group consisting of SEQ. ID. NOs: 7, 15, 23, 31, 39, 47, 55, 63, 71, 159 and 169.

34. A Treg depleting antibody for use according to any one of the embodiments 31-33, wherein the immunostimulatory antibody molecule is selected from the group consisting of antibody molecule comprising a variable light chain selected from the group consisting of SEQ. ID. NOs: 8, 16, 24, 32, 40, 48, 56, 64, 72, 160 and 170.

35. A Treg depleting antibody for use according to any one of the embodiments 31-34, wherein immunostimulatory antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; and SEQ. ID. NOs: 47 and 48; SEQ. ID. NOs: 55 and 56; SEQ. ID. NOs: 63 and 64, SEQ. ID. NOs: 71 and 72, SEQ. ID. NOs: 159 and 160, and SEQ. ID. NOs: 169 and 170.

36. A Treg depleting antibody molecule for use according to embodiment 29, wherein the immunostimulatory antibody molecule is an anti-OX40 antibody molecule.

37. A Treg depleting antibody molecule for use according to embodiment 36 wherein the immunostimulatory antibody molecule is selected from the group consisting of antibody molecule comprising one or more of the CDRs selected from SEQ. ID. NOs: 73-78, 81-86, 89-94, 97-102 105-110, 113-118, 121-126, 129-134, 137-142, 145-150, and 171-176.

38. A Treg depleting antibody for use according to embodiment 37, wherein the immunostimulatory antibody molecule is selected from the group consisting of antibody molecules comprising SEQ. ID. NOs: SEQ. ID. NOs: 73-78, SEQ. ID. NOs: 81-86, SEQ. ID. NOs: 89-94, SEQ. ID. NOs: 97-102, SEQ. ID. NOs: 105-110, SEQ. ID. NOs: 113-118, SEQ. ID. NOs: 121-126, SEQ. ID. NOs: 129-134, SEQ. ID. NOs: 137-142, SEQ. ID. NOs: 145-150, and SEQ. ID. NOs: 171-176.

39. A Treg depleting antibody for use according to embodiment 37 or 38, wherein the immunostimulatory antibody molecule is selected from the group consisting of antibody molecules comprising a variable heavy chain selected from the group consisting of SEQ. ID. NOs: 79, 87, 95, 103, 111, 119, 127, 135, 143, 151 and 177.

40. A Treg depleting antibody for use according to any one of the embodiments 37-39, wherein the immunostimulatory antibody molecule is selected from the group consisting of antibody molecules comprising a variable light chain selected from the group consisting of SEQ. ID. NOs: 80, 88, 96, 104, 112, 120, 128, 136, 144, 152 and 178.

41. A Treg depleting antibody for use according to any one of the embodiments 37-40, wherein the immunostimulatory antibody molecule is selected from the group consisting of antibody molecules comprising SEQ. ID. NOs: 79 and 80; SEQ. ID. NOs: 87 and 88; SEQ. ID. NOs: 95 and 96; SEQ. ID. NOs: 103 and 104; SEQ. ID. NOs: 111 and 112; SEQ. ID. NOs: 119 and 120; SEQ. ID. NOs: 127 and 128; SEQ. ID. NOs: 135 and 136; SEQ. ID. NOs: 143 and 144; SEQ. ID. NOs: 151 and 152; and SEQ. ID. NOs: 177-178.

42. A Treg depleting antibody molecule for use according to embodiment 29, wherein the immunostimulatory antibody molecule is a human anti-PD1 monoclonal antibody molecule, a human anti-PDL1 monoclonal antibody molecule or a human anti-CTLA-4 monoclonal antibody molecule.

43. A Treg depleting antibody molecule for use according to embodiment 42, wherein the wherein the immunostimulatory antibody molecule is a human anti-PD1 monoclonal antibody molecule selected from the group consisting of nivolumab and pembrolizumab or the anti-PDL1 antibody atezolizumab or an anti-CTLA-4 antibody selected from the group consisting of ipilimumab and tremilimumab.

44. An anti-4-1 BB antibody molecule selected from the group consisting of antibody molecules comprising one or more of the CDRs selected from SEQ. ID. NOs: 1-6, 9-14, 17-22, 25-30, 33-38, 41-46, 49-54, 57-62, 65-70, 153-158 and 163-168.

45. An anti-4-1BB antibody molecule according to embodiment 44 selected from the group consisting of antibody molecule comprising SEQ. ID. NOs: 1-6, SEQ. ID. NOs: 9-14, SEQ. ID. NOs: 17-22, SEQ. ID. NOs: 25-30, SEQ. ID. NOs: 33-38, SEQ. ID. NOs: 41-46, SEQ. ID. NOs: 49-54, SEQ. ID. NOs: 57-62, SEQ. ID. NOs: 65-70, SEQ. ID. NOs: 153-158, and SEQ. ID. NOs: 163-168.

46. An anti-4-1BB antibody molecule according to embodiment 44 or 45 selected from the group consisting of antibody molecule comprising a variable heavy chain selected from the group consisting of SEQ. ID. NOs: 7, 15, 23, 31, 39, 47, 55, 63, 71, 159, and 169.

47. An anti-4-1 BB antibody molecule according to any one of the embodiments 44-46 selected from the group consisting of antibody molecule comprising a variable light chain selected from the group consisting of SEQ. ID. NOs: 8, 16, 24, 32, 40, 48, 56, 64, 72, 160, and 170.

48. An anti-4-1 BB antibody molecule according to any one of the embodiments 44-47 selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; SEQ. ID. NOs: 47 and 48; SEQ. ID. NOs: 55 and 56; SEQ. ID. NOs: 63 and 64; SEQ. ID. NOs: 71 and 72; SEQ. ID. NOs: 159 and 160; and SEQ. ID. NOs: 169-170.

49. An anti-4-1 BB antibody molecule according to any one of the embodiments 44-48 selected from the group consisting of a full-length IgG antibody, a Fab, a $F_v$, an scFv, a Fab', and a (Fab')$_2$.

50. An anti-4-1 BB antibody molecule according to embodiment 49, wherein the full-length IgG antibody is selected from the group consisting of an IgG1, IgG2, IgG4, and an Fc-engineered variant thereof.

51. An anti-4-1 BB antibody molecule according to any one of the embodiments 44-50, wherein said Treg depleting antibody molecule and/or said immunostimulatory antibody molecule is a human or humanized antibody.

52. An anti-OX40 antibody molecule selected from the group consisting of antibody molecule comprising one or more of the CDRs selected from SEQ. ID. NOs: 73-78, 81-86, 89-94, 97-102 105-110, 113-118, 121-126, 129-134, 137-142, 145-150, and 171-176.

53. An anti-OX40 antibody molecule according to embodiment 52 selected from the group consisting of antibody molecule comprising SEQ. ID. NOs: SEQ. ID. NOs: 73-78, SEQ. ID. NOs: 81-86, SEQ. ID. NOs: 89-94, SEQ. ID. NOs: 97-102, SEQ. ID. NOs: 105-110, SEQ. ID. NOs: 113-118, SEQ. ID. NOs: 121-126, SEQ. ID. NOs: 129-134, SEQ. ID. NOs: 137-142, SEQ. ID. NOs: 145-150, and SEQ. ID. NOs: 171-176.

54. An anti-OX40 antibody molecule according to embodiment 52 or 53 selected from the group consisting of antibody molecule comprising a variable heavy chain selected from the group consisting of SEQ. ID. NOs: 79, 87, 95, 103, 111, 119, 127, 135, 143 151 and 177.

55. An anti-OX40 antibody molecule according to any one of the embodiments 52-54 selected from the group consisting of antibody molecules comprising a variable light chain selected from the group consisting of SEQ. ID. NOs: 80, 88, 96, 104, 112, 120, 128, 136, 144, 152 and 178.

56. An anti-OX40 antibody molecule according to any one of the embodiments 52-55 selected from the group consisting of antibody molecules comprising SEQ. ID. NOs: 79 and 80; SEQ. ID. NOs: 87 and 88; SEQ. ID. NOs: 95 and 96; SEQ. ID. NOs: 103 and 104; SEQ. ID. NOs: 111 and 112; SEQ. ID. NOs: 119 and 120; SEQ. ID. NOs: 127 and 128; SEQ. ID. NOs: 135 and 136; SEQ. ID. NOs: 143 and 144; SEQ. ID. NOs: 151 and 152; and SEQ. ID. NOs: 177 and 178.

57. An anti-OX40 antibody molecule according to any one of the embodiments 52-56, wherein said Treg depleting antibody molecule and/or said immunostimulatory antibody molecule is selected from the group consisting of a full-length IgG antibody, a Fab, a Fv, an scFv, a Fab', and a (Fab')$_2$.

58. An anti-OX40 antibody molecule according to embodiment 57, wherein the full-length IgG antibody is selected from the group consisting of an IgG1, IgG2, IgG4, and an Fc-engineered variant thereof.

59. An anti-OX40 antibody molecule according to any one of the embodiments 52-58, wherein said Treg depleting antibody molecule and/or said immunostimulatory antibody molecule is a human or humanized antibody.

60. An isolated nucleic acid encoding an antibody according to any one of the embodiments 44-59.

61. A vector comprising the nucleic acid according to embodiment 60.

62. A host cell comprising the vector according to embodiment 61.

63. An antibody according to any one of the embodiments 44-59 for use in medicine.

64. A pharmaceutical composition comprising an antibody according to any one of the embodiments 44-59.

65. An antibody according to embodiment 63 or a pharmaceutical composition according to embodiment 64 for use in the treatment of cancer.

66. An antibody or a pharmaceutical composition according to embodiment 65, wherein the cancer is a solid tumour.

67. An antibody or a pharmaceutical composition according to embodiment 66, wherein the solid tumour is selected from the group consisting of sarcomas, carcinomas and lymphomas.

68. An antibody or a pharmaceutical composition according to embodiment 67, wherein the solid tumour is squamous cell carcinoma (SCC), thymoma, neuroblastoma or ovarian cancer.

69. An antibody according to any one of the embodiments 44-59 or a pharmaceutical composition comprising an antibody according to any one of the embodiments 44-51 and an antibody according to any one of the embodiments 52-59.

70. An antibody according to any one of the embodiments 44-59 or a pharmaceutical composition according to embodiment 69, wherein the pharmaceutical composition is for treatment of cancer.

71. An antibody according to any one of the embodiments 44-59 or a pharmaceutical composition according to embodiment 70, wherein the cancer is a solid tumour.

72. An antibody according to any one of the embodiments 44-59 or a pharmaceutical composition according to embodiment 71, wherein the solid tumour is selected from the group consisting of sarcomas, carcinomas and lymphomas.

73. An antibody according to any one of the embodiments 44-59 or a pharmaceutical composition according to embodiment 72, wherein the solid tumour is squamous cell carcinoma (SCC), thymoma, neuroblastoma or ovarian cancer.

74. Use of an antibody according to any one of the embodiments 44-59 for the manufacture of a pharmaceutical composition for use in treatment of cancer.

75. Use according to embodiment 74, wherein the cancer is a solid tumour.

76. Use according to embodiment 75, wherein the solid tumour is selected from the group consisting of sarcomas, carcinomas and lymphomas.

77 Use according to embodiment 76, wherein the solid tumour is squamous cell carcinoma (SCC), thymoma, neuroblastoma or ovarian cancer.

78. A method for treatment of cancer in a subject, wherein a Treg depleting antibody molecule is administered to the subject, and wherein the administration of the Treg depleting antibody molecule is sequentially by administration of an immunostimulatory antibody molecule.

79. The method of embodiment 78, wherein said immunostimulatory antibody molecule is a CD8 activating and/or CD8 boosting antibody molecule.

80. The method of embodiment 78 or 79, wherein the cancer is a solid tumour.

81. The method of embodiment 80, wherein the solid tumour is selected from the group consisting of sarcomas, carcinomas and lymphomas.

82. The method of embodiment 81, wherein the solid tumour is squamous cell carcinoma (SCC), thymoma, neuroblastoma or ovarian cancer.

83. The method of any one of the embodiments 78-82, wherein said Treg depleting antibody molecule and/or said immunostimulatory antibody molecule is selected from the group consisting of a full-length IgG antibody, a Fab, a Fv, an scFv, a Fab', and a (Fab')$_2$.

84. The method of embodiment 83, wherein the full-length IgG antibody is selected from the group consisting of an IgG1, IgG2, IgG4, and an Fc-engineered variant thereof.

85. The method of any one of the embodiments 78-84, wherein said Treg depleting antibody molecule and/or said immunostimulatory antibody molecule is a human or humanized antibody.

86. The method of any one of the embodiments 78-85, wherein said Treg depleting antibody molecule is a human IgG1 antibody.

87. The method of any one of the embodiments 78-86, wherein said Treg depleting antibody molecule is a human IgG1 antibody molecule engineered for improved binding to at least one activatory FcγR.

88. The method of any one of the embodiments 78-87, wherein said Treg depleting antibody molecule is selected from antibody molecules binding specifically to a target belonging to the tumour necrosis factor receptor superfamily (TNFRSF).

89. The method of embodiment 88, wherein said Treg depleting antibody molecule is an antibody molecule that binds specifically to a target selected from the group consisting of 4-1BB, OX40, and TNFR2.

90. The method of embodiment 87, wherein said Treg depleting antibody molecule is an anti-4-1 BB monoclonal antibody molecule.

91. The method of embodiment 89, wherein the Treg depleting antibody molecule is selected from the group consisting of antibody molecules comprising one or more of the CDRs selected from SEQ. ID. NOs: 1-6, 9-14, 17-22, 25-30, 33-38, 41-46, 49-54, 57-62, 65-70, 153-158 and 163-168.

92. The method of embodiment 91, wherein the Treg depleting antibody molecule is selected from the group consisting of antibody molecule comprising SEQ. ID. NOs: 1-6, SEQ. ID. NOs: 9-14, SEQ. ID. NOs: 17-22, SEQ. ID. NOs: 25-30, SEQ. ID. NOs: 33-38, SEQ. ID. NOs: 41-46, SEQ. ID. NOs: 49-54, SEQ. ID. NOs: 57-62, SEQ. ID. NOs: 65-70, SEQ. ID. NOs: 153-158, and SEQ. ID. NOs: 163-168.

93. The method of embodiment 91 or 92, wherein the Treg depleting antibody molecule is selected from the group consisting of antibody molecules comprising a variable heavy chain selected from the group consisting of SEQ. ID. NOs: 7, 15, 23, 31, 39, 47, 55, 63, 71, 159 and 169.

94. The method of any one of the embodiments 91-93, wherein the Treg depleting antibody molecule is selected from the group consisting of antibody molecule comprising a variable light chain selected from the group consisting of SEQ. ID. NOs: 8, 16, 24, 32, 40, 48, 56, 64, 72, 160 and 170.

95. The method of any one of the embodiments 91-94, wherein the Treg depleting antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; and SEQ. ID. NOs: 47 and 48; SEQ. ID. NOs: 55 and 56; SEQ. ID. NOs: 63 and 64; SEQ. ID. NOs: 71 and 72; SEQ. ID. NOs: 159 and 160; and SEQ. ID. NOs: 169-170.

96. The method of embodiment 89, wherein said Treg depleting antibody is a human anti-OX40 monoclonal antibody molecule.

97. The method of embodiment 96, wherein the Treg depleting antibody molecule is selected from the group consisting of antibody molecule comprising one or more of the CDRs selected from SEQ. ID. NOs: 73-78, 81-86, 89-94, 97-102 105-110, 113-118, 121-126, 129-134, 137-142, 145-150, and 171-176.

98. The method of embodiment 97, wherein the Treg depleting antibody molecule is selected from the group consisting of antibody molecules comprising SEQ. ID. NOs: SEQ. ID. NOs: 73-78, SEQ. ID. NOs: 81-86, SEQ. ID. NOs: 89-94, SEQ. ID. NOs: 97-102, SEQ. ID. NOs: 105-110, SEQ. ID. NOs: 113-118, SEQ. ID. NOs: 121-126, SEQ. ID. NOs: 129-134, SEQ. ID. NOs: 137-142, SEQ. ID. NOs: 145-150, and SEQ. ID. NOs: 171-176.

99. The method of any one of the embodiments 96-98, wherein the Treg depleting antibody molecule is selected from the group consisting of antibody molecules comprising a variable heavy chain selected from the group consisting of SEQ. ID. NOs: 79, 87, 95, 103, 111, 119, 127, 135, 143, 151 and 177.

100. The method of any one of the embodiments 96-99, wherein the Treg depleting antibody molecule is selected from the group consisting of antibody molecules comprising a variable light chain selected from the group consisting of SEQ. ID. NOs: 80, 88, 96, 104, 112, 120, 128, 136, 144, 152 and 178.

101. The method of any one of the embodiments 96-100, wherein the Treg depleting antibody molecule is selected from the group consisting of antibody molecules comprising SEQ. ID. NOs: 79 and 80; SEQ. ID. NOs: 87 and 88; SEQ. ID. NOs: 95 and 96; SEQ. ID. NOs: 103 and 104; SEQ. ID. NOs: 111 and 112; SEQ. ID. NOs: 119 and 120; SEQ. ID. NOs: 127 and 128; SEQ. ID. NOs: 135 and 136; SEQ. ID. NOs: 143 and 144; SEQ. ID. NOs: 151 and 152; and SEQ. ID. NOs: 177 and 178.

102. The method of any one of the embodiments 78-87, wherein said Treg depleting antibody molecule is selected from antibody molecules binding specifically to a target selected from the group consisting of ICOS, GITR, CTLA-4, CD25 and neuropilin-1.

103. The method of any one of the embodiments 78-102, wherein the immunostimulatory antibody molecule is a human IgG2 antibody or a human IgG4 antibody molecule.

104. The method of embodiment 103, wherein the immunostimulatory antibody molecule is a human IgG2b antibody molecule.

105. The method of any one of the embodiments 78-104, wherein the immunostimulatory antibody molecule is engineered for enhanced binding to human FcγRIIB over activatory Fc gamma receptors.

106. The method of any one of the embodiments 76-105, wherein the immunostimulatory antibody molecule is an antibody that binds specifically to a target selected from the group consisting of 4-1BB, OX40, ICOS, GITR, CTLA-4 CD25, PD-1 and PDL1.

107. The method of embodiment 106, wherein the immunostimulatory antibody molecule is an anti-4-1BB antibody molecule.

108. The method of embodiment 107, wherein the immunostimulatory antibody molecule is selected from the group consisting of antibody molecules comprising one or more of the CDRs selected from SEQ. ID. NOs: 1-6, 9-14, 17-22, 25-30, 33-38, 41-46, 49-54, 57-62, 65-70, 153-158 and 163-168.

109. The method of 108, wherein the immunostimulatory antibody molecule is selected from the group consisting of antibody molecule comprising SEQ. ID. NOs: 1-6, SEQ. ID. NOs: 9-14, SEQ. ID. NOs: 17-22, SEQ. ID. NOs: 25-30, SEQ. ID. NOs: 33-38, SEQ. ID. NOs: 41-46, SEQ. ID. NOs: 49-54, SEQ. ID. NOs: 57-62, SEQ. ID. NOs: 65-70, SEQ. ID. NOs: 153-158, and SEQ. ID. NOs: 163-168.

110. The method of any one of the embodiments 107-109, wherein the immunostimulatory antibody molecule is selected from the group consisting of antibody molecules comprising a variable heavy chain selected from the group consisting of SEQ. ID. NOs: 7, 15, 23, 31, 39, 47, 55, 63, 71, 159 and 169.

111. The method of any one of the embodiments 107-110, wherein the immunostimulatory antibody molecule is selected from the group consisting of antibody molecule comprising a variable light chain selected from the group consisting of SEQ. ID. NOs: 8, 16, 24, 32, 40, 48, 56, 64, 72, 160 and 170.

112. The method of any one of the embodiments 107-111, wherein immunostimulatory antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; or SEQ. ID. NOs: 47 and 48; SEQ. ID. NOs: 55 and 56; SEQ. ID. NOs: 63 and 64; SEQ. ID. NOs: 71 and 72; SEQ. ID. NOs: 159 and 160; and SEQ. ID. NOs: 169 and 170.

113. The method of embodiment 106, wherein the immunostimulatory antibody molecule is an anti-OX40 antibody molecule.

114. The method of embodiment 113, wherein the immunostimulatory antibody molecule is selected from the group consisting of antibody molecule comprising one or more of the CDRs selected from SEQ. ID. NOs: 73-78, 81-86, 89-94, 97-102 105-110, 113-118, 121-126, 129-134, 137-142, 145-150, and 171-176.

115. The method of embodiment 114, wherein the immunostimulatory antibody molecule is selected from the group consisting of antibody molecules comprising SEQ. ID. NOs: SEQ. ID. NOs: 73-78, SEQ. ID. NOs: 81-86, SEQ. ID. NOs: 89-94, SEQ. ID. NOs: 97-102, SEQ. ID. NOs: 105-110, SEQ. ID. NOs: 113-118, SEQ. ID. NOs: 121-126, SEQ. ID. NOs: 129-134, SEQ. ID. NOs: 137-142, SEQ. ID. NOs: 145-150, and SEQ. ID. NOs: 171-176.

116. The method of any one of the embodiments 113-115, wherein the immunostimulatory antibody molecule is selected from the group consisting of antibody molecules comprising a variable heavy chain selected from the group consisting of SEQ. ID. NOs: 79, 87, 95, 103, 111, 119, 127, 135, 143, 151 and 177.

117. The method of any one of the embodiments 113-116, wherein the immunostimulatory antibody molecule is selected from the group consisting of antibody molecules comprising a variable light chain selected from the group consisting of SEQ. ID. NOs: 80, 88, 96, 104, 112, 120, 128, 136, 144, 152 and 178.

118. The method of any one of the embodiments 113-117, wherein the immunostimulatory antibody molecule is selected from the group consisting of antibody molecules comprising SEQ. ID. NOs: 79 and 80; SEQ. ID. NOs: 87 and 88; SEQ. ID. NOs: 95 and 96; SEQ. ID. NOs: 103 and 104; SEQ. ID. NOs: 111 and 112; SEQ. ID. NOs: 119 and 120; SEQ. ID. NOs: 127 and 128; SEQ. ID. NOs: 135 and 136; SEQ. ID. NOs: 143 and 144; SEQ. ID. NOs: 151 and 152; and SEQ. ID. NOs: 177 and 178.

119. The method of embodiment 106, wherein the immunostimulatory antibody molecule is human anti-PD1 monoclonal antibody molecule, a human anti-PDL1 monoclonal antibody molecule or a human anti-CTLA-4 monoclonal antibody molecule.

120. The method of embodiment 119, wherein the wherein the immunostimulatory antibody molecule is a human anti-PD1 monoclonal antibody molecule selected from the group consisting of nivolumab and pembrolizumab or the anti-PDL1 antibody atezolizumab or an anti-CTLA-4 antibody selected from the group consisting of ipilimumab and tremilimumab.

121. A use, method, antibody, nucleic acid, vector, host cell or pharmaceutical composition as described herein in the description, examples and/or figures.

REFERENCES

In the text above, reference is made to the following publications, the contents of which are hereby incorporated by reference.

1. Hodi, F. S., O'Day, S. J., McDermott, D. F., Weber, R. W., Sosman, J. A., Haanen, J. B., Gonzalez, R., Robert, C., Schadendorf, D., Hassel, J. C., et al. 2010. Improved survival with ipilimumab in patients with metastatic melanoma. *N Engi J Med* 363:711-723.
2. Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. 2012. Safety, activity, and immune correlates of anti-PD-1 antibody in cancer. *N Engl J Med* 366:2443-2454.
3. Brahmer, J. R., Tykodi, S. S., Chow, L. Q., Hwu, W. J., Topalian, S. L., Hwu, P., Drake, C. G., Camacho, L. H., Kauh, J., Odunsi, K., et al. 2012. Safety and activity of anti-PD-L1 antibody in patients with advanced cancer. *N Engl J Med* 366:2455-2465.
4. Beatty, G. L., Chiorean, E. G., Fishman, M. P., Saboury, B., Teitelbaum, U. R., Sun, W., Huhn, R. D., Song, W., Li, D., Sharp, L. L., et al. 2011. CD40 agonists alter tumor stroma and show efficacy against pancreatic carcinoma in mice and humans. *Science* 331:1612-1616.
5. Simpson, T. R., Li, F., Montalvo-Ortiz, W., Sepulveda, M. A., Bergerhoff, K., Arce, F., Roddie, C., Henry, J. Y., Yagita, H., Wolchok, J. D., et al. 2013. Fc-dependent depletion of tumor-infiltrating regulatory T cells co-defines the efficacy of antiCTLA-4 therapy against melanoma. *J Exp Med* 210:1695-1710.
6. Bulliard, Y., Jolicoeur, R., Windman, M., Rue, S. M., Ettenberg, S., Knee, D. A., Wilson, N. S., Dranoff, G., and Brogdon, J. L. 2013. Activating Fc gamma receptors contribute to the antitumor activities of immunoregulatory receptor-targeting antibodies. *J Exp Med* 210:1685-1693.
7. Marabelle, A., Kohrt, H., Sagiv-Barfi, I., Ajami, B., Axtell, R. C., Zhou, G., Rajapaksa, R., Green, M. R., Torchia, J., Brody, J., et al. 2013. Depleting tumor-specific Tregs at a single site eradicates disseminated tumors. *J Clin Invest* 123:2447-2463.
8. White, A. L., Chan, H. T., French, R. R., Beers, S. A., Cragg, M. S., Johnson, P. W., and Glennie, M. J. 2013. FcgammaRIotaIotaB controls the potency of agonistic anti-TNFR mAbs. *Cancer Immunol Immunother* 62:941-948.
9. Li, F., and Ravetch, J. V. 2013. Antitumor activities of agonistic anti-TNFR antibodies require differential FcgammaRIIIB coengagement in vivo. *Proc Natl Acad Sci USA* 110:19501-19506.
10. White, A. L., Beers, S. A., and Cragg, M. S. 2014. FcgammaRIIB as a key determinant of agonistic antibody efficacy. *Curr Top Microbiol Immunol* 382:355-372.
11. Middendorp, S., Xiao, Y., Song, J. Y., Peperzak, V., Krijger, P. H., Jacobs, H., and Borst, J. 2009. Mice deficient for CD137 ligand are predisposed to develop germinal center-derived B-cell lymphoma. *Blood* 114:2280-2289.
12. Snell, L. M., Lin, G. H., McPherson, A. J., Moraes, T. J., and Watts, T. H. 2011. T-cell intrinsic effects of GITR and 4-1BB during viral infection and cancer immunotherapy. *Immunol Rev* 244:197-217.
13. Melero, I., Hirschhorn-Cymerman, D., Morales-Kastresana, A., Sanmamed, M. F., and Wolchok, J. D. 2013. Agonist antibodies to TNFR molecules that costimulate T and NK cells. *Clin Cancer Res* 19:1044-1053.
14. McHugh, R. S., Whitters, M. J., Piccirillo, C. A., Young, D. A., Shevach, E. M., Collins, M., and Byrne, M. C. 2002. CD4(+)CD25(+) immunoregulatory T cells: gene expression analysis reveals a functional role for the glucocorticoid-induced TNF receptor. *Immunity* 16:311-323.

15. Marson, A., Kretschmer, K., Frampton, G. M., Jacobsen, E. S., Polansky, J. K., MacIsaac, K. D., Levine, S. S., Fraenkel, E., von Boehmer, H., and Young, R. A. 2007. Foxp3 occupancy and regulation of key target genes during T-cell stimulation. *Nature* 445:931-935.
16. Taraban, V. Y., Rowley, T. F., O'Brien, L., Chan, H. T., Haswell, L. E., Green, M. H., Tutt, A. L., Glennie, M. J., and Al-Shamkhani, A. 2002. Expression and costimulatory effects of the TNF receptor superfamily members CD134 (OX40) and CD137 (4-1BB), and their role in the generation of anti-tumor immune responses. *Eur J Immunol* 32:3617-3627.
17. Beers, S. A., Chan, C. H., James, S., French, R. R., Attfield, K. E., Brennan, C. M., Ahuja, A., Shlomchik, M. J., Cragg, M. S., and Glennie, M. J. 2008. Type II (tositumomab) anti-CD20 monoclonal antibody out performs type I (rituximab-like) reagents in B-cell depletion regardless of complement activation. *Blood* 112:4170-4177.
18. White, A. L., Chan, H. T., Roghanian, A., French, R. R., Mockridge, C. I., Tutt, A. L., Dixon, S. V., Ajona, D., Verbeek, J. S., Al-Shamkhani, A., et al. 2011. Interaction with FcgammaRIIB is critical for the agonistic activity of anti-CD40 monoclonal antibody. *J Immunol* 187:1754-1763.
19. White, A. L., Dou, L., Chan, H. T., Field, V. L., Mockridge, C. I., Moss, K., Williams, E. L., Booth, S. G., French, R. R., Potter, E. A., et al. 2014. Fcgamma receptor dependency of agonistic CD40 antibody in lymphoma therapy can be overcome through antibody multimerization. *J Immunol* 193:1828-1835.
20. Nimmerjahn, F., and Ravetch, J. V. 2005. Divergent immunoglobulin g subclass activity through selective Fc receptor binding. *Science* 310:1510-1512.
21. Wilson, N. S., Yang, B., Yang, A., Loeser, S., Marsters, S., Lawrence, D., Li, Y., Pitti, R., Totpal, K., Yee, S., et al. 2011. An Fcgamma receptor-dependent mechanism drives antibody-mediated target-receptor signaling in cancer cells. *Cancer Cell* 19:101-113.
22. Haynes, N. M., Hawkins, E. D., Li, M., McLaughlin, N. M., Hammerling, G. J., Schwendener, R., Winoto, A., Wensky, A., Yagita, H., Takeda, K., et al. 2010. CD11c+ dendritic cells and B cells contribute to the tumoricidal activity of anti-DR5 antibody therapy in established tumors. *J Immunol* 185:532-541.
23. Li, F., and Ravetch, J. V. 2012. Apoptotic and antitumor activity of death receptor antibodies require inhibitory Fcgamma receptor engagement. *Proc Natl Acad Sci USA* 109:10966-10971.
24. Mimoto, F., Katada, H., Kadono, S., Igawa, T., Kuramochi, T., Muraoka, M., Wada, Y., Haraya, K., Miyazaki, T., and Hattori, K. 2013. Engineered antibody Fc variant with selectively enhanced FcgammaRIIb binding over both FcgammaRIIa (R131) and FcgammaRIIa (H131). *Protein Eng Des Sel* 26:589-598.
25. White, A. L., Chan, H. T., French, R. R., Willoughby, J., Mockridge, C. I., Roghanian, A., Penfold, C. A., Booth, S. G., Dodhy, A., Polak, M. E., et al. 2015. Conformation of the human immunoglobulin g2 hinge imparts superagonistic properties to immunostimulatory anticancer antibodies. *Cancer Cell* 27:138-148.
26. Gavin, M. A., Clarke, S. R., Negrou, E., Gallegos, A., and Rudensky, A. 2002. Homeostasis and anergy of CD4(+)CD25(+) suppressor T cells in vivo. *Nat Immunol* 3:33-41.
27. Elpek, K. G., Yolcu, E. S., Franke, D. D., Lacelle, C., Schabowsky, R. H., and Shirwan, H. 2007. Ex vivo expansion of CD4+CD25+FoxP3+ T regulatory cells based on synergy between IL-2 and 4-1BB signaling. *J Immunol* 179:7295-7304.
28. Zheng, G., Wang, B., and Chen, A. 2004. The 4-1BB costimulation augments the proliferation of CD4+CD25+ regulatory T cells. *J Immunol* 173:2428-2434.
29. Plitas, G., Konopacki, C., Wu, K., Bos, P. D., Morrow, M., Putintseva, E. V., Chudakov, D. M., and Rudensky, A. Y. 2016. Regulatory T Cells Exhibit Distinct Features in Human Breast Cancer. *Immunity* 45:1122-1134.
30. De Simone, M., Arrigoni, A., Rossetti, G., Gruarin, P., Ranzani, V., Politano, C., Bonnal, R. J., Provasi, E., Sarnicola, M. L., Panzeri, I., et al. 2016. Transcriptional Landscape of Human Tissue Lymphocytes Unveils Uniqueness of Tumor-Infiltrating T Regulatory Cells. *Immunity* 45:1135-1147.
31. Tipton, T. R., Mockridge, C. I., French, R. R., Tutt, A. L., Cragg, M. S., and Beers, S. A. 2015. Anti-mouse FcgammaRIV antibody 9E9 also blocks FcgammaRIII in vivo. *Blood* 126:2643-2645.
32. Li, F., and Ravetch, J. V. 2011. Inhibitory Fcgamma receptor engagement drives adjuvant and anti-tumor activities of agonistic CD40 antibodies. *Science* 333:1030-1034.
33. Li, F., and Ravetch, J. V. 2012. A general requirement for FcgammaRIIB co-engagement of agonistic anti-TNFR antibodies. *Cell Cycle* 11:3343-3344.
34. Minard-Colin, V., Xiu, Y., Poe, J. C., Horikawa, M., Magro, C. M., Hamaguchi, Y., Haas, K. M., and Tedder, T. F. 2008. Lymphoma depletion during CD20 immunotherapy in mice is mediated by macrophage FcgammaRI, FcgammaRII, and FcgammaRIV. *Blood* 112:1205-1213.
35. Gros, A., Robbins, P. F., Yao, X., Li, Y. F., Turcotte, S., Tran, E., Wunderlich, J. R., Mixon, A., Farid, S., Dudley, M. E., et al. 2014. PD-1 identifies the patient-specific CD8(+) tumor-reactive repertoire infiltrating human tumors. *J Clin Invest* 124:2246-2259.
36. Curti, B. D., Kovacsovics-Bankowski, M., Morris, N., Walker, E., Chisholm, L., Floyd, K., Walker, J., Gonzalez, I., Meeuwsen, T., Fox, B. A., et al. 2013. OX40 is a potent immune-stimulating target in late-stage cancer patients. *Cancer Res* 73:7189-7198.
37. Sharma, P., Wagner, K., Wolchok, J. D., and Allison, J. P. 2011. Novel cancer immunotherapy agents with survival benefit: recent successes and next steps. *Nat Rev Cancer* 11:805-812.
38. Segal, N. H., Gopal, A. K., Bhatia, S., Kohrt, H., Levy, R., Pishvaian, M. J., Houot, R., Bartlett, N., Nghiem, N., Kronenberg, S. A., et al. 2014. A phase 1 study of PF-05082566 (anti-4-1BB) in patients with advanced cancer. *J Clin Oncol* 32:suppl; abstr 3007.
39. Molckovsky, A., and Siu, L. L. 2008. First-in-class, first-in-human phase I results of targeted agents: highlights of the 2008 American society of clinical oncology meeting. *J Hematol Oncol* 1:20.
40. Furness, A. J., Vargas, F. A., Peggs, K. S., and Quezada, S. A. 2014. Impact of tumour microenvironment and Fc receptors on the activity of immunomodulatory antibodies. *Trends Immunol* 35:290-298.
41. Lode, H. N., Xiang, R., Varki, N. M., Dolman, C. S., Gillies, S. D., and Reisfeld, R. A. 1997. Targeted interleukin-2 therapy for spontaneous neuroblastoma metastases to bone marrow. *J Natl Cancer Inst* 89:1586-1594.
42. Curran, M. A., and Allison, J. P. 2009. Tumor vaccines expressing flt3 ligand synergize with ctla-4 blockade to reject preimplanted tumors. *Cancer Res* 69:7747-7755.

43. Moore M W, Carbone F R, and Bevan M J. Introduction of soluble protein into the class I pathway of antigen processing and presentation. *Cell*. 1988; 54(6):777-85.
44. French, R. R., Chan, H. T., Tutt, A. L., and Glennie, M. J. 1999. CD40 antibody evokes a cytotoxic T-cell response that eradicates lymphoma and bypasses T-cell help. *Nat Med* 5:548-553.
45. Beers, S. A., French, R. R., Chan, H. T., Lim, S. H., Jarrett, T. C., Vidal, R. M., Wijayaweera, S. S., Dixon, S. V., Kim, H., Cox, K. L., et al. 2010. Antigenic modulation limits the efficacy of anti-CD20 antibodies: implications for antibody selection. *Blood* 115:5191-5201.
46. Lim, S. H., Vaughan, A. T., Ashton-Key, M., Williams, E. L., Dixon, S. V., Chan, H. T., Beers, S. A., French, R. R., Cox, K. L., Davies, A. J., et al. 2011. Fc gamma receptor IIb on target B cells promotes rituximab internalization and reduces clinical efficacy. *Blood* 118:2530-2540.
47. Buchan, S. L., and Al-Shamkhani, A. 2012. Distinct motifs in the intracellular domain of human CD30 differentially activate canonical and alternative transcription factor NF-kappaB signaling. *PLoS One* 7:e45244.
48. Curran, M. A., Kim, M., Montalvo, W., Al-Shamkhani, A., and Allison, J. P. 2011. Combination CTLA-4 blockade and 4-1BB activation enhances tumor rejection by increasing T-cell infiltration, proliferation, and cytokine production. *PLoS One* 6:e19499.
49. Dahan R, Barnhart B C, Li F, Yamniuk A P, Korman A J, Ravetch J V. Therapeutic Activity of Agonistic, Human Anti-CD40 Monoclonal Antibodies Requires Selective FcγR Engagement. Cancer Cell. 2016 Jun. 13; 29(6):820-31. doi: 10.1016/j.ccell.2016.05.001. Epub 2016 Jun. 2. PMID: 27265505.
50. Arce Vargas F, Furness A J S, Solomon I, Joshi K, Mekkaoui L, Lesko M H, Miranda Rota E, Dahan R, Georgiou A, Sledzinska A, Ben Aissa A, Franz D, Werner Sunderland M, Wong Y N S, Henry J Y, O'Brien T, Nicol D, Challacombe B, Beers S A; Melanoma TRACERx Consortium; Renal TRACERx Consortium; Lung TRACERx Consortium, Turajlic S, Gore M, Larkin J, Swanton C, Chester K A, Pule M, Ravetch J V, Marafioti T, Peggs K S, Quezada S A. Fc-Optimized AntiCD25 Depletes Tumor-Infiltrating Regulatory T Cells and Synergizes with PD-1 Blockade to Eradicate Established Tumors. Immunity. 2017 Apr. 18; 46(4):577-586. doi: 10.1016/j.immuni.2017.03.013. Epub 2017 Apr. 11. PMID: 28410988
51. Römer PS1, Berr S, Avota E, Na S Y, Battaglia M, ten Berge I, Einsele H, Hünig T.; Preculture of PBMCs at high cell density increases sensitivity of T-cell responses, revealing cytokine release by CD28 superagonist TGN1412. Blood. 2011 Dec. 22; 118(26):6772-82. doi: 10.1182/blood-2010-12-319780. Epub 2011 Sep. 19.

The invention claimed is:

1. A method of depleting Treg cells in a subject wherein a Treg depleting antibody molecule is administered sequentially with an immunostimulatory antibody molecule with the Treg depleting antibody molecule being administered prior to administration of the immunostimulatory antibody molecule, wherein the Treg depleting antibody molecule is an anti-4-1BB antibody selected from the group consisting of an antibody molecule comprising VH-CDR1, VH-CDR2, VH-CDR3, VL-CDR1, VL-CDR2 and VL-CDR3 of SEQ. ID. NOs: 1-6 or SEQ. ID. NOs: 9-14 or SEQ. ID. NOs: 17-22 or SEQ. ID. NOs: 25-30 or SEQ. ID. NOs: 33-38 or SEQ. ID. NOs: 41-46 or SEQ. ID. NOs: 49-54 or SEQ. ID. NOs: 57-62 or SEQ. ID. NOs: 65-70 or SEQ. ID. NOs: 153-158 or SEQ. ID. NOs: 163-168, respectively, and wherein the immunostimulatory antibody is an anti-PD1 antibody selected from the group consisting of nivolumab and pembrolizumab.

2. A method according to claim 1, wherein said subject has cancer.

3. A method according to claim 2, wherein the cancer is a solid tumour.

4. A method according to claim 1, wherein said Treg depleting antibody molecule and/or said immunostimulatory antibody molecule is selected from the group consisting of a full-size antibody, a Fab, a Fv, an scFv, a Fab', and a (Fab')$_2$.

5. A method according to claim 1, wherein said Treg depleting antibody molecule is a human IgG1 antibody, which optionally may be engineered for improved binding to at least one activatory FcγR.

6. A method according to claim 1, wherein the Treg depleting antibody molecule is selected from the group consisting of antibody molecules comprising a variable heavy chain selected from the group consisting of SEQ. ID. NOs: 7, 15, 23, 31, 39, 47, 55, 63, 71, 159, and 169, and/or a variable light chain selected from the group consisting of SEQ. ID. NOs: 8, 16, 24, 32, 40, 48, 56, 64, 72, 160, and 170.

7. A method according to claim 1, wherein the Treg depleting antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; or SEQ. ID. NOs: 47 and 48; SEQ. ID. NOs: 55 and 56; SEQ. ID. NOs: 63 and 64, SEQ. ID. NOs: 71 and 72; SEQ. ID. NOs: 159-160; and SEQ. ID. NOs: 169-170.

8. A method according to claim 1, wherein the immunostimulatory antibody molecule is a human IgG2 antibody or a human IgG4 antibody molecule, which optionally may be engineered for enhanced binding to human FcγRIIB over activatory Fc gamma receptors.

9. A method according to claim 8, wherein the immunostimulatory antibody molecule is a human IgG2b antibody molecule, which optionally may be engineered for enhanced binding to human FcγRIIB over activatory Fc gamma receptors.

10. An anti-4-1BB antibody molecule selected from the group consisting of antibody molecules comprising VH-CDR1, VH-CDR2, VH-CDR3, VL-CDR1, VL-CDR2 and VL-CDR3 selected from SEQ. ID. NOs: 1-6 or SEQ. ID. NOs: 9-14 or SEQ. ID. NOs: 17-22 or SEQ. ID. NOs: 25-30 or SEQ. ID. NOs: 33-38 or SEQ. ID. NOs: 41-46 or SEQ. ID. NOs: 49-54 or SEQ. ID. NOs: 57-62 or SEQ. ID. NOs: 65-70 or SEQ. ID. NOs: 153-158 or SEQ. ID. NOs: 163-168, respectively.

11. A method according to claim 3, wherein the solid tumour is selected from the group consisting of sarcomas, carcinomas, lymphomas and ovarian cancer.

12. A method according to claim 3, wherein the solid tumour selected from the group consisting of squamous cell carcinoma (SCC), thymoma, neuroblastoma or ovarian cancer.

13. An anti-4-1BB antibody molecule according to claim 10, wherein the antibody molecule is selected from the group consisting of antibody molecules comprising a variable heavy chain selected from the group consisting of SEQ. ID. NOs: 7, 15, 23, 31, 39, 47, 55, 63, 71, 159, and 169, and/or a variable light chain selected from the group consisting of SEQ. ID. NOs: 8, 16, 24, 32, 40, 48, 56, 64, 72, 160, and 170.

14. An anti-4-1BB antibody molecule according to claim 10, wherein the antibody molecule is selected from the group consisting of antibody molecule comprising SEQ. ID. NOs: 7 and 8; SEQ. ID. NOs: 15 and 16; SEQ. ID. NOs: 23 and 24; SEQ. ID. NOs: 31 and 32; SEQ. ID. NOs: 39 and 40; or SEQ. ID. NOs: 47 and 48; SEQ. ID. NOs: 55 and 56; SEQ. ID. NOs: 63 and 64, SEQ. ID. NOs: 71 and 72; SEQ. ID. NOs: 159-160; and SEQ. ID. NOs: 169-170.

* * * * *

UNITED STATES PATENT AND TRADEMARK OFFICE
CERTIFICATE OF CORRECTION

| | |
|---|---|
| PATENT NO. | : 11,447,549 B2 |
| APPLICATION NO. | : 16/633740 |
| DATED | : September 20, 2022 |
| INVENTOR(S) | : Frendéus et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this
Twenty-seventh Day of February, 2024

Katherine Kelly Vidal
*Director of the United States Patent and Trademark Office*